(12) United States Patent
Willison et al.

(10) Patent No.: US 6,255,070 B1
(45) Date of Patent: *Jul. 3, 2001

(54) FOLDING PROTEIN COMPLEXES

(75) Inventors: Keith Robert Willison; Hiroshi Kubota; Alan Ashworth, all of London (GB)

(73) Assignee: Cancer Research Campaign Technology Limited, London (GB)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/687,590

(22) PCT Filed: Jan. 31, 1995

(86) PCT No.: PCT/GB95/00192

§ 371 Date: Oct. 11, 1996

§ 102(e) Date: Oct. 11, 1996

(87) PCT Pub. No.: WO95/20654

PCT Pub. Date: Aug. 3, 1995

(30) Foreign Application Priority Data

Jan. 31, 1994 (GB) .................................................. 9401791
Sep. 9, 1994 (GB) .................................................. 9418234

(51) Int. Cl.[7] .......................... C12N 15/12; C12N 15/63; C07K 14/47

(52) U.S. Cl. ................. 435/69.1; 435/252.3; 435/254.11; 435/325; 435/320.1; 435/471; 536/23.5; 530/325; 530/350

(58) Field of Search ........................ 424/185.1; 435/69.1, 435/252.3, 254.11, 320.1, 325, 471; 530/325, 350, 806; 536/23.5

(56) References Cited

FOREIGN PATENT DOCUMENTS

93/25681 * 12/1993 (WO) .

OTHER PUBLICATIONS

Kriegler, M. in Gene Transfer and Expression Chapter 4, pp. 85–95, M Stockton Press, New York, NY, 1990.*

Ehmann et al. Two Tcp–1 related but highly divergent gene families exist in oat encoded proteins of assumed chaperonin function. FEBS Letters. vol. 336, pp. 313–316, Dec. 27, 1993.*

Segel et al. Isolation of a gene encoding a chaperonin–like protein by complementation of yeast amino acid transport mutants with human cDNA. Proceedings of the National Academy of Sciences, USA. vol. 89, No. 13, pp. 6060–6064, Jul. 1, 1992.*

Mikayama et al. Proc. Natl. Acad. Sci. USA vol. 90, pp. 10056–10060, 1993.*

Voet et al. Biochemistry. John Wiley & Sons, Inc., pp. 126–128 and 228–234, 1990.*

* cited by examiner

*Primary Examiner*—Prema Mertz
(74) *Attorney, Agent, or Firm*—Townsend & Townsend & Crew LLP

(57) ABSTRACT

Nucleic acid encoding subunits of a polypeptide folding complex containing TCp-1 is useful in expression of the subunits for assembly of the complex in vitro or in vivo. The complex promotes folding of polypeptides, such as tubulin, e.g., following recombinant expression. The sequences share a high degree of homology but the C-termini are sufficiently different to enable peptides with sequences derived therefrom to be used in obtaining antibodies specific for the various subunits, i.e., able to distinguish between them. The antibodies may be used in analysis and design of complexes able to fold different polypeptides.

50 Claims, 31 Drawing Sheets

Figure 9:
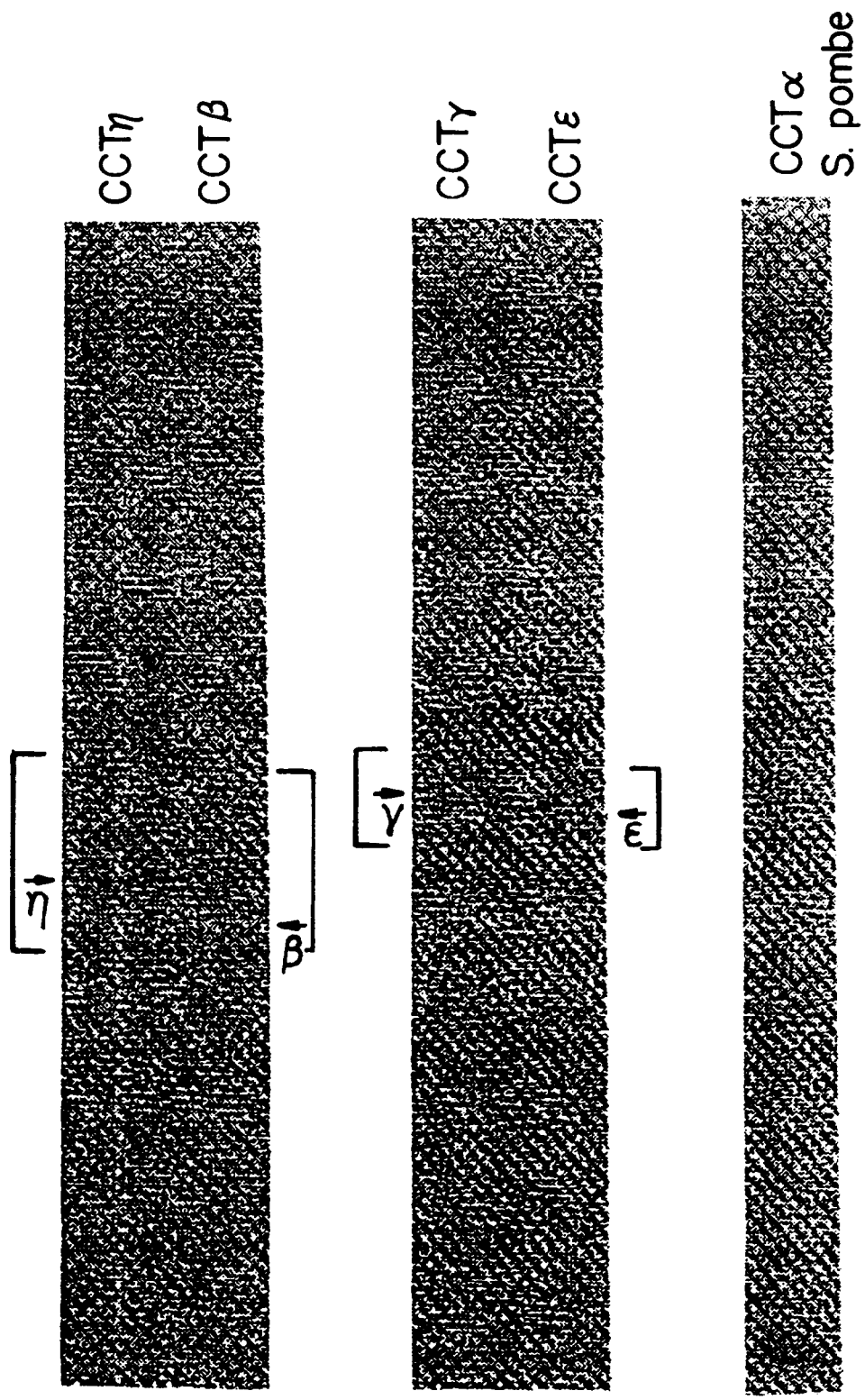

Fig. 1a.
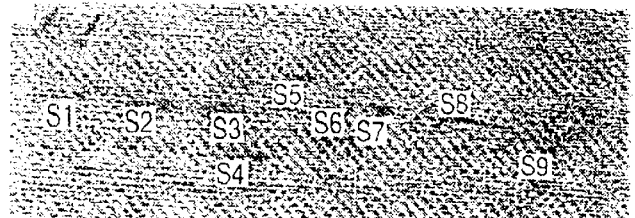
Fig. 1b.
Fig. 1c.
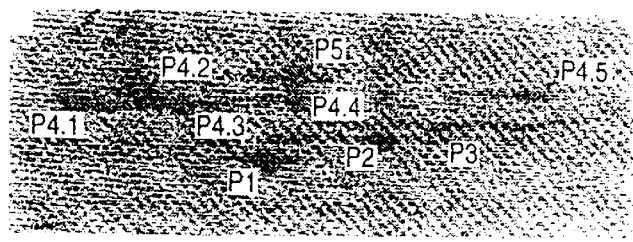
Fig. 1d.
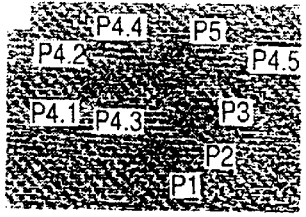
Fig. 1e.
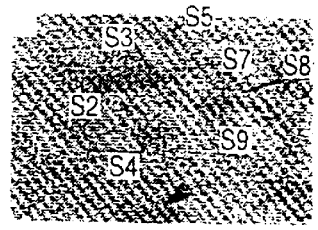
Fig. 1f.
| MOUSE | | | BOVINE | | |
|---|---|---|---|---|---|
| Spot | pI | M.W.(KD) | Spot | pI | M.W.(KD) |
| S1 | 6.25 | 62 | P4.1 | 6.1 | 60 |
| S2 | 6.35 | 61 | P4.2 | 6.3 | 61 |
| S3 | 6.5 | 60 | P4.3 | 6.45 | 60 |
| S4 | 6.65 | 53 | P1 | 6.8 | 52 |
| S5 | 6.85 | 65 | P5 | 6.85 | 65 |
| S6 | 6.9 | 62.5 | P4.4 | 6.85 | 60.5 |
| S7 | 6.95 | 62 | P2 | 7.0 | 56 |
| S8 | 7.1 | 57 | P3 | 7.1 | 58 |
| S9 | >7.2 | 56 | P4.5 | >7.2 | 61 |

Fig.2.

```
pTε5  (M)    KSRLMGLEALKSHIMAAKAVANTMRTSLGPNGLDKMMVDKDGDV  ⎤
p384  (H)    KSRLMGLEALKSHIMAAKAVANTMRTSLGPNGLDKMMVDKDGDV  ⎦ Group 1
pG4   (C)    QKRITGVEAVKSHILAARAVANTLRTSLGPRGLDKMLVSPDGDV
pTδ2  (M)    QDRDKPAQIRFSNISAAKAVADAIRTSLGPKGMDKMIQDGKGDV  ⎤
pG3   (C)    KDKDKPESVRNSNIVAAKAVADAVRTSLGPRGMDKMIQSGNGDV  ⎦ Group 2
Tcp-1 (M)    GDRSTGEAVRSQNVMAAASIANIVKSSFGPVGLDKMLVDDIGDV  ⎤
TCP1  (H)    GDRSTGETIRSQNVMAAASIANIVKSSLGPVGLDKMLVDDIGDV  |
pG1   (C)    GKRTTGQGIRSQNVTAAVAIANIVKSSLGPVGLDKMLVDDVGDV  ⎥ Group 3
TCP1  (S)    GDRQSGQDVRTQNVMACQAVSNIVKTSLGPVGLDKMLVDDIGDV  ⎦
pCBL80(M)    TDSSQGIPQLVSNISACQVIAEAVRTTLPRGMDKLIVDGRGKA   — Group 4
pTγ7  (M)    TKRESGRKVQSGNNINAAKTIADIIRTCLGPKSMMKMLLDPMGGI — Group 5
pTζ12 (M)    AEVARVQAALAVNISAARGLQDVLRTNLGPKGTMKMLVSGAGDI  ⎤ Group 6
pG2   (C)    AELARHAAALELNISGARGLQDVMRSNLGPKGTLKMLVSGAGDI  ⎦
pTβ2  (M)    ADEERAEIARLSSFIGAIAIGDLVKSTLGPKAMDKILLSSGRDA  ⎤
p383  (H)    ADEERAETARLTSFIGAIAIGDLVKSTLGPKGMDKILLSSGRDA  ⎥ Group 7
4950  (S)    VTEERAENARLSAFVGAIAVGDLVKSTLGPKGMDKLLQSASSNT  ⎦
```

Fig. 3a.

```
MASLSLAPVNIFKAGADEERAEIARLSSFIGAIAIGDLVKSTLGPKGMDK      050
ILLSSGRDAALMVTNDGATILKNIGVDNPAAKVLVDMSRVQDDEVGDGTT      100
                                        P1(T31)
SVTVLAAELLREAESLIAKKIHPQTIISGWREATKAAREALLSSAVDHGS      150
DEARFWQDLMNIAGTTLSSKLLTHHKDHFTKLAVEAGLRLKGSGNLEAIH      200
VIKKLGGSLADSYLDEGFLLDKKIGVNQPKRIENAKILIANTGMDTDKIK      250
                                       X X  B4(R162)
IFGSRVRVDSTAKVAEIEHAEKEKMKEKVERILKHGINCFINRQLIYNYP      300
EQLFGAAGVMAIEHADFAGVERLALVTGGEIASTFDHPELVKLGSCKLIE      350
EVMIGEDKLIHFSGVALGEACTIVLRGATQQILDEAERSLHDALCVLAQT      400
VKDPRTVYGGGCSEMLMAHAVTQLANRTPGKEAVAMESFAKALRMLPTII      450
ADNAGYDSADLVAQLRAAHSEGHITAGLDMKEGTIGDMAVLGITESFQVK      500
RQVLLSAAEAAEVILRVDNIIKAAPRKRVPDHHPC    535
```

Fig. 3b.

```
MMGHRPVLVLSQNTKRESGRKVQSGNINAAKTIADIIRTCLGPKSMMKML      050
LDPMGGIVMTNDGNAILREIQVQHPAAKSMIEISRTQDEEVGDGTTSVII      100
LAGEMLSVAEHFLEQQMHPTVVISAYRMALDDMISTLKKISTPVDVNNRE      150
MMLSIINSSITTKVISRWSSLACNIALDAVKTVQFEENGRKEIDIKKYAR      200
VEKIPGGIIEDSCVLRGVMINKDVTHPRMRRYIKNPRIVLLDSSLEYKKG      250
ESQTDIEITREEDFTRILQMEEEYIHQLCEDIIQLKPDVVITEKGISDLA      300
               N    QQ      XX   P5(T36)
QHYLMRANVTAIRRVRKTDNNRIARACGARIVSRPEELREDDVGTGAGLL      350
EIKKIGDEYFTFITDCKDPKACTILLRGASKEILSEVERNLQDAMQVCRN      400
VLLDPQLVPGGGASEMAVAHALTEKSKAMTGVEQWPYRAVAQALEVIPRT      450
   P5(T32)                    B1(R133)
LIQNCGASTIRLLTSLRAKHTQESCETWGVNGETGTLVDMKELGIWEPLA      500
VKLQTYKTAVETAVLLLRIDDIVSGHKKKGDDQNRQTGAPDAGQE    545
```

Fig.3c.

MPENVASRSGAPTAGPGSRGKSAYQDRDKPAQIRFSNISAAKAVADAIRT  050

SLGPKGMDKMIQDGKGDVTITNDGATILKQMQVLHPAARMLVELSKAQDI  100

EAGDGTTSVVIIAGSLLDSCTKLLQKGIHPTIISESFQKALEKGLEILTD  150
⎯⎯⎯⎯⎯⎯X⎯⎯⎯P3(T31)

MSRPVQLSDRETLLNSATTSLNSKVVSQYSSLLSPMSVNAVMKVIDPATA  200

TSVDLRDIKIVKKLGGTIDDCELVEGLVLTQKVANSGITRVEKAKIGLIQ  250

FCLSAPKTDMDNQIVVSDYAQMDRVLREERAYILNLVKQIKKTGCNVLLI  300

QKSILRDALSDLALHFLNKMKIMVVKDVEREDIEFICKTIGTKPVAHIDQ  350

FTADMLGSAELAEEVSLNGSGKLFKITGCTSPGKTVTIVVRGSNKLVIEE  400

AERSIHDALCVIRCLVKKRALIAGGGAPEIELALRLTEYSRTLSGMESYC  450

VRAFADAMEVIPSTLAENAGLNPISTVTELRNRHAQGEKTTGINVRKGGI  500
⎯⎯⎯⎯⎯⎯⎯⎯⎯⎯⎯P3(T50)⎯⎯⎯⎯⎯⎯⎯X⎯

SNILEEMVVQPLLVSVSALTLATETVRSILKIDDVVNTR  539

Fig.3d.

MASVGTLAFDEYGRPFLIIKDQDRKSRLMGLEALKSHIMAAKAVANTMRT  050

SLGPNGLDKMMVDKDGDVTITNDGATILSMMDVDHQIAKLMVELSKSQDD  100

EIGDGTTGVVVLAGALLEEAEQLLDRGIHPIRIADGYEQAARIAIQHLDK  150

ISDKVLVDINNPEPLIQTAKTTLGSKVINSCHRQMAEIAVNAVLTVADME  200

RRDVDFELIKVEGKVGGRLEDTKLIKGVIVDKDFSHPQMPKKVVDAKIAI  250

LTCPFEPPKPKTKHKLDVMSVEDYKALQKYEKEKFEEMIKQIKETGANLA  300

ICQWGFDDEANHLLLQNGLPAVRWVGGPEIELIAIATGGRIVPRFSELTS  350

EKLGFAGVVQEISFGTTKDMLVIEKCKNSRAVTIFIRGGNKMIIEEAKR  400

SLHDALCVIRNLIRDNRVVYGGGAAEISCALAVSQEADKCPTLEQYAMRA  450

FADALEVIPMALSENSGMNPIQTMTEVRARQVKESNPALGIDCLHKGSND  500

MQYQHVIETLIGKKQQISLATQMVRMILKIDDIRKPGESEE  541

Fig.3e.

```
MAAVKTLNPKAEVARAQAALAVNISAARGLQDVLRTNLGPKGTMKMLVSG      050
AGDIKLTKDGNVLLHEMQIQHPTASLIAKVATAQDDITGDGTTSNVLIIG      100
ELLKQADLYISEGLHPRIITEGFEAAKEKALQFLEQVKVSKEMDRETLID      150
VARTSLRTKVHAELADVLTEAVVDSILAIRKKDEPIDLFMVEIMEMKHKS      200
ETDTSLIRGLVLDHGARHPDMKKRVENAYILTCNVSLEYEKTEVNSGFFY      250
KSAEEREKLVKAERKFIEDRVKKIIELKKKVCGDSDKGFVVINQKGIDPF      300
              B3(R170)
SLDALAKEGIVALRRAKRRNMERLTLACGGIALNSFDDLNPDCLGHAGLV      350
YEYTLGEEKFTFIEKCNNPRSVTLLVKGPNKHTLTQIKDAIRDGLRAVKN      400
AIDDGCVVPGAGAVEVALAEALIKYKPSVKGRAQLGVQAFADALLIIPKV      450
LAQNSGFDLQETLVKVQAEHSESGQLVGVDLSTGEPMVAAEMGVWDNYCV      500
KKQLLHSCTVIATNILLVDEIMRAGMSSLKG    531
```

Fig.3f.

```
MMPTPVILLKEGTDSSQGIPQLVSNISACQVIAEAVRTTLGPRGMDKLIV      050
DGRGKATISNDGATILKLLDVVHPAAKTLVDIAKSQDAEVGDGTTSVTLL      100
                                  P2
AAEFLKQVKPYVEEGLHPQIIIRAFRTATQLAVNKIKEIAVTVKKQDKVE      150
 —  X    B2(R115)         B2(R124)
QRKMLEKCAMTALSSKLISQQKVFFAKMVVDAVMMLDELLQLKMIGIKKV      200
QGGALEESQLVAGVAFKKTFSYAGFEMQPKKYKNPKIALLNVELELKAEK      250
DNAEIRVHTVEDYQAIVDAEWNILYDKLEKIHQSGAKVILSKLPIGDVAT      300
QYFADRDMFCAGRVPEEDLKRTMMACGGSIQTSVNALVPDVLGHCQVFEE      350
TQIGGERYNFFTGCPKAKTCTIILRGGAEQFMEETERSLHDAIMIVRRAI      400
KNDSVVAGGGAIEMELSKYLRDYSRTIPGKQQLLIGAYAKALEIIPRQLC      450
DNAGFDATNILNKLRARHAQGGMWYGVDINNENIADNFQAFVWEPAMVRI      500
NALTAASEAACLIVSVDETIKNPRSTVDPPAPSAGRGRGQARFH    544
```

Fig. 4a.

```
                          20                 40                  60                 80                100
                           .                  .                   .                  .                  .
CCTα   ----------------------MEGPLSVFGDRSTGEAVRSQNVMAAASIANIVKSSFGPVGLDKMLVDDIGD--VTITNDGATILKLLEVEHPAAKVICELADLQ
CCTβ   -------------MASLSLAPVNIFKAGADERAEIARLSSFIGAIAGDLVKSTLGPKGMDKILLSSGRDAALMVTNDGATILKNIGVDNPAAKVLVDMSRVQ
CCTγ   -------------MMGHRPVLVLSQNTKRESGRKVQSGNINAAKTIADIIRTCLGPKSMMKMLLDPMGG--IVMTNDGNAILREIQVQHPAAKSMIEISRTQ
CCTδ   MPENVASRSGAPTAGPGSRGKSAYQDRDKPAQIRFSNISAAKAVADAIRTSLGPKGMDKMIQDGKGD--VTITNDGATILKQMQVLHPAARMLVELSKAQ
CCTε   MASVGTLAFDEYGRPFLIIKDQDRKSRLMGLEALKSHIMAAKAVANTMRTSLGPNGLDKMVDKDGD--VTITNDGATILSMMDVDHQIAKLMVELSKSQ
CCTζ   ----------------MAAVKTLNPKAEVARAQAALAVNISAARGLQDVLRTNLGPKGTMKMLVSGAGD--IKLTKDGNVLLHEMQIQHPTASLIAKVATAQ
CCTη   ----------------MMPTPVILLKEGTDSSQGIPQLVSNISACQVIAEAVRTTLGPRGMDKLIVDGRGK--ATISNDGATILKLLDDVVHPAAKTLVDIAKSQ
CCTθ   ---------MALHVPKAPGFAQMLKDGAKHFSGLEEAVYRNIQACKELAQTTRTAYGPNGMNKMVINRLEK--LFVTNDAATILRELEVQHPAAKMIVMASHMQ
TF55   ---MATATVATTPEGIPVIILKEGSSRTYGKEALRANIAAVKAIEEALKSTYGPRGMDKMFVDSLGD--ITITNDGATILDKMDLQHPTGKLLVQIAKGQ
Cons.  .........PVIILS.G.DRS.GEEAL.SNISAAKAIADAVRTSLGPKGMDKMLVDG.GD..VTITNDGATILKELQVQHPAAKLLVELAK.Q
                                              K     R         KST          I           MD         IS 120                140                 160                180                200
                           .                  .                   .                  .                  .
CCTα   DKEVGDGTTSVVIIAAELLKNADELVKQKIHPTSVISGYRLACKEAVRYINENLIINTDELGR---DCLINTAKTSMSSKIIGINGDYFANMVVDAVLAV
CCTβ   DDEVGDGTTSVTVLAAELLREAESLIAKKIHPTIISGWREATKAAREALLSSAVDHGSDEAR-FWQDLMNIAGTTLSSKLLTHHKDHFTKLAVEAGLRL
CCTγ   DEEVGDGTTSVIIAGEMLSVAEHFLEQQMHPTVISAYRMALDDMISTLKKISTPVDVNNRE----MMLSIINSSITTKVISRWSSLACNIALDAVKTV
CCTδ   DIEAGDGTTSVVIAGSLLDSCTKLLQKGIHPTIISESFQKALEKGLEILTDMSRPVQLSDRE---TLLNSAATTSLNSKVVSQYSSLLSPMSVNAVMKV
CCTε   DDEIGDGTTGVVVLAGALLEEAEQLLDRGIHPIRIADGYEQAARIAIQHLDKISDKVLVDINN--PEPLIQTAKTTLGSKVINSCHRQMAEIAVNAVLTV
CCTζ   DDITGDGTTSNVLIIGELLKQADLYISEGLHPRIITEGFEAAKEKALQFLEQVKVSKEMDRET-----LIDVARTSLRTKVHAELADVLTEAVVDSILAI
CCTη   DAEVGDGTTSVTLLAAEFLKQVPVEEGLHPQIIRAFRTATQLAVNKIKEIAVTVKKQDKVEQRKMLEKCAMTALSSKLISQQKVFFAKMVVDAVMML
CCTθ   EQEVGDGTNFVLVFAGALLELAEELLRIGLSVSEVISGYEIACKKAHEILPELVCCSAKNLRD--VDEVSSLLRTSIMSKQYGSETFLAKLIAQACVSIF
TF55   DEETADGTKTAVILAGELAKKAEDLLYKEIHPTIIVSGYKKAEEIALKTIQDIAQPVSINDTD----VLRKVALTSLGSKAVAGAREYLADLVKKAVAQV
Cons.  DDEVGDGTTSVVILAGELLK.AE.LL.KGIHPTIIISGYR.A.EKAL.TL.EIA.PV..DDR.....MLIN.A.TSLSSKVIS...DLLA.MVVDAVL.V
                        V A                V   FE K               I S    N                   F    IA         K 220                240                 260                280                300
                           .                  .                   .                  .                  .
CCTα   KYTDARGQPRYPVNSVNILKAHGRSQIESMLINGYALNCVVGSQG---MPKRIVNAKIACLDFSLQKTKMKL-GVQVITDPEKLDQIRQRESDITKERI
CCTβ   ----KGSGNLEAIHVIRKLGSLADSYLDEGFLLDKKIGVNQ-----PKRIENAKILIANTGMDTDKIKIFGSRVRVDSTAKVAEIEHAEKEKMKEKV
CCTγ   QFEENGRKEIDIKKYARVEKIPGGIIEDSCVLRGVMINKDV------THPRMRRYIKNPRIVLLDSSLEY-KKGESQTDIEITREEDFTRILQMEEEY
CCTδ   --IDPATATSVDLRDIKIVKKLGGTIDDCELVEGLVLTQKVANSG--ITRVEKAKIGLIQFCLSAPKTDM-DNQIVVSDYAQMDRVLREERAYIINLV
CCTε   ---ADMERRDVDFELIKVEGKVGGRLEDTKLIKGVIVDKDFSHPQ--MPKKVVDAKIAILTCPFEPPKPKT-KHKLDVMSVEDYKALQKYEKEKFEEMI
CCTζ   ----RKKDEPIDLFMVEIMEMKHKSETDTSLIRGLVLDHGARHPD--MKKRVENAYILTCNVSLEYEKTEV-NSGFFYKSAEEREKLVKAERKFIEDRV
CCTη   ;---DELLQLKMIGIKKVQGGALEESQLVAGVAFKKTFSYAGFEMQPKKYKNPKIALLNVELELKAEKD-NAEIRVHTVEDYQAIVDAEWNILYDKL
CCTθ   -----PDSGNFNVDNIRVCKILGSGIYSSVLHGMVFKKETEGD-----VTSVKDAKIAVYSCPFDGMITET-KGTVLIKTAEELMNFSKGEENLMDAQV
TF55   -AELRGDKWYVKLKHGGSINDTQLVYGIVVDKEVVHPG--MPKRIENAKIALLDASLEVEKPEL-DAEIRINDPTQMHKFLEEEENILKEKV
Cons.  ....KE.VDL..I.I.RKLGGSI.DS.LV.GVVLDK.V.HPG....MPKRIENAKIALLN.SLE..K.EL.K..IRV.D.E....I.KAE...IMEEKV
           V                I                          V                         K       V I            K
```

Fig. 4b.

Fig.5.
```
CCTα      KEVGDGTTSVVIIA
CCTβ      DEVGDGTTSVTVLA
CCTγ      EEVGDGTTSVIILA
CCTδ      IEAGDGTTSVVIIA
CCTε      DEIGDGTTGVVVLA
CCTζ      DITGDGTTSNVLII
CCTη      AEVGDGTTSVTLLA
CCTθ      QEVGDGTNFVLVFA cAPK-α    KTLGTGSFGRVMLV
PKC-α     MVLGKGSFGKVMLA
CaMII-α   EELGKGAFSVVRRC
SNF1      KTLGEGSFGKVKLA
cdc2+     EKIGEGTYGVVYKA
CDC7      DKIGEGTFSSVYKA
Raf       TRIGSGSFGTVYKG
Src       VKLGQGCFGEVWMG
Abl       HKLGGGQYGEVYEG
EGFR      KVLGSGAFGTVYKG
INSR      RELGQGSFGMVYEG
PDGFR     RTLGSGAFGQVVEA
```

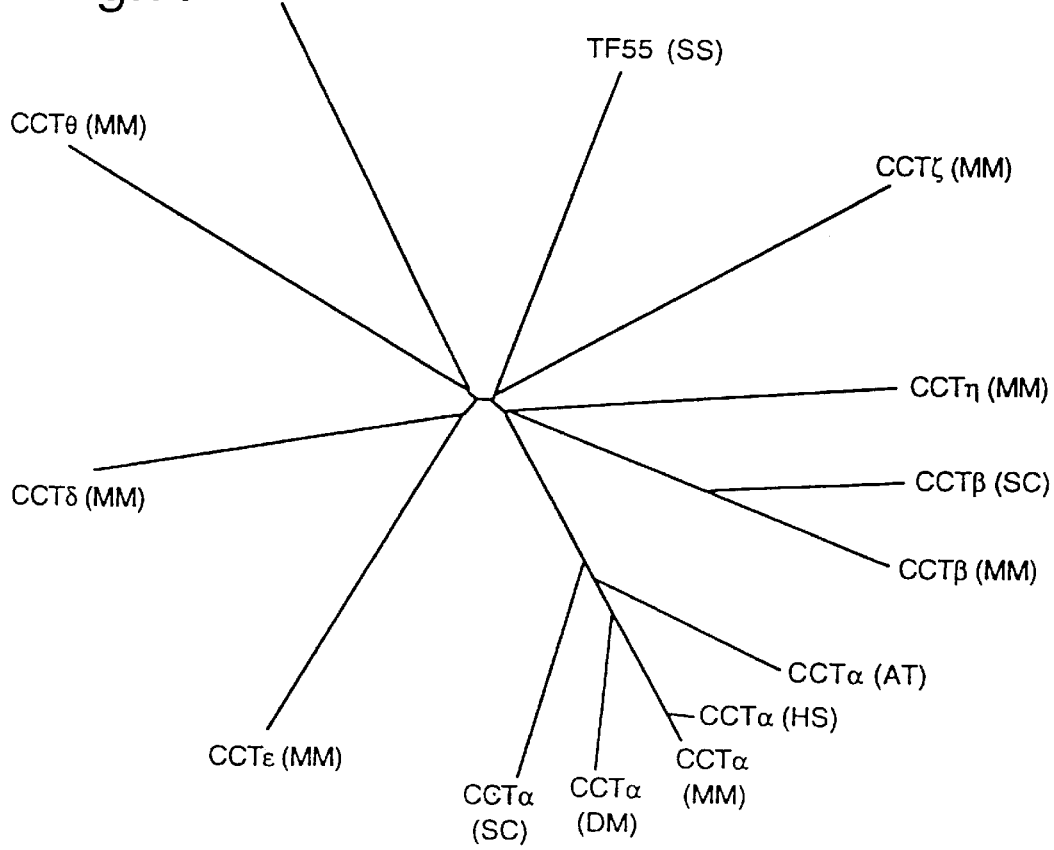

Fig.7.

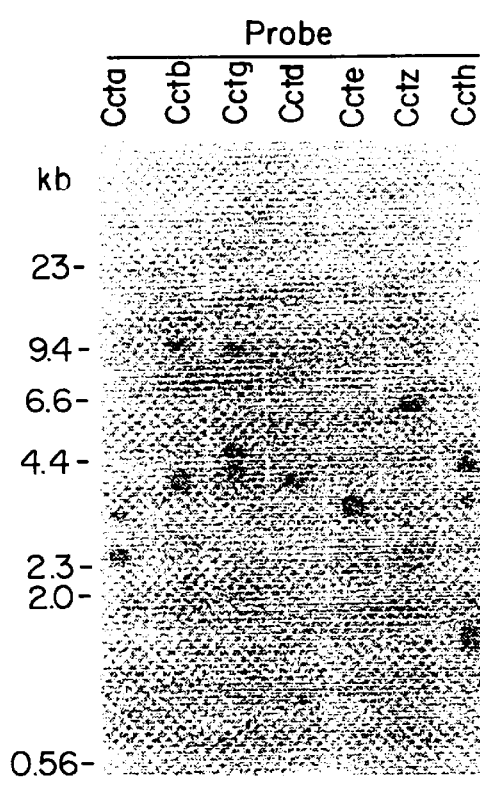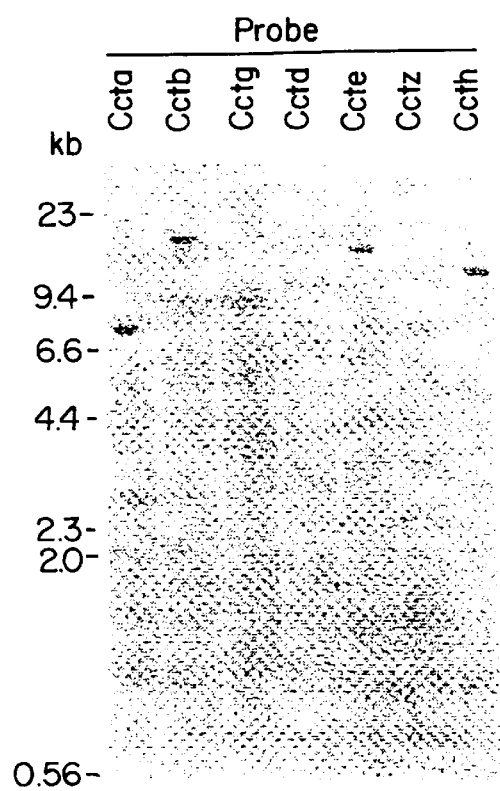
Fig. 6a.
Fig. 6b.

Tcp-1 cDNA sequence

```
TCTCAGAGCGGAGCTATCGGTTGTCTGCGGCCCGTAGTGAGCTTTGCTTCGTTTCCTGAAGATGAGGGTCCTTTGTCCGTGTCGGGAC
                                                   M  E  G  P  L  S  V  F  G  D

CGCAGCACTGGGGAGGCGGTCCGCTCCCAGAATGTTATGGCTGCAGCTTCTATTGCCAACATTGTTAAAGTTCTTTGGCCAGTTGGC
 R  S  T  G  E  A  V  R  S  Q  N  V  M  A  A  A  S  I  A  N  I  V  K  S  S  F  G  P  V  G

TTGGATAAAATGTTGGTGGATGATATATTGGTGATGTAACCATCCTGAAGTTACTGGAGTAGAACATCCC
 L  D  K  M  L  V  D  D  I  G  D  V  T  I  T  N  D  G  A  T  I  L  K  L  L  E  V  E  H  P

GCAGCCAAAGTTCTGTGTGAGCTGGCTGACCTGCAAGACAAGAAGTTGGAGATGGAACTACTCAGTGTAATCATTGCAGCGGAGCTT
 A  A  K  V  L  C  E  L  A  D  L  Q  D  K  E  V  G  D  G  T  T  S  V  V  I  I  A  A  E  L

CTGAAAAATGCAGATGAGCTAGTCAAACAGAAAATTCATCCAACATCAGTTATTAGTGGCTATCGTCTTGCCTGCAAGGAAGCGGTCGT
 L  K  N  A  D  E  L  V  K  Q  K  I  H  P  T  S  V  I  S  G  Y  R  L  A  C  K  E  A  V  R

TATATCAATGAGAACCTGATTATTAACACAGACGAACTGGAAGAGACTGCTAAGACATCGTCTAAGACATCGTCTCAAATT
 Y  I  N  E  N  L  I  I  N  T  D  E  L  G  R  D  C  L  I  N  T  A  K  T  S  H  S  S  K  I

ATTGGAATAAATGGTGATTACTTTGCTAATATGGTAGTAGATGCTGTTGCTGTTAATACACAGATGCCAGAGCCTCAATTGTGTGT
 I  G  I  N  G  D  Y  F  A  N  M  V  V  D  A  V  L  A  V  K  Y  T  D  A  R  G  Q  P  R  Y

CCAGTCAATTCGTTAATATTCGTAAAGCCCATGGAGAGTCAGATAGAAGCATGCTGATCAATGGCTATGCCTCAATTGTGCTTGTT
 P  V  N  S  V  N  I  L  K  A  H  G  R  S  Q  I  E  S  M  L  I  N  G  Y  A  L  N  C  V  V

GGATCTCAGGGCATGCCCAAGAGAATAGTTAATGCAAAAATTGCTTGTCTTGACTTCAGCCTGCAGAAAACAAAAATGAAGCTTGTGTA
 G  S  Q  G  M  P  K  R  I  V  N  A  K  I  A  C  L  D  F  S  L  Q  K  T  K  H  K  L  G  V

CAGGTGGTTATTACAGACCCTGAGAAATTGGACCAAATTAGACAGAGAGAATCACCAAGGACATATCGGATATCAATTGAAGATCTGGCA
 Q  V  V  I  T  D  P  E  K  L  D  Q  I  R  Q  R  E  S  D  I  T  K  E  R  I  Q  K  I  L  A
```

Fig. 8a.

ACTGGTGCCAATGTTATTCTAACCACTGGTGTGGCATTGATGATATGTATCTCAAGTATTTGTGGAAGCTGGTGCCATGGCTGTAGGAGA
T G A N V I L T T G G I D D M Y L K Y F V E A G A H A V R R

GTTTTAAACGAGACCTGAAGCATGTTGCAAAGCTTCTGGAGCAAGTATCCTGTCCTGGCCTGGCCAATTTGAAGGCGAAGAAACTTTT
V L K R D L K H V A K A S G A S I L S T L A N L E G E E T F

GAAGTGACGATGTTGGGACAAGCGGAAGAGGTCGTACAGGAGAATTTGTGATGATGAGCTGATCTTAATCAAAATACTAAGGCTCGT
E V T M L G Q A E E V V Q E R I C D D E L I L I K N L K A R

ACATCTGCTTCAATCATCTTACGAGGAGCAAATGATTCATGTGTGATGAAATGAGCCTCTTTACATGATGCTGTTGTGGTGAAG
T S A S I I L R G A N D F M C D E H E R S L H D A L C V V K

AGAGTTTGGAGTGAAATCTGTGTCCCAGTGGAGTGCTGTAGAAGCTGCCCTGTCCAGTCAATACTGGCCAGTGAATGCTGCCAGGACTCC
R V L E L K S V V P G G G A V E A A L S I Y L E N Y A T N M

GGATCTCGGGAACAGCTGGCCAGTTAAGAGCTTTCACAATGAGCTCAAGTGGATTCCTAATACTGGCCAGTGAATGCTGCCAGGACTCC
G S R E Q L A I A E F A R S L L V I P N T L A V N A A Q D S

ACCGACCTGGTTGCCAAGTAAGCTGAGAGCAACAAGCAGGGTGTTGAACCAACCATAGTTGTTGTGAAGTCAAGTCTGCAACAGAGCT
T D L V A K L R A F H N E A Q V N P E R K N L K W I G L D L

GTCCATGGGAAACCATGAGAACCGAGAGAATTGCGATTGATAAATTACACCCAGAAAGCAAAGACGATAAACCGAAGTTATGAAATGCTGTTCAC
V H G K P R D N K Q A G V F E P T I V K V K S L K F A T E A

GCAATCACCATCCTTCGGATTGACGATCTGATAAATTACACCAGAAAGCAAAGACGATAAACCGAAGTTATGAAATGCTGTTCAC
A I T I L R I D D L I K L H P E S K D D K H G S Y E N A V H

TCTGGAGCCCTTGATGACTGATTGATTTCCCTCTTATTTATAACAGTGTCAGGTGCAATGCCTAGCTTCAGGTCAGGTGTCTCACATTAAGT
S G A L D D *      poly(A)*

ACAGCAAGCTGT

Fig. 8b.

pTbeta2 cDNA Sequence

```
GGCTTCCCGGCGGCGGATTGTGAGGGGTTCTCTCCCTTCCCCTCGAACCATGGCTTCCCTTTCCCTCGCACCTGTTAATATC
                                         M  A  S  L  S  L  A  P  V  N  I

TTCAAGGCTGAGCTGATGAAGAGAGGCCGAGATAGCTCGCCTGTCGTTATCGCCATTGGAGACTTGGTGAAGAGC
 F  K  A  G  A  D  E  E  R  A  E  I  A  R  L  S  S  F  I  G  A  I  A  I  G  D  L  V  K  S

ACTTTGGGACCGAAGGGCATGGACAAAATTCTCCTAAGCAGTGGACGAGACGCCGCTCTGATGGTGACCAACGACGGTGCTACCATTCTC
 T  L  G  P  K  G  M  D  K  I  L  L  S  S  G  R  D  A  A  L  M  V  T  N  D  G  A  T  I  L

AAGAACATTGGTGTGGACAACCCCGCCAGCAAAGTTCTAGTTGATATGTCAAGGGTTCAAGATGATGAAGTTGGTGATGGCACTACCTCT
 K  N  I  G  V  D  N  P  A  A  K  V  L  V  D  M  S  R  V  Q  D  D  E  V  G  D  D  G  T  T  S

GTTACTGTCTTAGCCGCAGAGCTGCTCCGGGAAGCAGAATCTTTAATTGCAAAAAAGATACATCCACAGACCATCATCTCAGGTTGGAGA
 V  T  V  L  A  A  E  L  L  R  E  A  E  S  L  I  A  K  K  I  H  P  Q  T  I  I  S  G  W  R

GAAGCCACAAAGGCAGCAAGAGAGGCCCTGCTCTCATCGGCTGTGGATCATGGTTCTGATGAAGCCAGATTCTGGCAGGACTTAATGAAC
 E  A  T  K  A  A  R  E  A  L  L  S  S  A  V  D  H  G  S  D  E  A  R  F  W  Q  D  L  M  N

ATTGCAGGAACGACATTGTCCTCAAAGCTCCTTACTCACCACAAGGACCACTTTACTAAACTGGCCGTGGAAGCGGGTCTCAGACTGAAA
 I  A  G  T  T  L  S  S  K  L  L  T  H  H  K  D  H  F  T  K  L  A  V  E  A  G  L  R  L  K

GGCTCTGGCAACCTGGAGGCCGATTCATGTCATCAAGAAAACTAGTGGGAGTCTGGCAGACTCCTATCTAGATGAAGGTTTCTTTTTGGAT
 G  S  G  N  L  E  A  I  H  V  I  K  K  L  G  G  S  L  A  D  S  Y  L  D  E  G  F  L  L  D

AAAAAATTGGAGTAAATCAACCAAAGAGAATTGAAAATGCTAAAATTCTTATTGCAAATACTGGGATGACAGACAAATAAAGATA
 K  K  I  G  V  N  Q  P  K  R  I  E  N  A  K  I  L  I  A  N  T  G  M  D  T  D  K  I  K  I

TTTGGCTCTCGGGTAAGAGTTGATTCCACAGCAAAGGTTGCAGAGATAGAACATGCAGAAAAGGAGAAGATGAAGGAGAAAGTTGAACGT
 F  G  S  R  V  R  V  D  S  T  A  K  V  A  E  I  E  H  A  E  K  H  K  E  K  V  E  R
```

Fig. 8c.

Fig. 8d.

pIgamma7 cDNA  Sequence

```
TGTCATTCCTGAGGAGGCAGCGTTTCTTCGCTGCTCTTCTCCAGAAGGTTCGCCGATTCCCCCAGCTCTGGAGAGTCGGCTCTG

CGTCGTGCCGCCATGATGGGCCACCGTCCAGTGCTCGTGTCAGTCAGAACACAAAGCGTGAATCTGGAAGAAAAGTTCAGTCTGGAAAT
           M  M  G  H  R  P  V  L  V  S  Q  N  T  K  R  E  S  G  R  K  V  Q  S  G  N

ATCAATGCTGCAAAGACAATTGCAGATATCATCCGAGACCTGCTTGGGACCCTAAATCTATGATGAAGATGCTTTGGACCCAATGGGAGGC
 I  N  A  A  K  T  I  A  D  I  I  R  T  C  L  G  P  K  S  M  M  K  M  L  L  D  P  M  G  G

ATCGTGATGACCAATGATGGCAATGCCATTCTTCGAGAGATTCAAGTCCAGCATCCCGCAGCAAAGTCCATGATTGAAATTAGCAGGACC
 I  V  M  T  N  D  G  N  A  I  L  R  E  I  Q  V  Q  H  P  A  A  K  S  M  I  E  I  S  R  T

CAGGATGAAGAGGTTGGAGATGGGACCACACATCAGTAATTATTCTGGGGAGAAATGCTCTCTGTGGCTGAACACTTCCTAGAGCAGCAG
 Q  D  E  E  V  G  D  G  T  T  S  V  I  I  L  A  G  E  M  L  S  V  A  E  H  F  L  E  Q  Q

ATGCACCCAACAGTGGTGATCAGTGCTTACCGCATGCACTTGGATGATATGATCAGCACTCTGAAGAAATCAGTACTCCTGTTGATGTC
 M  H  P  T  V  V  I  S  A  Y  R  M  H  A  L  D  D  M  I  S  T  L  K  K  I  S  T  P  V  D  V

AATAACCGTGAGATGATGTTGAGCATCATCAATAGTCTCTATTACAAAGTCATCAGTCGGTGTCCTCCTTGGCATGCAACATTGCA
 N  N  R  E  M  M  L  S  I  I  N  S  S  I  T  T  K  V  I  S  R  W  S  S  L  A  C  N  I  A

GTGGATGCTGTTAAGACTGTGCAGTTTGAAGAGAATGGCAGAAAGGAAATTGACATCAAAAATATGCAAGGTAGAAAGATACCCGGG
 L  D  A  V  K  T  V  Q  F  E  E  N  G  R  K  E  I  D  I  K  K  Y  A  R  V  E  K  I  P  G

GGCATCATTGAAGACTCATGTGTCTTACGTGGAGTTATGATTAACAAGGATGTGACCCATCCAAGGATGCGCCGCTATATTAAGAATCCT
 G  I  I  E  D  S  C  V  L  R  G  V  M  I  N  K  D  V  T  H  P  R  M  R  R  Y  I  K  N  P

CGAATTGTGCTATTGGATTCTTCTTTGAGTACAAGAAGGAGAAAGGAGAGCCAGACCGACATCGAGATTACCCGGGAGGACTTCACGCGG
 R  I  V  L  L  D  S  S  L  E  Y  K  K  G  E  S  Q  T  D  I  E  I  T  R  E  E  D  F  T  R

ATCCTGCAGATGGAGGAGGAGTACATCCATCAGCTGTGAGGACATCATCCAGCTGAAGCCTGACGTGGTCATCACAGAGAAGGGCATC
 I  L  Q  M  E  E  E  Y  I  H  Q  L  C  E  D  I  Q  L  K  P  D  V  V  I  T  E  K  G  I
```

Fig. 8e.

```
TCAGATTAGTCTCAGCACTACCTCATGCGGGCCAATGTCACAGCCATTGTGAGTCCGGAAACAGACAATAATGCATTGCTAGAGCC
 S  D  L  A  Q  H  Y  L  H  R  A  N  V  T  A  I  R  R  V  R  K  T  D  N  N  R  I  A  R  A

TGTGGGGCACGGATAGTCAGCCGACCTGAGGAACTGAGAGAAGATGATGTTGGTACAGGGCAGGCTTATTGGAAATCAAGAAGATTGGA
 C  G  A  R  I  V  S  R  P  E  E  L  R  E  D  D  V  G  T  G  A  G  L  L  E  I  K  K  I  G

GATGAGTACTTTACATTCATCACTGACTGCAAAGACCCTGCAAAGGCCTGCACCATTCTCTTAGAGGAGCCAGCAAGAGATACTCTCGGA
 D  E  Y  F  F  I  T  D  C  K  D  P  K  A  C  T  I  L  L  R  G  A  S  K  E  I  L  S  E

GTAGAAGCAACCTCCAGGATGCCATGCAAGTGTGCCGCAATGTCTACTGGACCCTCAGCTGGTGCCTGGTGGAGCCTGAGATG
 V  E  R  N  L  Q  D  A  M  Q  V  C  R  N  V  L  L  D  P  Q  L  V  P  G  G  A  S  E  M

GCTGTGGCTCATGCCTTGACAGAAAAATCTAAGGCCATGACTGGTGTGGAACAGTGGCCCAGGCGTTAGAGGTC
 A  V  A  H  A  L  T  E  K  S  K  A  M  T  G  V  E  Q  W  P  Y  R  A  V  A  Q  A  L  E  V

ATCCCTCGACCTTGATCCAGAATTGTGGGCCAGTGCTACCCTTGTCTGCTTACCTGTCCCTTCGGGCACACAGGAGAGTTGTGAG
 I  P  R  T  L  I  Q  N  C  G  A  S  T  I  R  L  L  T  S  L  R  A  K  H  T  Q  E  S  C  E

ACCTGGGGTGTGAATGGTGAGACTGGTACCTTGGTGGACATGAAAGAGCTGGGTATTTGGGAGCCATTGGCTGTGAAGCTACAAACGTAC
 T  W  G  V  N  G  E  T  G  T  L  V  D  M  K  E  L  G  I  N  E  P  L  A  V  K  L  Q  T  Y

AAACAGCAGTAGAGACTGCAGTTGTCCTGCTTCTGCGGATTGATGACATTGTCTCTGGCCACAAGAAGAAGGGTGATGACCAGAACCGGCAA
 K  T  A  V  E  T  A  V  L  L  R  I  D  D  I  V  S  G  H  K  K  K  G  D  D  Q  N  R  Q

ACTGGTGCTCCAGATGCTGGCCAGGAGTGCTGAGCACGTTGAGGGCAGCCCCAGTCTGTCCCATCTCAGTTTGCAAAAGCACT
 T  G  A  P  D  A  G  Q  E  .

TTCCAGGAACACTGTGGACATCTTTGTTTGCGAAGGATCAGGTTGAGGGGCTTCCAATGATTAAATCTAAGTCATTGAAAAAAAAAAAAA

GACACGTATCTCTTCTATTGTAAGCTTTCCATTTAGTTTGCTT
```

Fig. 8f.

pTdelta2 cDNA    Sequence

GGCTCTCCAGCAGCCCCTTGCTCGGCTTCCGCCCTTCTCTCCCGGCGTCGAAGGTCGTGGAGGAGGCGGTCAGGGAGACC

GTTACTCCACAGCCAAGCCCGGAATCCGTGTCCATCCGTCCTCCTGAACCCGCAGAGTCGCCATGCCGGAGAACGTAGCT
                                                                                               M P E N V A

TCCCGAAGCGGGGCGGCCCACCGCCGGGCAGCCGGGAAAAGCGCTACCAGACCCGGACAAGCCAGCCCAGATCCGCTTCAGC
S R S G A P T A G P G S R G K S A Y Q D R D K P A Q I R F S

AATATTTCCGGGCCCAAAGCGCTTGCTGATGCTATTAGAACAAGCCTTGGACCTAAAGGAATGGACAAAATGATTCAAGATGGAAAGGC
N I S A K A V A D A I R T S L G P K G M D K M I Q D D G K G

GATGTGACCATTACAAATGATGGTGCCACCATTCTGAAACAAATGCAGGTATTGCATCCAGCAGCCAGAATGCTGGTGGAATTGTCTAA
D V T I T N D G A T I L K Q M Q V L H P A A R M L V E L S K

GCTCAAGACATAGAAGCAGGAGATGGCACCACGTCGGTTGTCATCATTGCTGGCTCTCTCTTTAGACTCCTGTACCAAACTTCTGCAGAAA
A Q D I E A G D G T T S V V I I A G S L L D S C T K L L Q K

GGTATACATCCAACCATCATTCCGAGTCATTCCAGAGAAACTTGGAAAAGGGTCTTGAAATCCTTACTGACATGTCTCGACCTGTGCAA
G I H P T I I S E S F Q K A L E K G L E I L T D M S R P V Q

CTGAGCGACAGAGAAACTTGTTAAATAGCCAACTACTTCATTGAATTCAAAGGTTGTCTCAGTATTCAAGTCTACTCTCTCCAATG
L S D R E T L L N S A T T S L N S K V V S Q Y S S L L S P M

AGTGTCAATGCGGTGATGAAGTGATTGACCCAGCTACCAGTGTAGATCTTCGAGATATTAAAATAGTTAAGAAGTTGGTGGG
S V N A V M K V I D P A T S V D L R D I K I V K K L G G

ACAATAGATGACTGTGAGCTGTGGAAGGCCCTCGTTCTCACACAGAAGTAGCAAATTCTGGCATAACAGAGTTGAAAGGCTAAGATT
T I D D C E L V E G L V L T Q K V A N S G I T R V E K A K I

GGGCTTATTCAGTTTTGCTTATCTGCTCCTAAAACAGATAATGGATAATCAAATAGTAGTAGTCAAATCGACTATGCCCAGATGGATCGAGTGCTT
G L I Q F C L S A P K T D M D N Q I V V S D Y A Q M D R V L

Fig. 8g.

```
CGAGAGGAGAGAGCCTATATTTAAATTGGTGAAGCAAATTAAGAAAACAGGATGTAATGTCCTTCTCATACAGAAGTCTATCCTGAGA
 R  E  E  R  A  Y  I  L  N  L  V  K  Q  I  K  K  T  G  C  N  V  L  L  I  Q  K  S  I  L  R
GATGCCCTAGTGATCTTGCATTACATTTCTGAATAGATGAAGATTATGTGGTTAAGGACGTTGAAAGAAGAGACATTGAATTCATC
 D  A  L  S  D  L  A  L  H  F  L  N  K  M  K  I  M  V  V  K  D  V  E  R  E  D  I  E  F  I
TGTAAGACAATTGGAACCAAACCAGTTGCTCACATTGACCAGTTCACTGCTGACATGCTGGGTTCTGCTGAGTTAGCAGAGAAGTCAGT
 C  K  T  I  G  T  K  P  V  A  H  I  D  Q  F  T  A  D  M  L  G  S  A  E  L  A  E  E  V  S
TAAATGGTTCTGGAAACTATTCAAGATTACAGTTGTACAAGCCCAGGGAAAACAGTTACAATTGTCGTACGTGGTTCTAACAAACTG
 L  N  G  S  G  K  L  F  K  I  T  G  C  T  S  P  G  K  T  V  T  I  V  V  R  G  S  N  K  L
GTGATTGAAGAAGCTGAGCGCTCCATTCATGATGCTCTCTGTGTTATCCGATGCCTAGTGTCTTAGTAAAGAAAGAGCTCTTATTGCAGGAGGTGGT
 V  I  E  E  A  E  R  S  I  H  D  A  L  C  V  I  R  C  L  V  K  K  R  A  L  I  A  G  G  G
GCTCCCAGAAATAGAGCTGCCCTCAGACTGACAGAGTACTCCCGAACACTGAGTGGTATGGAGTCCTACTGTGTTCGTGCTTTCGCGGAT
 A  P  E  I  E  L  A  L  R  L  T  E  Y  S  R  T  L  S  G  M  E  S  Y  C  V  R  A  F  A  D
GCTATGGAAGTCATTCCATTCTACACTAGCTAGAAATGCTGGCCTAAGCTGAATCCCATTTCTACAGAGACTAAGAGCTAACAGACCGCCATGCCCAA
 A  M  E  V  I  P  S  T  L  A  E  N  A  G  L  N  P  I  S  T  V  T  E  L  R  N  R  H  A  Q
GGAGAAAAACTACAGGCATTAATGTCCGAAGGTGGATCCTCCAACATTTGGAGGAAATGGTGTTCAGCCTCTGTTGGTGTCAGTC
 G  E  K  T  T  G  I  N  V  R  K  G  G  I  S  N  I  L  E  E  M  V  V  Q  P  L  L  V  S  V
AGTGCTTGACCTTAGCAACTGAAACTGTGCGAGCATTGTGGCTGAATGAAGGACAACCACCTGTCCTGTCTGAAGCTTCAGAGTTTTGACAT
 S  A  L  T  L  A  T  E  T  V  R  S  I  L  K  I  D  D  V  V  N  T  R  .
TGACTGCATCATTATGGACACAGAAGTACTGTGGCTGAATGTATTGAAACAATTAATGAAAACATTAAATACTTGGTTTTAAACTCCAAAAAAAAAAAAAA
TGTCTTCCAGTTGGCATTTGTTGAAATTGTATTGAAATGTATTGAAACAATTAATGAAAACATTAAATACTTGGTTTTAAACTCCAAAAAAAAAAAAA
AAAAAAA
```

Fig. 8h.

pTepsilon5 cDNA Sequence

```
GGATTCTGCGTCCCTCGGAGAGGAGGTGCGGTGTCTCTCTCCGAGTGTCCCCGCTGTTACTGGAGGAGCCGCTCGTTCTAGT

TCGTCCACCATGGGCGTTCCGTGGGACCCTCGCCTTCGATGAGTATGGCGCCCCCTTTCTCATTATCAAGGACCAAGATGCAAGTCCCGT
          M   A   S   V   G   T   L   A   F   D   E   Y   G   R   P   F   L   I   I   K   D   Q   D   R   K   S   R

CTCATGGGCTTGAGGCCCTCAAGTCTCACATCATGGCTGCCAAGCTGTAGCAAACAACATGGACGTCACTGGACCAAACGGGCTG
 L   M   G   L   E   A   L   K   S   H   I   M   A   K   A   K   A   V   A   N   T   M   R   T   S   L   G   P   N   G   L

GACAAGATGATGGTTGATAAGGATGGCGATGTGACTATAACAAACGATGGTGCCACCATTCTAAGCATGATGGATGTTGATCATCAGATT
 D   K   M   M   V   D   K   D   G   D   V   T   I   T   N   D   G   A   T   I   L   S   M   M   D   V   D   H   Q   I

GCCAAGCTGATGGTTGAACTGTCCAAATCCCAGGATGATGAAATTGGAGATGGACCACAGGAGTGGTTGTCTTGGCTGGCCTTGTTG
 A   K   L   M   V   E   L   S   K   S   Q   D   D   E   I   G   D   G   T   T   G   V   V   L   A   G   A   L   L

GAAGAAGCTGAACAGCTGCTGGACCTGCGAGGCATTCACCCTGAGAATTGCTGATGGCTACGAGCAGGCTGCCCGAATTGCAATACAACAC
 E   E   A   E   Q   L   L   D   R   G   I   H   P   I   R   I   A   D   G   Y   E   Q   A   A   R   I   A   I   Q   H

CTGGACAAGATCAGCGACAAAGTGCTGGTAGATATCAATAATCCTGAACCTCTGATTCAGACTGCAAAAACCACGCTGGCTCCAAAGTG
 L   D   K   I   S   D   K   V   L   V   D   I   N   N   P   E   P   L   I   Q   T   A   K   T   T   L   G   S   K   V

ATTAACAGCTGTCACCGACAGATGGCTGAGATCGCCGTTGAATGCCGTCCTCACGGTGGCAGATATGGAGCGGAGAGATGTTGACTTTGAG
 I   N   S   C   H   R   Q   M   A   E   I   A   V   N   A   V   L   T   V   A   D   M   E   R   R   D   V   D   F   E

CTCATTAAAGTGGAAGGCAAAGTAGGTGGGCGTCTGGAAGACACCAAGCTCATAAAGGGTGTGATCGTGACAAGGACTTCAGCCACCCA
 L   I   K   V   E   G   K   V   G   G   R   L   E   D   T   K   L   I   K   G   V   I   V   D   K   D   F   S   H   P

CAGATGCCGAAAAAGTGGTAGATGCTAAGATTGCAATTCTCACGTGTCCATTGAGCCACCTAAACCTAAGACAAAGCACAAGCTGGAT
 Q   M   P   K   K   V   V   D   A   K   I   A   I   L   T   C   P   F   E   P   P   K   P   K   T   K   H   K   L   D
```

Fig. 8i.

```
GTCATGTCTGTGGAGGACTACAAAGCCCTGCAGAAGTACGAAAAGGAGAAGTTTGAAGAGATGATTAAGCAGATTAAAGAAACTGGTGCT
 V  M  S  V  E  D  Y  K  A  L  Q  K  Y  E  K  E  K  F  E  E  M  I  K  Q  I  K  E  T  G  A

AACCTAGCTATTTGCCAGTGGGGCTTTGACGATGAAGCCAATCACTACTCTTCAGACGGCCTGCCAGTCCGCTGGGTAGGGGGA
 N  L  A  I  C  Q  W  G  F  D  D  E  A  N  H  L  L  Q  N  G  L  P  A  V  R  W  V  G  G

CCTGAGATTGAGCTGATCGCCATTGCAACAGGAGGACGGATTGTCCCACGGTTCTCAGAGCTCACCTCTGAGAAGCTGGGCTTTGCTGGT
 P  E  I  E  L  I  A  I  A  T  G  G  R  I  V  P  R  F  S  E  L  T  S  E  K  L  G  F  A  G

GTGGTGCAGGAGATCTCCTTGGCACTACAAAGACAAAGCAAAACGATCTCCCAAGAACTGTAAGAACTCTAGAGCTGTGACCATTTCATC
 V  V  Q  E  I  S  F  G  T  T  K  D  K  M  L  V  I  E  K  C  K  N  S  R  A  V  T  I  F  I

AGAGGAGGAAACAAGATGATCATAGAAGAAGCAAAACGATCTCTCCATGATGCCCTGTGTCATCCGGAACCTCATCCGTGACAACCGT
 R  G  G  N  K  M  I  I  E  E  A  K  R  S  L  H  D  A  L  C  V  I  R  N  L  I  R  D  N  R

GTTGTGTATGGAGGGGCAGCTGAGATCAGTTGCATCCCAATGCCAGTCAGCCAAGAGGCAGACAAGTGCCCAACTTTGGAACAGTATGCC
 V  V  Y  G  G  A  A  E  I  S  C  A  L  A  V  S  Q  E  A  D  K  C  P  T  L  E  Q  Y  A

ATGAGAGCTTTTGCAGATGCCTTGGAGGTCATCCCAATGGCCCTTTCAGAAAATAGTGGCATGAATCCCATTCAGACCATGACTGAAGTT
 M  R  A  F  A  D  A  L  E  V  I  P  M  A  L  S  E  N  S  G  M  N  P  I  Q  T  M  T  E  V

CGAGCCAGACAGGTGAAGGAGAGTAACCCTGCCCTGGGGATTGACTGTTTGCACAAGGCAGTAACGATATGCAGTATCAGCATGTCATA
 R  A  R  Q  V  K  E  S  N  P  A  L  G  I  D  C  L  H  K  G  S  N  D  M  Q  Y  Q  H  V  I

GAAACCTTGATTGGCAAAAAGCAGCAGATCTCTCTTGCCACCCAGATGGTTAGGATGATTCTGAAGATTGATGACATCCGTAAGCCTGGA
 E  T  L  I  G  K  K  Q  Q  I  S  L  A  T  Q  M  V  R  M  I  L  K  I  D  D  I  R  K  P  G

GAATCTGAAGAATAAACTGTACCATTACCACTGTGACTAAATAAAGGGTGTCTGTTAAAAAAAAAAAAAAAAAAAAAAAAAAAAA
 E  S  E  E  .
```

Fig. 8j.

pTzeta12 cDNA sequence

```
GAAGACCCCGCAGAGAGCACGTTGTTCTCGGCCTCTCCCGGAGCTAGCCAGCCATGGCGGCGGTAAAGACCCTAAATCCGAAGGCCGAG
                                                 M  A  A  V  K  T  L  N  P  K  A  E

GTGGCCCGGGCCCAGGCAGCGGCTCTGGCGGTGAACATCAGCGCGCTCGGGGCCTGCAGGATGTTCTGAGGACCAACTTGGGGCCTAAGGGC
 V  A  R  A  Q  A  A  A  L  A  V  N  I  S  A  A  R  G  L  Q  D  V  L  R  T  N  L  G  P  K  G

ACCATGAAGATGCTTGTATCGGTGCTGGAGACATCAAACTTACTAAAGATGGCAATGTGCTCTTCATGAAATGCAAATTCAACACCCA
 T  M  K  M  L  V  S  G  A  G  D  I  K  L  T  K  D  G  N  V  L  L  H  E  M  Q  I  Q  H  P

ACAGCCTCTTTGATAGCAAAAGTGGCTACAGCCCAGGATGACATAACTGGGCGATGGCACTACATCCAATGTCCTCATCATCGGGGAGCTG
 T  S  L  I  A  K  V  A  T  A  Q  D  D  I  T  G  D  G  T  T  S  N  V  L  I  I  G  E  L

CTCAAACAGGGGACCTGTACATTCTGAAGGTCTTCACCCAAGAATATAACTGAAGGTTTTGAAGCGGCAAAAGAAAAGGCACTCCAA
 L  K  Q  A  D  L  Y  I  S  E  G  L  H  P  R  I  I  T  E  G  F  E  A  A  K  E  K  A  L  Q

TTTCTGAACAAGTCAAAGTAAGCAAAGAGATGGACAGAGAAACACTCATCGATGTGGCCAGGACATCTCTGCGGACTAAGTTCATGCT
 F  L  E  Q  V  K  V  S  K  E  M  D  R  E  T  L  I  D  V  A  R  T  S  L  R  T  K  V  H  A

GAACTTGCAGATGTCTGACAGAGGCTGTAGTGGACTCCATTGGCCATTAGGAAAAGGACGAGCCCATTGACCTCTTCATGGTTGAG
 E  L  A  D  V  L  T  E  A  V  V  D  S  I  L  A  I  R  K  K  D  E  P  I  D  L  F  M  V  E

ATCATGGAGATGAAGCATAAATCTGAGACAGATACAAGCTTAATCAGAGGGCTTGTTTTGGATCATGGAGCTCGGCATCCTGATATGAAG
 I  M  E  M  K  H  K  S  E  T  D  T  S  L  I  R  G  L  V  L  D  H  G  A  R  H  P  D  M  K
```

Fig. 8k.

AAGAGAGTGGAAAATGCCTACATCCTCACGTGCCAACGTGTCCTAGAGTATGAGAAAACAGAAGTGAATTCTGGTTTTTTACAAGAGT
K  R  V  E  N  A  Y  I  L  T  C  N  V  S  L  E  Y  E  K  T  E  V  N  S  G  F  F  Y  K  S

GCAGAAGAGAGAGAAAAACTAGTAAAGGCTGAAAGAAATCATTGAAGATAGAGTTAAAAAAATCATAGAGCTGAAAAAGAAAGTCTGT
A  E  E  R  E  K  L  V  K  A  E  R  K  F  I  E  D  R  V  K  K  I  I  E  L  K  K  K  V  C

GGTGACTCAGATAAAGGATTTGTCGTTATTAATCAAAAGGGGATTGACCCCTTTTCCTTAGATGCCCTTGCGAAAGAAGGATCGTAGCT
G  D  S  D  K  G  F  V  V  I  N  Q  K  G  I  D  P  F  S  L  D  A  L  A  K  E  G  I  V  A

CTGCGCGAGAGCCAAGAGGAGAAACATGGAGAGGCTCTTGCTTGTGTGGGATAGCTCTGAATTCCTTTGATGACCTGAATCCTGAC
L  R  R  A  K  R  R  N  M  E  R  L  T  L  A  C  G  G  I  A  L  N  S  F  D  D  L  N  P  D

TGTTTGGGACATGCAGGGCTTGTCTATGAGTATACACTGGGTGAGGAGAAGTTCACCTTTATTGAGAAGTGTAACAATCCCGTTCTGTC
C  L  G  H  A  G  L  V  Y  E  Y  T  L  G  E  E  K  F  T  F  I  E  K  C  N  N  P  R  S  V

ACTTTACTGGTTAAGGGACCAAATAAGCACACTGACTCAAATCAAGGATGCAATAAGAGATGGCTTGAGGCTTGTCAAAAATGCTATT
T  L  L  V  K  G  P  N  K  H  T  L  T  Q  I  K  D  A  I  R  D  G  L  R  A  V  K  N  A  I

GATGATGGCTGTGTTGTCCCAGGTGCGGGTGCAGTAGAAGTGGCACTGGCAGAAGCTCTGATTAAATACAAGCCCAGTGTGAAGGCAGG
D  D  G  C  V  V  P  G  A  G  A  V  E  V  A  L  A  E  A  L  I  K  Y  K  P  S  V  K  G  R

GCGCAGCTTGGAGTCCAGGCATTTGCAGATGCCTTGCTCATCATTCCAAGTTCTTGCGCAAACTCTGGTTTGACCTTCAGGAAACA
A  Q  L  G  V  Q  A  F  A  D  A  L  L  I  I  P  K  V  L  A  Q  N  S  G  F  D  Q  E  T

Fig. 8I.

```
TTAGTTAAGTTCAAGCTGAACATTCAGAATCGGGCCAGTCGTAGGTGTGGATCTGAGCCAGTGAGCCGATGGTGGCCGCAGAGATG
 L  V  K  V  Q  A  E  H  S  E  S  G  Q  L  V  G  V  D  L  S  T  G  E  P  M  V  A  A  E  M

GGTGTGTGGGATAACTACTGTGTGAAGAAGCAGCTGCTACACTCCTGTGATCGCCACCAACATTCTCCTGGTGACGAGATCATG
 G  V  W  D  N  Y  C  V  K  K  Q  L  L  H  S  C  T  V  I  A  T  N  I  L  L  V  D  E  I  M

CGAGCTGGAATGTCCTCTCTGAAGGGTTGAGGCCTGCCTGTGATACTACAGGATGTGGGGAATGGTTATTTTGTCCAAGCTTCAAG
 R  A  G  M  S  S  L  K  G

TGATTTGGAAAAAATTTCTCTTCCTGATTGGAGAAAAGAACGGACATTGACACCTATTCAAATTATACTGTAAATTTTATTTA

TTTTGCCCTTGAGTATCTGAAGACACTCAAAGCAGCTCTTTTCAACCCACTGAACAAGATGTTTTAGCTACACCGATACAAAATTACA

TAATAAGATAAGCATGTGTCTACCCTGTTCCATAAGTGTTCTTTGAAAGTTTGTAATGGTTTCTCCTAAATAAGGCATGGTGACACA

TGCCTGTAAGCCTAGCCCCTTGAAATAGTCCGAATTCTATGCCAACTCAGGCTACAGGAGACCCCAGGTCGAAAGAATAATTGTTG

TGGATGTATTTGAAATAATCCAGCCAACTCCCCTGTTAAACATGTAAGATCCTTGCCAGTGTAAAACACATCTGGGTAATTTATGGGTTGC

ATAATGTCTAATAAATACTTAAAGAGTGAAAAAAAAAAAAAAA
```

Fig. 8m.

pCBL80 cDNA sequence

```
AGATGATGCCCACCAGTTATCCTGTGAAAGAGGTACTGATAGTCCAGGCATCCCTCAGCTGTGAGTAACATCAGTGCTGC
 M  M  P  T  P  V  I  L  K  E  G  T  D  S  S  Q  G  I  P  Q  L  V  S  N  I  S  A  C

CAAGTGATTGCTGAGGCTGTAAGGCTGTCCCGTGGTCCCCGTGGTCATGGACAAACTTATGTGATGCCAGGCAAAGCAACAATATCT
 Q  V  I  A  E  A  V  R  T  T  L  G  P  R  G  M  D  K  L  I  V  D  G  R  G  K  A  T  I  S

AATGGGGGCCACAATTCTGAAACTCTGATGTGTCCATCCTGCAGCAAAGACTTAGTGACATAGCCAAGTCCCAGATGCTGAG
 N  D  G  A  T  I  L  K  L  L  D  V  V  H  P  A  A  K  T  L  V  D  I  A  K  S  Q  D  A  E

GTTGGTGATGGCACCACTCAGTGACCCTCAGTGTCCTGCTGCGGAGTTTCTGAAGCAGTGAAGCCCTACGTGGAAGAAGGTTACACCCTCAG
 V  G  D  G  T  T  S  V  T  L  L  A  A  E  F  L  K  Q  V  K  P  Y  V  E  E  G  L  H  P  Q

ATCATCATCCGAGCTTTCCGCACAGCTACCCAATTGGCTGTTAACAAATCAAGAGATATGACTGTGAAGAAGCAAGATAAAGTA
 I  I  I  R  A  F  R  T  A  T  Q  L  A  V  N  K  I  K  E  I  A  V  T  V  K  K  Q  D  K  V

GAGCAGAGGAAGATGCTGGAGAAGTGCGCAATGACAGCCCTGAGCTCCAGCTCCAAGCTCATCTCCCAGCAGAAGGTCTTCTTCGCCAAGATGGTG
 E  Q  R  K  M  L  E  K  C  A  M  T  A  L  S  S  K  L  I  S  Q  Q  K  V  F  F  A  K  M  V

GTTGATGCCGTGATGATGCTTGACGAGCTGCTGCAGCTTAAAATGATTGGCATCAGAAAGGTGCAGGGGAGCCCTGGAGGAGTCTCAG
 V  D  A  V  M  M  L  D  E  L  L  Q  L  K  M  I  G  I  K  K  V  Q  G  G  A  L  E  E  S  Q

CTAGTTGCTGGTGTTGCCTTCAAGAAGACTTTCTCTTATGCTGGATTTGAAATGCAGCCCAAGAAGTATAAGAACCCAAGATTGCCTC
 L  V  A  G  V  A  F  K  K  T  F  S  Y  A  G  F  E  M  Q  P  K  K  Y  K  N  P  K  I  A  L

TTAAATGTTGAGCTTGAGCTGAAAGCAGAAAAGGATAATGCTGAAATCAGAGTCCACACAGTCGAGGATTACCAGGCAATTGTTGATGCC
 L  N  V  E  L  E  L  K  A  E  K  D  N  A  E  I  R  V  H  T  V  E  D  Y  Q  A  I  V  D  A

GAGTGGAATATTCTTATGACAAGTTAGAGAAGATCCATCAGTCTGGAGCCAAGTCATCTGTCTAAACTCCTATTGGGGATGTGGCC
 E  W  N  I  L  Y  D  K  L  E  K  I  H  Q  S  G  A  K  V  I  L  S  K  L  P  I  G  D  V  A
```

Fig. 8n.

```
ACCCAGTACTTTGCTGATAGGGACAGTTCTGTGCTGCCTGAGGAGGATCTGAAGAGGACGATGATGGCTTGTGAGGCTCA
 T  Q  Y  F  A  D  R  D  M  F  C  A  G  R  V  P  E  E  D  L  K  R  T  M  M  A  C  G  G  S

ATCCAGACCAGTGTGAATGCTCTGGTTCCAGATGTGCTGGGCCACTGCCAAGTGTTTGAAGAGACCCAAATTGGAGAGAGGAGTACAAT
 I  Q  T  S  V  N  A  L  V  P  D  V  L  G  H  C  Q  -  V  F  E  E  T  Q  I  G  G  E  R  Y  N

TTCTTCACTGGCTGCCCTAAGGCACCAAGACATGTACCATCATCCCGTGTGGGCGCTGAGCAGTTTATGGAAGAGACAGAGAGTCCCTA
 F  F  T  G  C  P  K  A  K  T  C  T  I  I  L  R  G  G  A  E  Q  F  M  E  E  T  E  R  S  L

CATGATGCCATCATGATTGTGAGGAGGGCCATCAAGAATGACTCTGTGGTGGCTGGAGGCGCATATGCCAAGGCCCTGGAGATTATTCCACGACAGCTA
 H  D  A  I  M  I  V  R  R  A  I  K  N  D  S  V  V  A  G  G  A  I  E  M  E  L  S  K  Y

CTGGGGATTACTGAGGACATTCCTGGGAAGCAGCAGCTGTTGATTGGGGCTGTTGACAAGCTGCGACCAGGAGTAGTGTGGGGTGACATC
 L  R  D  Y  S  R  T  I  P  G  K  Q  Q  L  L  I  G  A  Y  A  K  A  L  E  T  I  P  R  Q  L

TGTGACAACGCTGGCTTTGATGCCACAAACATCCTCAACAAGCTCCGGGCCCATGCCCAGCAGGGCATGTGGTATGGGGTGGACATTCTGAGGCT
 C  D  N  A  G  F  D  A  T  N  I  L  N  K  L  R  A  R  H  A  Q  Q  G  M  W  Y  G  V  D  I

AACAATGAGAACATCGCCGACAACTTCCAGGCATTTGTGTGGGAGCCAGCCATGCACGTGCGAATCAACGCTCTGACAGCTTCTGAGGCT
 N  N  E  N  I  A  D  N  F  Q  A  F  V  W  E  P  A  M  H  V  R  I  N  A  L  T  A  A  S  E  A

GCATGCCTTATTGTCCGTGATGAGACTATCAAGAACCCCCGCTCCACTGTGGATCCTCCACTCAGCTGCCAGTCCAGGAGAGCC
 A  C  L  I  V  S  V  D  E  T  I  K  N  P  R  S  T  V  D  P  P  A  P  S  A  G  R  G  R  G

CAAGCCCGCTTCCACTGAGAGGCCGAGGCGGTCTGCACCTCCTGTGAGGTGAGATGAGAAGATGGTGCTGCTGCTGGTT
 Q  A  R  F  H  .

CTCACTGAGGTTATTTAAATAAAGC
```

Fig. 8o.

pTtheta1 cDNA sequence

```
CCCATTCCCAGCAGGCAGTGCGGGCCCCCTTGCTTCCTCGGCTGTCTTCCTCGGAGGAGCGGTGAGCGGTGACTGCGGCCATG
                                                                                 M

GCGCTTCACGTCCCCAAGGCCCCGGCTTGCCCAGATGGAGCCAAACATTTCTCGGATTAGAAGAGGCTGTGTATAGA
 A  L  H  V  P  K  A  P  G  F  A  Q  M  L  K  D  G  A  K  H  F  S  G  L  E  E  A  V  Y  R

AATATACAGGCCTGCAAGGAGCTTGCTCAGACTACTCGCACAGCTTACGGACCAAATGAATAAAATGTCATCATCGCCTGAG
 N  I  Q  A  C  K  E  L  A  Q  T  T  R  T  A  Y  G  P  N  G  H  N  K  M  V  I  N  R  L  E

AAGTTGTTTGTGACAAACGATGCAGCGACTATTTTAAGAGAGCTAGAAGTGCAGCATCCTGCTGCAAGATGATAGTGATGCCTCTCAT
 K  L  F  V  T  N  D  A  A  T  I  L  R  E  L  E  V  Q  H  P  A  A  K  M  I  V  M  A  S  H

ATGCAAGAACAAGAGGTTGGTGATGGCACAAACTTCGTTCTGGTTTTCGCTGGGGCTTCTTGAACTAGCTGAAGAACTTCTGAGGATT
 M  Q  E  Q  E  V  G  D  G  T  N  F  V  L  V  F  A  G  A  L  L  E  L  A  E  E  L  L  R  I

GGCCTGTCAGTATCAGAGTGTTGATGAAGTGTCTCTCTCTTGAATATCGGGTATGAATAGCTTGCAAAAAGCTCATGAGATCCTCTGAGTTGTATGTGTTCTGCC
 G  L  S  V  S  E  V  I  S  G  Y  E  I  A  C  K  K  A  H  E  I  L  P  E  L  V  C  C  S  A

AAAAACCTTCGAGATGTTGATGAAGTGTCTCTCCATCTTTCCTGATTCTGGCAATTTCAATGTTGATAACATCAGAGTATGTAAGATTCTGGCTCTGGT
 K  N  L  R  D  V  D  E  V  S  S  L  L  R  T  S  I  M  S  K  Q  Y  G  S  E  T  F  L  A  K

CTTATTGCTCAGGCTTGTGTTCTATCTTTCCTGATTCTGGCAATTTCTGTTTAAGAAGAAACTGAAGGTGATGTGACATCTGTCAAAGATGCAAAGATAGCTGTG
 L  I  A  Q  A  C  V  S  I  F  P  D  S  G  N  F  N  V  D  N  I  R  V  C  K  I  L  G  S  G

ATTTATTCATCCTCAGTATTACATGGCATGGTTTTAAGAAGAAACTGAAGGTGATGTGACATCTGTCAAAGATGCAAAGATAGCTGTG
 I  Y  S  S  S  V  L  H  G  M  V  F  K  K  E  T  E  G  D  V  T  S  V  K  D  A  K  I  A  V

TACTCTGTCCGTTTGATGGCATGATAACAGAGACAAAGGGACCTGCTGATTAAGACTGCCGAGAGCTAATGAACTTCAGTAAGGGA
 Y  S  C  P  F  F  D  G  M  I  T  E  T  K  G  T  V  L  I  K  T  A  E  E  L  M  N  F  S  K  G
```

Fig. 8p.

GAGGAGAACCTCATGGATGCTCAGGTGAAGGCCATTGCAGGCACTGGTGCAAATGTCATAGTAACAGGGGGCAAAGTGGCGGACATAGCT
E  E  N  L  M  D  A  Q  V  K  A  I  A  G  T  G  A  N  V  I  V  T  G  G  K  V  A  D  I  A

CTTCATTATGCTAACAAGTACAATATCATGTTGAGACTGAACTCAAAGTGGGATCTCAGAGACTCTGTAAACAGTTGGTGCCACA
L  H  Y  A  N  K  Y  N  I  M  L  V  R  L  N  S  K  W  D  L  R  R  L  C  K  T  V  G  A  T

GCTCTTCCAAAATTGACTCCTCCCGTCCAAGAGAATGGGACATTGTGACAGTGTTACCTCTCAGAAGTGGAGATACACAAGTGGTT
A  L  P  K  L  T  P  P  V  Q  E  E  M  G  H  C  D  S  V  Y  L  S  E  V  G  D  T  Q  V  V

GTTTTTAAGCATGAAAAGAAGATGGTGCCATTTCTACTATAGTTCTTGAGGTTCTACAGACAATCTGATGATGACATAGAAAGGCA
V  F  K  H  E  K  E  D  G  A  I  S  T  I  V  L  R  G  S  T  D  N  L  M  D  D  I  E  R  A

GTAGATGATGGAGTTAATACTTTCAAAGTTCTCACAAGGATAAGCGTCTGTACCTGAGGTGAGCTACCGCAAATTGAATTGGCTAAA
V  D  D  G  V  N  T  F  K  V  L  T  R  D  K  R  L  V  P  G  G  G  A  T  E  I  E  L  A  K

CAAATCACATCATGAGAGACGTGTCCTGGGCTTGAACAGTATGCTATTAAGAAGTTGCTGAAGCGTTGAAGCGATTCCACGGGCA
Q  I  T  S  Y  G  E  T  C  P  G  L  E  Q  Y  A  I  K  K  F  A  E  F  E  I  P  R  A

CTGGGCAGAAATTCTGGCGTGAAGGCCAATGAAGTTATCTCTAAACTTTATTCCGTACACCAAGGAGAAACAAAATGTGGGGTTGGAT
L  A  E  N  S  G  V  K  A  N  E  V  I  S  K  L  Y  S  V  H  Q  E  G  N  K  N  V  G  L  D

ATCGAGGCTGAAGTCCCTGCTGTAAAGGATATGTTAGAAGCCAGTATTTTAGATACTTACTTGGGAAAATACTGGGCTATTAAACTGGCC
I  E  A  E  V  P  A  V  K  D  M  L  E  A  S  I  L  D  T  Y  L  G  K  Y  W  A  I  K  L  A

ACTAATGCTGCAGTCACTGTACTAAGAGTGGATCAGATCATCATGGCCAAACCAGCTGGTGGGCCAAGCCCAAGTTGGGAAGAAGAC
T  N  A  A  V  T  V  L  R  V  D  Q  I  I  M  A  K  P  A  G  G  P  K  P  P  S  G  K  K  D

TGGGATGACGACCAGAATGACTGAGGAACTTGTCATAGTTAAGAGTTGTGTTTGTAGAGTAGAACTTGCCCAGTGTTTATTTTCTTA
W  D  D  D  Q  N  D  .

TTTGTGTTGTACTCTGCTGGTGGTACAATAAATGTGTACTGTTAAAAAAAA

Fig. 8q.

FOLDING PROTEIN COMPLEXES

CROSS REFERENCE TO RELATED APPLICATIONS

This application is filed under 35 U.S.C. §371 from PCTGB95/00192 filed Jan. 31, 1995.

The present invention relates to the folding of proteins. In particular, the present invention provides proteins, which are able to form a complex in vitro, useful in facilitating folding of proteins, for example those produced using recombinant DNA technology. Genes encoding the proteins of the complex are also provided. The present invention further relates to methods of assembling a protein complex able to fold proteins in an in vitro environment.

Molecular chaperones are known to be able to assist in the folding of proteins along the folding pathways from denatured state to correctly folded product (reviewed in [1]). One well studied class of molecular chaperones are the chaperonins (GroEL, Hsp60 and Rubisco subunit binding protein) found in eubacteria, mitochondria and plastids (reviewed in [2,3]). They are 14-mer double-torus structures composed of one (GroEL and Hsp60) or two (Rubisco subunit binding protein) subunit types and show seven-fold symmetry [4,5]. In vitro these chaperonins bind denatured proteins and upon ATP hydrolysis, release them into aqueous solution where they complete folding [6]. In vivo there is evidence that they are involved in the folding, transport and assembly of newly synthesized proteins. The original mutations isolated in groE affected the folding of bacteriophage particle subunits [7] but more recent genetic analysis suggests a more general role in protein biogenesis in *E. coli* [8]. HSD60 is involved in the import of proteins into the mitochondrial lumen from the cytoplasm [9].

Although no GroEL-like chaperonins have been identified in eukaryotic cytosol, the double-torus TCP-1-containing particle seems to be a component of the eukaryotic folding machinery and may play an analogous role to that of GroEL in eubacteria and the GroEL related chaperonins in symbiotic organelles. TCP-1 is weakly related to the GroEL family [10] but shows nearly 40% identity to an archaebacterial chaperonin, TF55 [11]. It has been proposed that GroEL and TCP-1 are subfamilies derived from a primordial gene [10,12,13,14] and it has been suggested that the eukaryotic TCP-1-containing chaperonin may have evolved from an archaebacterial lineage [3,11].

Recently, purified chaperonin containing TCP-1 has been shown to facilitate the folding of actin [15] and tubulin [16,17] in vitro and it binds newly-synthesized actin, tubulin and some other unidentified polypeptides in vivo [18]. One striking difference between the bacterially derived chaperonins and the TCP-1-containing chaperonin is the heteromeric nature of the TCP-1-containing particle [14,15,17,19]. There are at least five polypeptide species in the complex containing TCP-1 [14,17].

To date, little sequence information has been available on the polypeptides which make up the complex, despite the fact that various parties have obtained the sequences of peptides from a number of polypeptides of TCP complexes of different organisms. Frydman et al (17) demonstrated the presence of six subunits in bovine TCP complex, which they termed "TRiC" (TCP-1 ring complex), and obtained some peptide sequence information indicating some resemblance both between polypeptides of the complex and between these polypeptides and those of other organisms. Rommelaere et al [59] looked at the cytosolic chaperonin from both rabbit reticulocyte lysate and bovine testis. They report finding eight different polypeptides in rabbit reticulocyte chaperonin, and obtaining partial amino acid sequences of all eight.

However, full length clones have proved elusive. The full sequence of murine TCP-1 has been available since 1986 (20) and Ehmann et: al (FEBS, 336: 2, 313–316, 1993) have reported the obtention of a TCP-1 related sequence from *Avena sativa* (oat) seedlings. Despite this information being available, there has yet to be a report of the obtention of full-length nucleic acid sequences encoding the components of a mammalian TCP-1 complex. Knowledge of short peptide sequences derived from individual subunits of chaperonin containing TCP-1 has not enabled the specific cloning of the full-length cDNA for individual subunits. One problem is that in order to be sure a peptide sequence is derived from a subunit of the family, it must be identifiably homologous to the only full-length mammalian sequence available, ie TCP-1 (20,48). Any DNA sequences derived by reverse translation from the novel peptide sequence will also be related to TCP-1 and the related gene sequences. If these sequences are used as PCR primers they will prime synthesis and amplification of many TCP-1 related sequences, so further insight and activity are needed to identify the sequences which encode particular subunits of the complex.

The present invention provides individually seven nucleic acid molecules with sequences encoding subunits of the TCP-1-containing chaperonin, different from the original Tcp-1 gene (reported in 20). Since, in mice, at least three of the novel Tcp-1 related genes are unlinked to the mouse t complex, it is proposed to rename the TCP-1 complex [14] as CCT, chaperonin containing TCP-1. Only now we have all the eight complete sequences of the ubiquitously expressed subunits is it possible to know the gene and subunit to which each PCR product corresponds. Likewise, all other TCP-1 related genes in the databases make no sense without the complete sequences being available.

The present invention also provides molecules which are mutants, derivatives or alleles of any one of the seven sequences provided, particularly mutants, derivatives and alleles which encode a protein which retains a functional characteristic of the protein encoded by the respective wild-type gene, especially the ability to associate with at least another subunit to form a complex able to fold a polypeptide. Changes to a sequence, to produce a mutant or derivative, may be by one or more of insertion, deletion or substitution of one or more nucleotides in the nucleic acid, leading to the insertion, deletion or substitution of one or more amino acids. Of course, changes to the nucleic acid which make no difference to the encoded amino acid sequence are included. We have demonstrated the existence of the 8 gene sequences in yeast and in plants by hybridization (52, unpublished results) and 6 genes have been isolated from yeast by ourselves and others (53). These 6 yeast genes correspond exactly (ie. they are the orthologues of) to six of the genes exemplified in this application CCTα, β, γ, δ, ε, η and ζ. We predict that all eukaryotic organisms contain at least the set of eight genes which we have described in mouse. There may be tissue specific CCT genes or additional CCT genes in some organisms but we would expect each of these to be closely related (greater than 70% amino acid sequence homology) to one of the eight genes described here. These eight CCT genes of mouse constitute the basic family which comprise the core CCT complex. In a preferred embodiment of the present invention, the sequence is one encoding a polypeptide found in a human or a mouse.

The polypeptides may have an amino acid sequence which shares a significant degree of homology with any of the specific sequences provided herein. Such homology may for example, be 60% or greater, 70% or greater, 80% or greater, 90% or greater or 95% or greater, provided the polypeptide is able to function as a subunit of a complex able to fold a polypeptide The sequences of polypeptides encoded by nucleic acid according to each of seven different embodiments of the present invention are provided in FIGS. 3(a) to (f) and FIG. 8(h) Preferred nucleic acid sequences are shown in FIGS. 8(b) to (h). The present invention also provides a vector which comprises nucleic acid with any one of the provided sequences, preferably a vector from which polypeptide encoded by the nucleic acid sequence can be expressed. The invention further encompasses a host cell transfected with such a vector. The host cell may be bacterial or eukaryotic, such as yeast or mammalian e.g. murine.

According to another aspect of the present invention there is provided a method of making a polypeptide component (subunit) of a complex, which complex is-able to fold a polypeptide, which-method comprises expressing the polypeptide component from encoding nucleic acid, the component being other than TCP-1. (A nucleic acid sequence encoding TCP-1 is shown in FIG. 8(a).) Preferably the nucleic acid is one with a sequence shown in FIG. 8 or a mutant, derivative or allele of such a sequence. Appropriate cofactors or accessory materials may be needed in order for the complex to function in some circumstances. Indeed, specificity of the complex for folding different polypeptides may be altered according to which cofactors are present and/or what combination of polypeptide components ("subunits") is used.

The present invention also provides a polypeptide component of a complex able to fold a polypeptide, the polypeptide being substantially free of other polypeptides or substantially free of other polypeptides of the complex, and being other than TCP-1. Preferably, the polypeptide component, or a mutant or derivative thereof can be found in a mammal, most preferably in, a mouse or a human. In a preferred embodiment of the present invention the polypeptide is one which has any one of the amino acid sequences shown in FIGS. 8(b) to (h) (see also FIG. 3). Modified polypeptides (eg mutants or derivatives) which have the ability to form a complex able to fold a polypeptide are encompassed by the present invention.

The provision for the very first time of full-length sequences of nucleic acid molecules which encode polypeptides of a complex able to fold a polypeptide enables the production of such a complex using recombinant techniques. According to another aspect of the present invention there is provided a method of producing a complex able (under appropriate conditions) to fold a polypeptide, the method comprising expressing polypeptide components of the complex from encoding nucleic acid and causing or allowing assembly of the polypeptide components into the complex. Preferably at least some of the components are murine or human. Preferably a polypeptide component of the complex is any one of those shown in FIGS. 8(a) to (h), or a mutant or derivative thereof. Polypeptide components of the complex may be expressed individually and then purified, with the assembly carried out in vitro by mixing CCT subunits in the appropriate combinations. On the other hand, subunits may be expressed together.

Also provided by the present invention is a complex able to fold a polypeptide, the complex having been produced using recombinant DNA technology. The use of recombinant DNA technology in the production of a complex enables an intelligent selection to be made about which subunits to include, in those cases where not all of those provided are not required, and the easy assembly and purification of complexes with the required biological activity. This is facilitated still further by the provision of subunit specific antibodies, discussed below. The functional test for a useful complex is its ability to fold a polypeptide. Results shown below indicate that different combinations of subunits exist in vivo. Immunoprecipitation experiments may be used to determine subunit combinations in purified complexes. Furthermore, recombinant production of different combinations of subunits and in vitro testing of ability to bind substrate polypeptide (eg in a reticulolysate system) or ability to fold polypeptide (eg in an E. coli expression system or in a separate combination stage following earlier production of the subunits) enables easy determination of subunit combinations which are functional.

The present invention also encompasses the use of a complex in the folding of a polypeptide. Generally the complex will be one produced using recombinant DNA technology. As discussed, the complex may consist of all or less than all of the subunits provided herein. Similarly, the invention provides a method of folding a polypeptide which comprises causing or allowing such-a complex to fold the polypeptide, following a previous step of production of the complex. In fact, it may be that the complex is produced at the same time as the polypeptide to be folded, e.g. by expression from the same vector and/or expression in the same host cell, rather than in a previous step.

The provision by the present invention of the full-length sequences of the subunits of a folding complex enables the production of subunits individually, with subsequent purification and combining to form a complex, the production of subunits together with combination of subunits taking place in the host cell culture (e.g. E. coli, yeast or Baculovirus systems) and with subsequent purification, or the expression of combinations of subunits with substrate in a host cell system (e.g. E. coli, yeast or Baculovirus systems), thus constructing a folding factory in vivo.

Until now, it has proved problematic to obtain antibodies which are specific for an individual subunit from the complex, in the sense of distinguishing between one subunit and the others. The reasons For this are apparent: the subunits share (varying degrees of) homology with one another. Accordingly, attempts to obtain subunit specific antibodies have failed. Immunisation of an animal with a purified subunit causes the production of antibodies which, in the most part, are cross-reactive with a number of subunits. Now that the present application has provided the full sequences of the subunits for the first time, it has proven possible to identify regions of the subunits which are sufficiently different from corresponding regions in the other subunits to enable the production of subunit specific antibodies.

Thus, according to another aspect of the present invention there is provided an antibody specific for a CCT subunit (subunit of a complex able to fold a protein) other than TCP-1 (CCTα), preferably a mammalian subunit, such as human or murine. In a preferred embodiment, the antibody is specific for an epitope of a peptide corresponding to a C-terminal portion of a subunit, or a variant of such a peptide (modified by any of insertion, substitution or deletion of one or more amino acids). Most preferred peptides for this purpose are as follows:

| | | |
|---|---|---|
| APRKRVPDHHPC | (CCTbeta) | SEQ ID NO:1 |
| NRQTGAPDAGQE | (CCTgamma) | SEQ ID NO:2 |
| SILKIDDVVNTR | (CCTdelta) | SEQ ID NO:3 |
| IDDIRKPGESEE | (CCTepsilon) | SEQ ID NO:4 |
| SAGRGRGQARFH | (CCTeta) | SEQ ID NO:5 |
| SGKKDWDDDQND | (CCTtheta) | SEQ ID NO:6 |
| EIMRAGMSSLKG | (CCTzeta) | SEQ ID NC:7 |

These peptides (including an,, variant modified in any way, provided the subunit specific nature of an antibody raised to the variant is retained) each represent an aspect of the present invention.

According to a further aspect of the invention there is provided a method of obtaining an antibody specific for a CCT subunit, other than TCP-1 (CCTα), which method comprises immunising a mammal (e.g. mouse, rat, rabbit, horse, goat, sheep or monkey) with a peptide of the subunit. Preferably, the peptide is one of those listed above, or a peptide which is a variant of one of those listed, provided subunit specificity of an antibody which binds the peptide variant is retained. Antibodies may be obtained from immunised animals using a variety of techniques known in the arts and screened, preferably using binding of antibody to antigen of interest (one of the C-terminal peptides, for example). For instance, Western blotting techniques or immunoprecipitation may be used (Armitage et al (1992) Nature 357: 80–82).

As an alternative or supplement to immunising a mammal with a peptide, an antibody specific for a subunit may be obtained from a recombinantly produced library of expressed immunoglobulin variable domains, e.g. using lambda bacteriophage or filamentous bacteriophage which display functional immunoglobulin binding domains on their surfaces; for instance see WO92/01047. The library may be "naïve", that is constricted from sequences obtained from an organism which has not been immunised with any of the peptides, or may be one constructed using sequences obtained from an organism which has been exposed to the peptide or peptides of interest.

Antibodies according to the present invention may be modified in a number of ways. Indeed the term "antibody" should be construed as covering any binding member having a binding domain with the required specificity. Thus the invention covers antibody fragments, derivatives, functional equivalents and homologues of antibodies.

Example antibody fragments, capable of binding an antigen or other binding partner are the Fab fragment consisting of the VL, VH, Cl and CH1 domains; the Fd fragment consisting of the VH and CH1 domains; the Fv fragment consisting of the VL and VH domains of a single arm of an antibody; the dab fragment which consists of a VH domain; isolated CDR regions and F(ab')2 fragments, a bivalent fragment comprising two Fab fragments linked by a disulphide bridge at the hinge region. Single chain Fv fragments are also included.

A derivative is a substance derived from a polypeptide or antibody. The derivative may differ from a polypeptide from which it is derived by the addition, deletion, substitution or insertion of one or more amino acids, or the linkage or fusion of other molecules to the polypeptide. Changes such as addition, deletion, substitution or Insertion may be made at the nucleotide or protein level.

A hybridoma producing a monoclonal antibody according to the present invention may be subject to genetic mutation or other changes. It will further be understood by those skilled in the art that a monoclonal antibody can be subjected to the techniques of recombinant DNA technology to produce other antibodies or chimeric molecules which retain the specificity of the original antibody. Such techniques may involve introducing DNA encoding the immunoglobulin variable region, or the complementarity determining regions (CDRs), of an antibody to the constant regions, or constant regions plus framework regions, of a different immunoglobulin. See, for instance, EP184187A, GB 2188638A or EP-A-0239400. Cloning and expression of chimeric antibodies are described in EP-A-0120694 and EP-A-0125023.

The peptides for use in obtaining antibodies may be made by any of a variety of techniques known to those skilled in the art. For instance, this may be by solid phase synthesis (Merrifield, JACS 85: 2159–2154 (1963)) or by techniques described in Bodanszky et al, *Peptide Synthesis,* second edition (Wiley, 1976). Standard solution peptide synthesis methodologies, using chemical or enzymatic methods of amide bond formation may be employed. Commercial peptide synthesizing machines are available.

Conveniently, an amino terminal cysteine can be added to the chosen peptide in order that the peptide can be coupled to PPD through the cysteine using standard chemistry.

Systems for cloning and expression of a polypeptide in a variety of different host cells are well known. Suitable host cells include bacteria, mammalian cells, yeast and baculovirus systems. Mammalian cell lines available in the art for expression of a heterologous polypeptide include Chinese hamster ovary cells, HeLa cells, baby hamster kidney cells and many others. A common, preferred bacterial host is *E. coli.*

Suitable vectors can be chosen or constructed, containing appropriate regulatory sequences, including promoter sequences, terminator fragments, polyadenylation sequences, enhancer sequences, marker genes and other sequences as appropriate. For further details see, for example, *Molecular Cloning: a Laboratory Manual:* 2nd edition, Sambrook et al, 1989, Cold Spring Harbor Laboratory Press. Transformation procedures depend on the host used, but are well known.

Baculovirus expression systems are commercially available in kit form, eg MaxBac™. The techniques employed are described in Summers and Smith, Texas *Agricultural Experiment Station Bulletin* 1555 (1987). See also *The Molecular Biology of Baculoviruses* (ed Doerfler, 1986) for a general overview of Baculovirus. Baculovirus expression vectors have been developed for infection into a number of cell-types, including those from *Aedes aegypti, Autograph californica, Bombyx mori, Drosophila melanogaster, Spodoptera frugiperda* and trichoplusia ni.

Embodiments of the present invention are now described further by way of illustration, with reference to the figures identified below. All documents mentioned in the text are hereby incorporated by reference.

FIG. 1 shows one- and Two-dimensional gel electrophoresis of mouse CCT and bovine TRiC. (a) SDS-PAGE analysis (8% gel) of mouse testis CCT. TCP-1-containing particles purified by sucrose gradient fractionation followed by ATP-affinity column chromatography from mouse testis [14] were electrophoresed. (b–c) 2D-PAGE analysis of mouse CCT (same sample as FIG. 1*a*) and bovine TRiC [17] (kind gift of F. -U. Hartl). Subunits of TCP-1-containing particles purified by sucrose gradient fractionation followed by ATP-affinity column chromatography from mouse testis (b) and bovine testis (c) were separated by IEF followed by SDS-PAGE. (d) 2D-NEPHGE analysis of bovine TRiC. Subunits of bovine TRiC were separated by NEPHGE followed by SDS-PAGE. (e) 2D-NEPHGE analysis of antibody-affinity purified CCT. TCP-1-containing particles were purified from $^{35}$S-labelled F9 cell extracts using monospecific monoclonal antibodies to TCP-1. Proteins were visualized by silver staining (a–c), Coomassie staining (d) or autoradiography (e). Arrowhead indicates a 45 kDa protein of pI 6.5 which co-purified with F9 cell CCT. Arrows show Hsp70 proteins. (f) Molecular weights and pI values of the polypeptides comprising mouse CCT and bovine TRiC. These values are determined from 2D-gel analysis with both pI and molecular weight markers.

FIG. 2 shows an alignment of peptide sequences deduced from 5'-end DNA sequences of 16 Tcp-1 related genes (SEQ ID NO's:8–23). Clone names are used except for Tcp-1 genes of mouse, human and yeast in this figure. Letters in parentheses indicate the source species: M, *Mus musculus* (mouse); H, *Homo sapiens* (human); C. *Caenorhabditis elegans* (nematode); S, *Saccharomyces cerevisiae* (yeast). Sources of the nucleotide sequences are as follows: mouse Tcp-1 [20,48]; human Tcp-1 [48]; yeast Tcp-1 [27]; 4950 [28]; pG1–pG4 (partial 5'-end sequences) [22] and this report; p383 and p384 (partial 5'-end sequences), pTβ2, pTγ7, pTδ2, pTε5, pTζ12 and pCBL80 , this report. Although three additional human Tcp-1 related partial DNA sequences, pAP3 (A. Malik et al., manuscript in preparation), HTR3 [41] and IB713 [49] are known, these sequences are not added to this figure due to absence of 5'-end sequences (pAP3 and HTR3) or inaccuracy of sequence (IB713). However, judging by DNA sequence homology, IB713, pAP3 and pHTR3 are members of groups 2, 5 and 6, respectively.

FIG. 3 shows amino-acid sequences of β, γ, δ, ε, ζ and η subunits of mouse CCT. Amino-acid sequences of mouse CCTβ (a) (SEQ ID NO:25), CCTγ (b) (SEQ ID NO:26) CCTδ (c) (SEQ ID NO:27), CCTε (d) (SEQ ID NO:28), CCTζ (e) (SEQ ID NO:29) and CCTη (f) (SEQ ID NO:30) deduced from nucleotide sequences of cDNA clones pTβ2, pTγ7, pTδ2, pTε5, pTζ12 and pCBL80 respectively. Sequences of tryptic peptides derived from B1–B4 of mouse CCT (FIG. 1a) are shown by bold underlining. Thin underlines indicate amino acids identical to those of bovine P1–P3 and P5 ([17] and FIG. 1) determined from tryptic polypeptides of the TRiC subunits ([17], and unpublished results of F. U. Hartl et al.). An amino-acid position not determined by peptide sequencing is indicated by an 'x'. A bovine tryptic peptide sequence, P5/T36, contains 3 amino-acid differences compared to the mouse sequence and these are shown underneath.

Figure 4B:
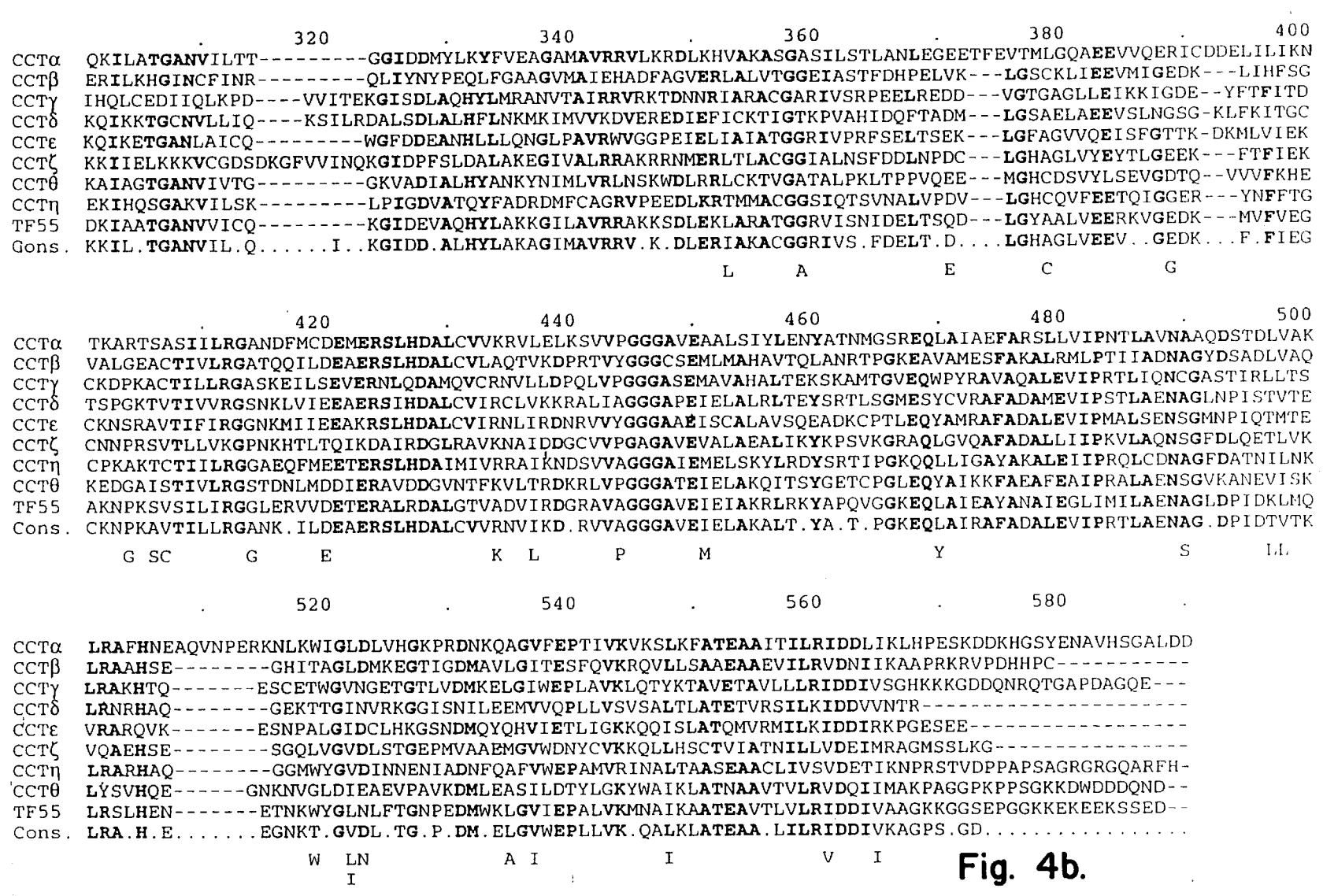

FIGS. 4A and 4B show alignment of amino acid sequences of eight mouse CCT subunits (SEQ ID NOs:24–31) and the homo-oligomeric archaebacterial chaperone TF55. A dash indicates an amino-acid gap. Conserved amino acids are indicated by bold characters. Consensus amino acids of these proteins are shown under the alignment (SEQ ID NO:33). The amino acid sequence of CCTθ is SEQ ID NO:31). The amino-acid sequences of mouse CCTα (TCP-1) [20,48] (SEQ ID NO:24) and archaebacterial chaperone TF55 of *Sulfolobus shibatae* [11] (SEQ ID NO:32) are derived from previous publications.

FIG. 5 shows comparison between a consensus motif of CCT subunits and the ATP binding motif of cAMP dependent kinase and other kinases in this family. Amino-acid sequences around a consensus motif of CCT subunits (positions 102–115 in FIG. 4) and the ATP binding motif of cAMP dependent kinase and related kinases [25,26] are compared. Amino acids conserved between these two groups are indicated by bold characters. (CCTα-SEQ ID NO:34, CCTβ-SEQ ID NO:35, CCTγ-SEQ ID NO:36, CCTδ-SEQ ID NO:37, CCTε-SEQ ID NO:38, CCTζ-SEQ ID NO:39, CCTη-SEQ ID NO:40, CCTθ-SEQ ID NO:41) cAPK-α, cyclic-AMP-dependent kinase α, (SEQ ID NO:42); PKC-α, protein,kinase c-α (SEQ ID NO:43); CaMII-α, bovine calcium-calmodulin-dependent kinase type IIα, (SEQ ID NO:44) SNF1, a budding-yeast wild-type gene product for sucrose non-fermenting mutant (SEQ ID NO:45); cdc2$^+$, a fission-yeast cell-division-cycle gene product (SEQ ID NO:46); CDC7, a budding-yeast cell-division-cycle gene product (SEQ ID NO:47); Raf, a human cellular homologue of-murine sarcoma virus product (SEQ ID NO:48); Src, a human cellular homologue of Rous avian sarcoma virus product (SEQ ID NO:49); Abl, a human cellular homologue of murine leukaemia virus product (SEQ ID NO:50); EGFR, human epidermal growth factor receptor (SEQ ID NO:51); INSR, human insulin receptor (SEQ ID NO:52); PDGFR, mouse platelet-derived growth factor receptor (SEQ ID NO:53).

FIG. 6 shows hybridization analysis of the Cct genes of mouse and yeast. (a) Southern analysis of mouse Cct genes. Mouse 129/Sv liver DNA (10 μg/lane) was digested with HindIII, electrophoresed on a 0.7% agarose gel and blotted onto a nylon membrane. The membrane was cut into 7 pieces and each of them hybridized with $^{32}$p-labelled mouse Ccta/Tcp-1 (clone nT1b11) [33], Cctb (pTβ2), Cctg (pTγ7), Cctd (pTδ2), Ccte (PTε5), Cctz (pTζ12) and Ccth (pCBL80) 1.5 kb cDNA probes. These membranes were washed in 0.1×SSC supplemented with 0.1% SDS at 65° C. (b) Southern analysis for yeast homologues of Cct genes with mouse CDNA probes. *Saccharomyces cerevisiae* DNA (1.5 μg/lane) was digested with PstI. The DNA was electrophoresed, blotted and hybridized as described in panel (a). After the hybridization, these membranes were washed in 2×SSC supplemented with 0.1% SDS at 58.5° C. Positions of molecular weight markers are shown on the left side of each panel.

FIG. 7 shows the evolutionary tree of CCT subunits of eukaryotes and the homo-oligomeric chaperonin of the archaebacterium *Sulfolobus shibatae*, TF55. An evolutionary tree based on amino acid substitutions is constructed by the neighbour-joining method [50] with the aligned amino-acid sequences numbers 18–67, 70–157, 169–200, 213–241, 251–272, 274–310, 326–372, 376–388, 398–505 and 521–566 (472 amino acids for each subunit) of mouse CCT subunits and archaebacterial chaperone TF55 in FIG. 4, and corresponding amino acid sequences of other homologues. Amino-acid sequences of human [48], fruit fly [51], plant [29] and yeast [27] homologues of CCTα/TCP-1 were derived from previous publications. The amino-acid sequence of the yeast homologue of CCTβ was obtained from Miklos et al. [28]. Capitals in parentheses indicate source species: MM, *Mus musculus* (mouse); HS, *Homo sapiens* (human); DM, *Drosophila melanogaster* (fruit fly); CE, *Caenorhabditis elegans* (nematode); AT, *Arabidopsis thaliana* (plant); SC, *Saccharomyces cerevisiae* (yeast); SS, *Sulfobus shibatae* (archaebacterium).

Figure 8D:
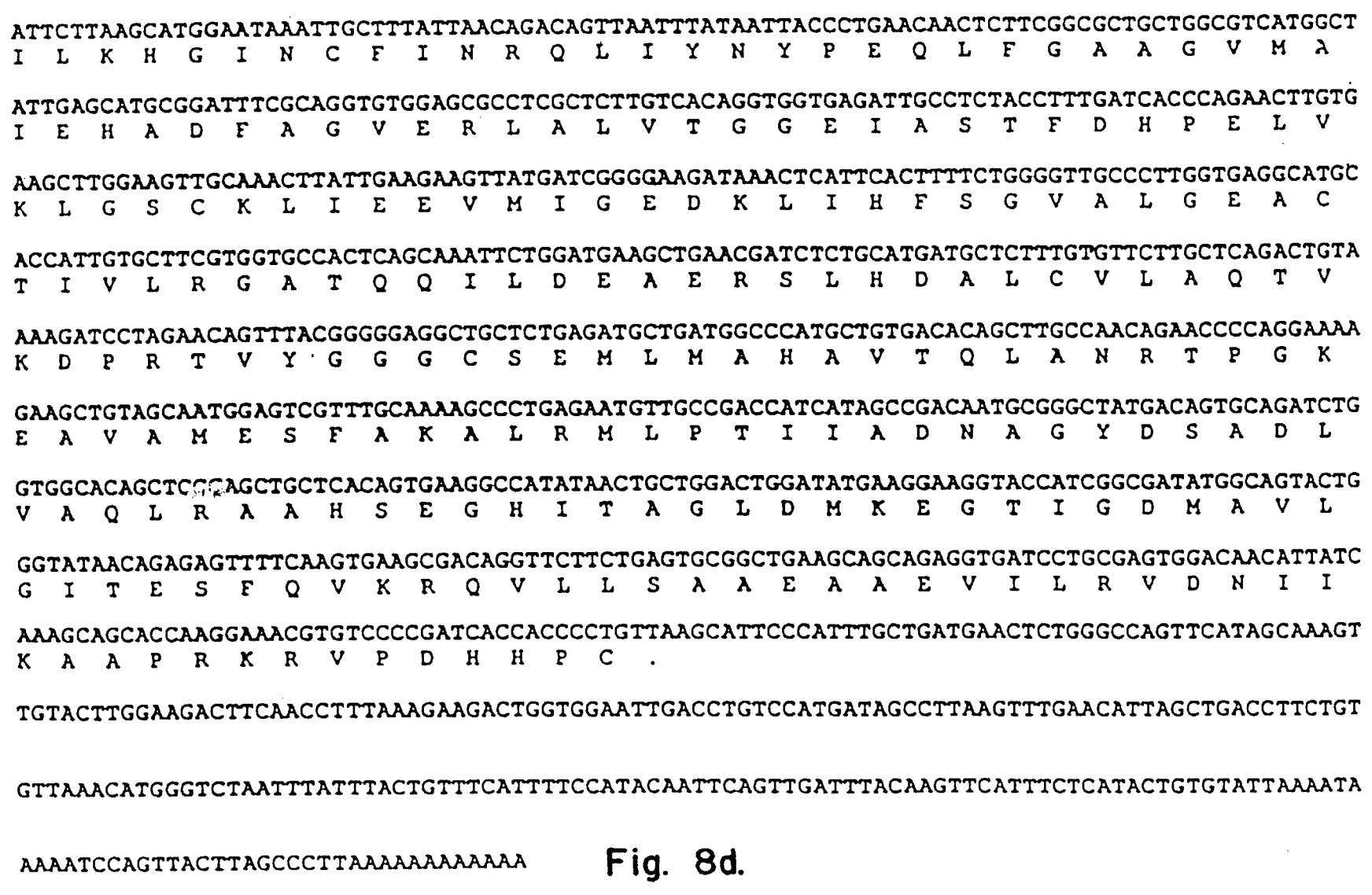

FIG. 8 shows full nucleotide sequences encoding subunits of a complex, in this case mouse CCT cDNAs. The polypeptide sequences of the predicted open reading frames are given under each DNA sequence. FIG. 8(*a*) is the sequence of Tcp-1a/Ccta (nucleotide=SEQ ID NO:54; amino acid=

SEQ ID NO:24). FIGS. 8(b) (nucleotide=SEQ ID NO:55; amino acid=SEQ ID NO:25), (c) (nucleotide=SEQ ID NO:56; amino acid=SEQ ID NO:26), (d) (nucleotide=SEQ ID NO:57; amino acid=SEQ ID NO:27) (e) (nucleotide=SEQ ID NO:58; amino acid=SEQ ID NO:28), (f), (nucleotide=SEQ ID NO:59; amino acid=SEQ ID NO:29), (g) (nucleotide=SEQ ID NO:60; amino acid=SEQ ID NO:30) and (h) (nucleotide=SEQ ID NO:61; amino acid= SEQ ID NO:31) are the sequences of the Cctb, Cctg, Cctd, Ccte, Cctz, Ccth and Cctq genes respectively.

FIG. 9 shows immunoprecipitation of CCT complexes from mouse F9 cells, precipitated under native conditions (14) using anti-peptide antibodies specific to CCTβ, CCTγ, CCTε and CCTη. A negative control shows absence of signal using an anti-peptide antibody to *Schizosaccharomyces pombe* CCTα, which does not recognise any mammalian subunits.

Figure 10:
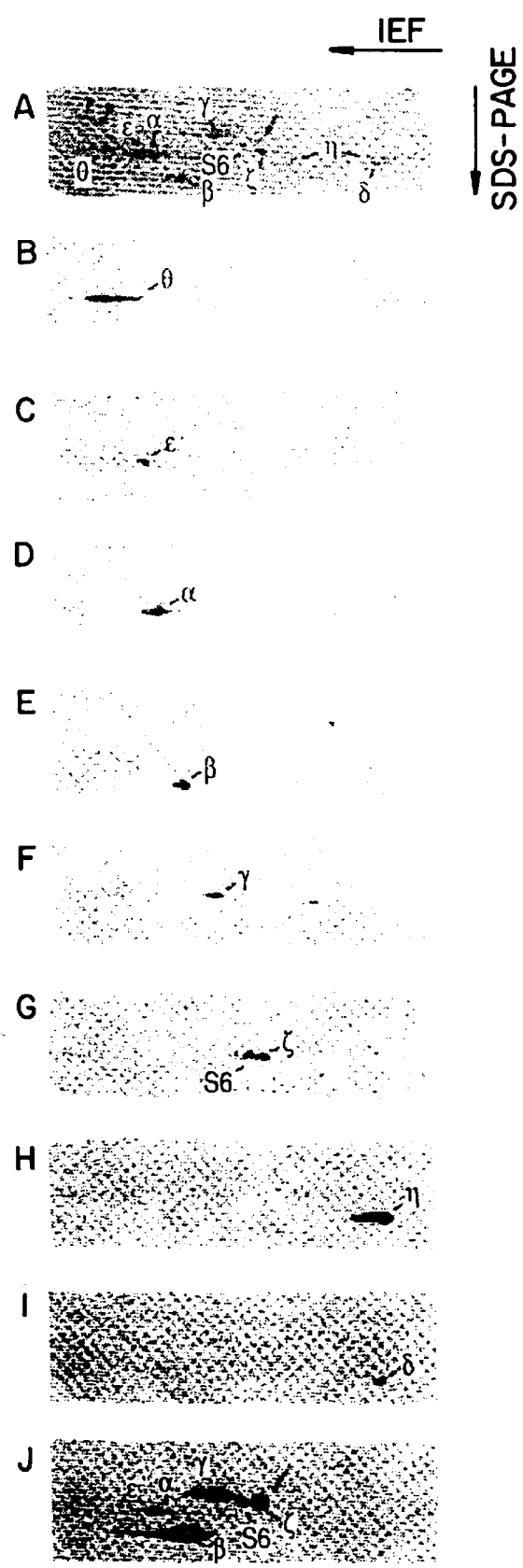

FIG. 10 2D-PAGE analysis of CCT. Subunits of ATP-affinity purified CCT from mouse testis were separated by 2D-PAGE and proteins were visualised by silver staining (A). Greek letters indicate the eight subunit species whose genes have been cloned, and S6 shows the testis-expressed subunit. A novel co-purifying 63 kDa protein of pI 6.93 is indicated by an arrow and hsp 70 proteins are shown by arrowheads. CCT subunits were immunoblotted with rabbit antibodies against carboxy terminal amino acid sequences of CCTθ (B), CCTε (C), CCTβ (E), CCTγ (F), CCTζ (G), CCTη (H), CCTδ (I), and a monoclonal antibody, 91a, against CCTα (D). Panel J shows CCT subunits immunoblotted with a rabbit antibody to a chaperonin consensus sequence thought to be involved in ATP-binding. Sequences of the peptide immunogens are shown in Table 2. In all panels the acidic side is to the left.

FIG. 11 Analysis of native populations of CCT. Partially purified CCT from mouse testis was subjected to non-denaturing isoelectric focusing followed by SDS-PAGE. Proteins were visualised by silver staining (A). Native populations of CCT resolved by non-denaturing IEF are indicated by I and II and arrowheads show hsp 70 proteins. Native populations of CCT were immunoblotted with a rabbit antibody against CCTε (B), a 30 kDa proteolytic fragment of CCTε is indicated by an arrow, or a monoclonal antibody against β-tubulin (C). In all panels the acidic side is to the left.

Figure 12:
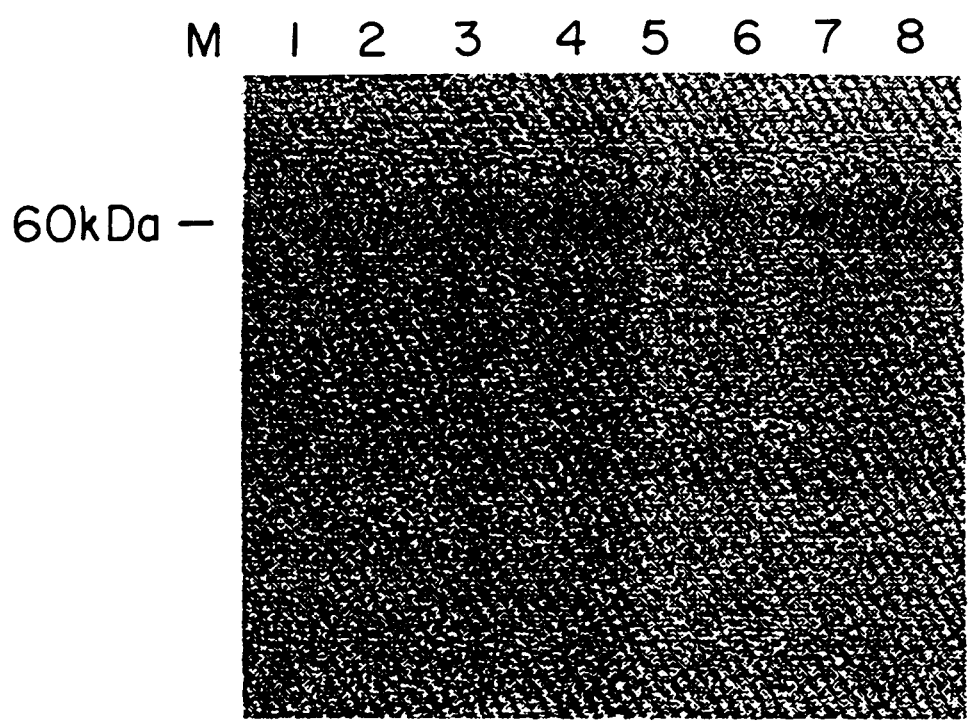

FIG. 12 shows in vitro translation products produced from individual CCT cDNA clones. Analysis of 35S-labelled CCT subunits synthesized in rabbit reticulocyte lysate from individual CCT cDNA clones. Aliquots of the i vitro translation reactions are electrophoresed on 10% SDS-PAGE and visualized by autoradiography. Lanes: (1) CCTα, (2) CCTβ, (3) CCT-γ, (4) CCTδ, (5) CCTε, (6) CCTζ, (7) CCTη, (8) CCTθ. M-molecular weight markers.

FIG. 13 shows detection of labelled CCT complex.

Figure 13A:
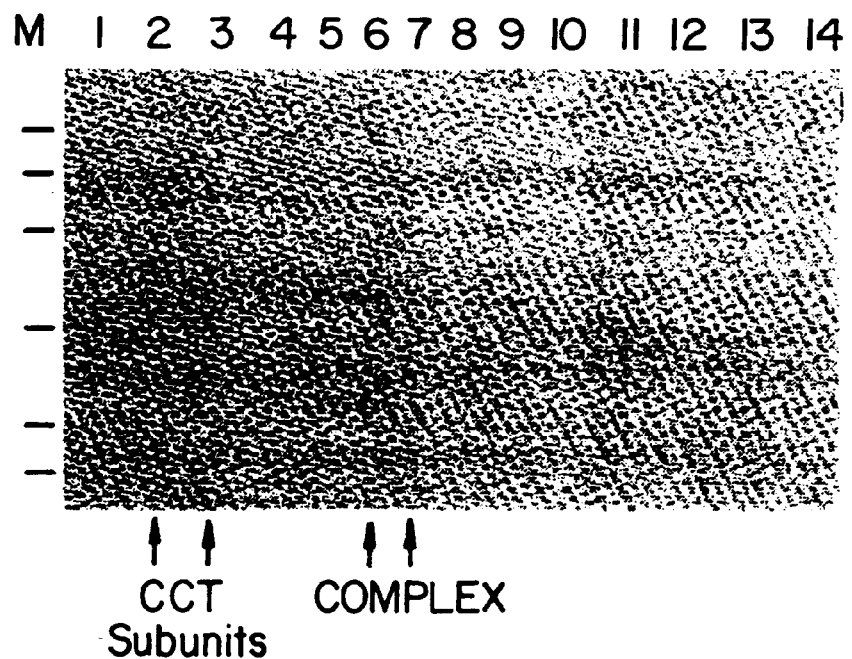

FIG. 13A shows an autoradiogram of a 100 % SDS-polyacrylamide gel of 35S-labelled CCT proteins detected in fractions from a sucrose density grandient analysis of CCT assembled in vitro in rabbit reticulocyte lysate. Eight CCT subunit mRNAs, CCTα-CCTθ were translated together and the reaction mix applied to a 10% –40% sucrose gradient as previously described (14). Lane M=marker proteins, lanes 1–14 contain 30 microlitre aliquots of 1 ml sucrose fractions (fractions 17–4). Fraction 17 is the first, lightest fraction of the gradient. Free CCT subunits are observed in fractions 16 and 15 (lanes 2 and 3) and the assembled complex is found in fractions 12 and 11 (lanes 6 and 7).

Figure 13B:
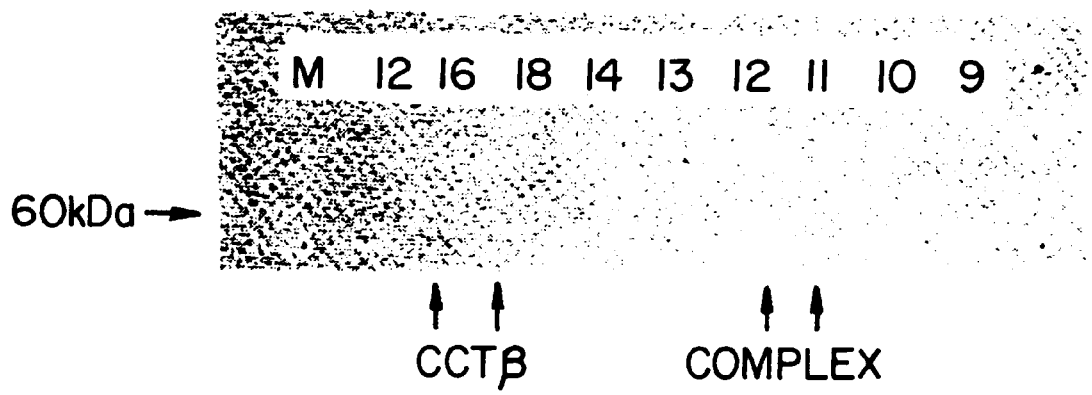

FIG. 13B shows an autoradiogram of a 10% SDS-polyacrylamide gel of 35S-labelled CCT proteins immuno-precipitated from sucrose gradient fractions by anti-CCTβ antibodies. This analysis demonstrates the presence of assembled CCT in sucrose fractions 12 and 11, but not in fractions 16 and 15. Immunoprecipitation of aliquots of fractions from the same sucrose gradient as in FIG. 13A. 300 microlitre aliquots of each of gradient fractions 17–9 were immunoprecipitated in a 1 ml reaction containing 5 microlitres of anti-CCTβ antibodies. Immune-complexes were recovered by binding to protein-A sepharose beads. Precipitation of fractions 16 and 15 with anti-CCTβ antibodies only recovers CCTβ from the mixture of 8 free, unassembled CCT subunits in the light fractions. However, precipitation of fractions 12 and 11 recovers all subunits consistent with the notion that these sucrose fractions contain assembled CCT of expected size and sedimentation properties.

Summary of Materials and Methods Used in Obtaining Gene Sequences

Purification of CCT

Mouse testis CCT was purified by sucrose gradient fractionation followed by ATP-agarose affinity chromatography as previously described [14]. Bovine testis TCP-1 ring complex (TRiC) [17] was a kind gift of F-U Hartl. Mouse F9 cells were labelled with $^{35}$S-methionine and $^{35}$S-cysteine for 5 h and CCT was purified by immunoaffinity chromatography using anti-TCP-1 monoclonal antibodies 84A and 91A [14,21]. Isoelectric focusing (IEF) [43] and non-equilibrium pH gradient electrophoresis (NEPHGE) [44] were carried out according to Corbett and Dunn [45].

Peptide Sequencing of CCT Subunits

CCT was subjected to electrophoresis on an 8% SDS-PAGE gel and protein bands were stained with 0.1% Coomassie Brilliant Blue in 0.5% acetic acid/10% aqueous methanol and destained with 10% aqueous methanol. Bands as shown in FIG. 1a were excised and the proteins were electroeluted from the gel slices. The proteins were concentrated onto polyvinylidene difluoride (PVDF) membranes using ProSpin cartridges (ABI) and each sample was digested with trypsin for 18 h at 37° C. using the method described by Fernandez et al. [46]. Digestion was terminated with trifluoroacetic acid (TFA) and tryptic peptides were isolated from the PVDF supernatants using an ABI 130A microbore separation system. TFA buffers (A: 0.1% TFA; B: 0.085% TFA, 70% acetonitrile) and a simple linear gradient (5 to 100% B in 50 min; 200 μl per min) were employed on a 2.1×100 mm Brownlee Aquapore RP-300 column. Sequence analysis on the isolated fragments was performed using an ABI 477A protein sequencer with on-line PTH detection and data handling.

Eight TRiC peptide sequences were published by Frydman et al.[17] and a further TRiC peptide sequence (P2) was a kind gift of F-U. Hartl.

C. elegans Tcp-1 Related cDNA Clones

Nine Tcp-1 related cDNA clones were reported from 5'-end single-pass sequencing of randomly selected *C. elegans* cDNA clones [22]. We compared these 9 partial sequences and found that they were derived from 4 independent genes. Because the cDNAs were all directionally cloned, we subcloned the cDNA having the longest 5' region for each of the four genes (cm08g10, cm12b10, cm11d3 and cm13e8). These pBluescript KS$^+$ clones were renamed pG1, pG2, pG3 and pG4 and represent 1.8 kb inserts for each of these four *C. elegans* genes. We accurately sequenced the 5' ends of these plasmid subclones and deduced 90 amino acids of $NH_2$-terminal sequence for each gene (FIG. 2). The deduced peptide sequences of pG1, pG2, pG3 and pG4 have 74%, 31%, 52% and 48% identity to mouse TCP-1 [20] at their $NH_2$ termini.

Human Tcp-1 Related cDNAs

A CDNA library of the human cell line HT1080 (kindly given by P. Mitchell) contains cDNA inserted at the EcoRI site of bacteriophage lambda ZAPII. These phages (1200 pfus) were plated onto each of 24 plates and phage pools of each of them were made by incubating each lawn in 5 mls of SM buffer overnight. Approximately 1.5 mls of pooled phage stock was obtained from each plate. A mixed primer for the peptide sequence TNDGATI (SEQ ID NO:63) (a motif conserved between TCP-1 and TF55) was designed (SEQ ID NO:62):

5'-AT(AG)GT(AGT)GC(ACT)CCATC(AG)TT(AGT)GT-3'.

In and out PCR using the specific primer and a primer of the lambda ZAPII polylinker on the 5' side of the inserts was performed. PCR reactions (60 mM KCl, 15 mM Tris-HCl pH8.8, 2.25 mM $MgCl_2$, 250 μM each DATP, dGTP, dCTP and dTTP, 0.4 pmol/μl each primer, 25 μl/tube) were prepared and then 1 μl of the phage stock and 1.5 unit Taq polymerase was added to each tube. These were subjected to 30 cycles of 93° C. for 15 sec, 45° C. for 15 sec and 72° C. for 30 sec. PCR products from 20 of the pools gave one or only a few 150–300 bp bands by 1% agarose gel electrophoresis. These bands were excised from the gel, reamplified and sequenced. Three Trp-1 related sequences were identified, subcloned into pBluescript $KS^+$ and named p383, p384 and ph13. The deduced polypeptide sequence from p383 has 28% identity to mouse TCP-1 over its $NH_2$-terminal 54 amino acids (excluding the primed sequence TNDGATI (SEQ ID NO:63)), that from p384 has 41% identity to mouse TCP-1 over its $NH_2$-terminal 51 amino acids (excluding TNDGATI (SEQ ID NO:63)) and that from ph13 has 24% identity to mouse TCP-1 over its $NH_2$-terminal 65 amino acids (excluding TNDGATI (SEQ ID NO:63)).

A partial cDNA clone, pAP3, was isolated from an adult human kidney cDNA library by hybridisation with a PCR fragment generated using redundant primers corresponding to Na/K transporter ATPase sequences (Malik, manuscript in preparation). Upon sequencing, pAP3 turned out to contain a 1050 base pair insert encoding a Tcp-1 related gene. Total mouse brain cDNA was subjected to PCR using two primers from the human pAP3 sequence:

forward 5'-ACATCCAGCAGCTCTGTGAG-3' (SEQ ID NO:64) and reverse 5'-CCTTGCCTAGCACTCACTCC-3' (SEQ ID NO:65).

An 800 bp fragment of the mouse orthologue of pAP3 gene was generated.

Isolation of Mouse Tcp-1 Related cDNA Clones

The mouse full-length cDNA clones encoding 6 novel TCP-1 -elated proteins were cloned as follows. An F9 embryonal carcinoma cell cDNA library was made in lambda ZAP by the method of Nagata et al. [47] and $7.5 \times 10^4$ size-selected recombinants were obtained from 1 μg poly $(A)^+$ RNA. This library was transferred onto GeneScreen Plus (NEN) membranes and duplicate filters were sequentially probed with the following five Tcp-1 related cDNA probes. The two C. elegans cDNAs, pG2 and pG3, the three human cDNAs, p383, p384 and ph13 and the 800 bp mouse RT-PCR product from pAP3 were $^{32}$P-labelled and hybridized to the membranes in Southern hybridization (SH) buffer (6×SSPE, 5×Denhart's reagent, 0.5% SDS, 10 mg/ml salmon sperm DNA) overnight at 55° C. for the two C. elegans probes, 60° C. for the three human probes, and 65° C. for the mouse probe. Between 6–12 positively hybridizing clones were purified for each probe. The longest clone (1.8–2.2 kb inserts) derived from each screening was named as pTβ2 (p383 homologue), pTε5 (p384 homologue), pTθ1 (ph13 homologue), pTζ12 (pG2 homologue), pT67 (pG3 homologue) and pTγ7 (pAP3 homologue). The relationship between these probes and clones is described in FIG. 2. The sixth mouse Tcp-1 related cDNA was recovered during a pilot experiment for a mouse testis cDNA sequencing project. Ninety-five random mouse testis cDNAs directionally cloned in lambda ZAPII were single pass sequenced from their 5' ends. The sequence of the 80th cDNA revealed a new Tcp-1 related gene which is different to all the others described above and this plasmid, pCBL80, was completely sequenced.

DNA Sequencing and Computer Analysis

The nucleotide sequences of all the Tcp-1 related genes, except pCBL80, were determined by the dideoxynucleotide chain termination method with fluorescently labelled primers using the PRISM kit and a 373A automated sequencer (ABI). Clone pCBL80 was manually sequenced by dideoxynucleotide chain termination and $^{35}$S-dATP using a combination of deletion clones and specific primers. All these sequences and deduced amino-acid sequences were analysed by UWGCG programs on the Silicon Graphics Crimson network at the SERC, Daresbury, UK. Phylogenetic analyses were also carried out at Daresbury using the PHYLIP collection of programs.

Southern Blotting

Mouse strain 129/Sv DNA (10 μg/lane) and S. cerevisiae strain 3a DNAs (1.5 μg/lane) were digested with HindIII and electrophoresed on 0.7% agarose gels and blotted onto GeneScreen Plus membranes. Probes of 1500±3 bp length were made by PCR with the mouse Tcp-1 cDNA (pT1b11) [33] and mouse Tcp-1 related cDNAs (pTβ2, pT 7, pTδ2, pTε5, pT 12 and pCBL80). These 7 probes were labelled with $^{32}$P and hybridized to the blotted membranes in SH buffer overnight at 65° C. (mouse) or at 55° C. (yeast). The membranes were washed either in 0.1×SSC containing 0.1% SDS at 65° C. (mouse) or in 2×SSC containing 0.1% SDS at 58.5° C. (yeast)

Results

Subunit Composition of the Chaperonin Containing TCP-1 (CCT)

Two-dimensional gel analysis of the subunits of the CCT reveals 7–9 spots of 52–65 kDa. FIG. 1 shows SDS-PAGE, 2D-PAGE and 2D-NEPHGE comparison of CCT isolated from mouse testis and F9 embryonal carcinoma cells, and bovine testis TCP-1 ring complex (TRiC) [17].

Excluding the Hsp70 species which co-purify specifically with the CCT [14], the testis preparations contain 9 major species (FIGS. 1b–d) and the F9 cell preparation contains seven 53–65 kDa species excluding a 45 kDa protein (FIG. 1e). This represents an increase in the number of species reported by Lewis et al. [14] because two species (S8 and S9), with basic pIs, resolve poorly in the IEF dimension of 2D-PAGE run to equilibrium. A 2D-NEPHGE analysis of bovine TRiC clearly shows 9 subunit species (FIG. 1d).

We had previously shown, using a monoclonal antibody (91A) [21] which recognizes only a single subunit (S3, TCP-1) of the CCT, that antibody-affinity purified CCT has a similar electrophoretic profile to CCT purified by ATP-agarose affinity or ion-exchange chromatography, on SDS-PAGE gels [14]. FIG. 1e shows a 2D-NEPHGE analysis of antibody-affinity purified, CCT from F9 cells; the polypeptide spot profile strongly resembles CCT biochemically purified from testis (FIGS. 1a,b) and seven 52–65 kDa species are distinguishable by the 2D analysis. A 45 kDa protein of pI 6.5 was co-purified with CCT by the antibody-affinity method, suggesting a novel co-factor or substrate of CCT (arrow head in FIG. 1e). These results confirmed that TCP-1 comprises a hetero-oligomeric complex with other polypeptides.

FIG. 1f shows a tabulation of the apparent isoelectric points and molecular weights of the CCT subunits. Frydman et al. [17] reported that bovine testis TRiC migrated as 5 bands on a 12.5% SDS-PAGE gel (P1–P5). We found that band P4 contained 5 species of polypeptides which were distinguishable from one another on a 2D gel, and we named them P4.1, 4.2, 4.3, 4.4 and 4.5 according to ascending pI. The subunits of mouse CCT (S1–S9) are numbered according to ascending pI using the mouse testis pattern as the standard. These bovine and mouse spots are distributed from pH6.1–pH7.1 and MW 65 kDa–MW52 kDa except for the most basic spot (NEPHGE analysis suggests a value of around pH 7.4 for the pI of this most basic spot).

Isolation of Mouse cDNAs Encoding Seven Novel TCP-1 Related Proteins

We previously reported [14] the existence, in various eukaryotes, of numerous genes and partial cDNA sequences related to the original mouse Tcp-1 gene [20], the first identified gene encoding an CCT subunit [14,17]. It proved necessary to use a combination of methods to isolate murine Tcp-1 related genes and clone the full-length cDNAs which encode the seven novel TCP-1 related proteins described herein. The first and second (clones pTδ2 and pTζ12) were isolated by cross-hybridization with *Caenorhabditis elegans* cDNA probes recovered from the 5' expressed sequence tag collection of Waterston et al. [1221].

The third, fourth and seventh (clones pTβ2, PTε5 and pTθ1) were isolated by cross-hybridization with human probes recovered by PCR of human HT1080 cell line cDNA using degenerate primers from a conserved region of TCP-1 and TF55.

The fifth gene (clone pCBL80) was isolated during a mouse testis cDNA sequencing project at the Chester Beatty Laboratories, London. A cDNA fragment of a Tcp-1 related gene (clone pAP3) was recovered accidentally from a human kidney CDNA library during a screen for ion transport channel genes (Malik et al., manuscript in preparation) and the sixth murine gene (clone pTγ7) was recovered by hybridization with a mouse cDNA PCR product which was made with primers derived from the sequence of this human cDNA.

FIG. 2 shows the very conserved $NH_2$-terminal domain deduced from these various Tcp-1 and Tcp-1 related genes of mouse, human, *C. elegans* and *Saccharomyces cerevisiae*. A phylogenetic analysis (UPGMA) [23] based on the amino-acid sequences of the domain showed seven groups of genes (data not shown), suggesting that in eukaryotes Tcp-1 and the Tcp-1 related genes have each evolved independently since they diverged. Analysis of the eight members of the Cct gene family suggests that the heteromeric CCT particle had already evolved in a common ancestral organism of animals, plants and yeast more than 500 million years ago and that different subunits may have different functions in protein folding.

FIG. 3 and FIG. 8 show amino-acid sequences of the seven mouse TCP-1 related proteins deduced from their full-length cDNA clones.

FIGS. 8(b) to (h) shows the DNA sequences of the seven genes and the amino acid sequences (of the deduced open reading frames) underneath.

The Seven Tcp-1 Related cDNAs Encode CCT Subunits

Internal tryptic peptides derived from an SDS-PAGE gel separation of mouse testis CCT (B1–B4, FIG. 1a) were sequenced because the $NH_2$ termini of every subunit appeared to be blocked yielding no sequence data. Frydman et al. [17] obtained some internal peptide sequences from four of the bovine testis TRiC subunits (P1, P3, P4a/TCP-1 and P5) end they also made available to us unpublished peptide sequences which we show here correspond to TRiC subunit P2. Comparisons between these mouse and bovine peptide sequences and the predicted peptide sequences of the seven Tcp-1 related cDNAs reveals that they each encode particular CCT subunit proteins (FIG. 3, FIG. 8(h), Table 1). We named these 7 new genes as Cctb (pTβ2), Cctg (pTγ7), Cctd (pTδ2), Ccte (pTε5), Cctz (pTζ12), Ccth (pCBL80) and cctq (pTθ1)and their encoded proteins as CCT β, γ, δ, ζ, η, and θ subunits respectively. We suggest renaming the Tcp-1 gene [20] as Cctα and the TCP-1 protein as CCTα. Table 1 summarizes the correspondence between the proteins encoded by Cct genes and the spots of CCT subunits separated by 2D-gel electrophoresis (FIG. 1).

Similarities Among CCT Subunit Polypeptides

Table 1 also shows the lengths in amino-acid number and molecular weights of the CCT subunits. They have similar characteristics despite the fact that they are only around 30% identical to one another in amino-acid sequence (Table 2). They vary slightly in length from 531–556 residues and in predicted molecular weight from 57456–60636 Da. These predicted molecular weights are approximately consistent with those determined by SDS-PAGE (FIG. 1).

The pIs of the subunits, experimentally determined by isoelectric focusing, correlate well with the total charge value of each predicted CCT subunit polypeptide assuming some histidine residues are charged as cations at their respective pIs (data not shown). The percentage of hydrophobic and charged amino acids in each CCT subunit is highly conserved, ranging from 31.6–33.5% and 23.9–27.3% respectively.

These conserved chemical properties probably reflect common functions of each mammalian subunit and are shared with the archaebacterial chaperonin TF55. Agard [24] suggested that hydrophobic interaction between the *E. coli* chaperonin GroEL and its substrates could be important for the folding process. The conserved percentage or hydrophobic amino acids in CCT subunits may thus be important for interaction with substrates. Hydrophobicity profiles of CCT subunits suggest conservation of hydrophobic and hydrophilic amino-acid distributions among CCT subunits, especially at the $NH_2$ terminus (data not shown).

FIG. 4 shows an alignment of all eight CCT sequences and TF55. The alignment of the peptide sequences show six major gaps (Nos. 164, 201, 246, 315, 392 and 508 in FIG. 4) and thus indicates seven blocks of homology divided by the gaps. Amongst these seven blocks, the first (Nos. 1–164) and fifth (Nos. 392–508) are the largest and contain some highly conserved motifs: LGPKGMDKM (Nos. 52–60) (SEQ ID NO:66), TITNDGATIL (Nos. 71–80) (SEQ ID NO:67), QDDEVGDGTTSVW (Nos.100–112) (SEQ ID NO:68), ERSLHDAL (Nos.423–430) (SEQ ID NO:69), and VV(A/P)GGGA (Nos. 442–448) (SEQ ID NO:70). The third motif includes a motif absolutely conserved in CCT subunits, GDGTT (SEQ ID NO:71), previously, recognized by Lewis et al. [14] to be homologous to a nucleotide phosphate binding domain of cyclic-AMP-dependent kinase and other members of this kinase family [25,26]. FIG. 5 shows a comparison between these motifs. This suggests that all the CCT subunits share the common function of ATPase activity.

Structural Genes Encoding CCT Subunits and Homologous Genes in Yeast

Southern analysis of mouse genomic DNA (FIG. 6a) shows the independent structural genes encoding seven mouse CCT subunits. Hybridization of *Saccharomyces cerevisiae* DNA with seven mouse Cct cDNA probes (FIG. 6b) shows one or two bands of PstI-digested DNA for each probe. Two Tcp-1 related genes have already been identified in yeast; the orthologue of Ccta/Tcp-1 [27] and the orthologue of Cctb [28]. Both these genes are essential [27,28] and temperature sensitive mutations in both genes affect microtubule mediated processes [28]. The CCT of *S. cerevisiae* is composed of numerous subunits and the yeast homologues of CCTα/TCP-1 and CCTβ are components of the same complex since they co-purify together [28]. Preliminary sequence data derived from yeast DNA clones corresponding to the novel sequences detected with the mouse Cct probes suggests that they are indeed the orthologues of the mouse Cct genes. Southern analysis of Arabidopsis genomic DNA with the seven Cct cDNA probes also suggests the existence of plant homologues for each subunit (data not shown); the Arabidopsis homologue of Ccta/Tcp-1 has been reported [29]. It is likely that these seven species of CCT subunits are ubiquitous in all eukaryotes.

Determination of the Subunit Compositions and Arrangements in CCT

The sequence of the eight CCT subunits reveals that they are rather divergent at the C-terminii. A monoclonal antibody, 23C, had previously been made (21) which reacts with the C-terminus of CCTalpha (Harrison-Lavoie et al, 1993, EMBO j. 7: 2847–2853) and can be used to precipitate CCT complexes. Subunit specific antibodies have now been made, utilising the sequence information provided by the invention. The antibodies were raised against C-terminus peptides with the following sequences:

| | | |
|---|---|---|
| CCTbeta: | APRKRVPDHHPC | (SEQ ID NO:1) |
| CCTgamma: | NRQTGAPDAGQE | (SEQ ID NO:2) |
| CCTdelta: | SILKIDDVVNTR | (SEQ ID NO:3) |
| CCTepsilon: | IDDIRKPGESEE | (SEQ ID NO:4) |
| CCTeta: | SAGRGRGQARFH | (SEQ ID NO:5) |
| CCTtheta: | SGKKDWDDDQND | (SEQ ID NO:6) |
| CCTzeta: | EIMRAGMSSLKG | (SEQ ID NO:7) |

The peptides were synthesised by conventional solid phase chemistry on a commercial peptide synthesizing machine. An amino terminal cysteine was added to the peptides and used to couple them to purified protein derivative (PPD) solid supports. 10 milligrams of purified peptide was coupled to 9 milligrams of PPD and the conjugate,was purified twice by column chromatography to remove unconjugated impurities. Rabbits were immunised over a 96 day period. Antibodies were screened and isolated using their binding for the peptides, using routine methods (reviewed in Harlow, E and Lane, D (1988), *Antibodies: a laboratory manual*, CSH Press, N.Y.).

Antibodies specific for individual subunits were obtained. The antibodies proved to be specific for both mouse and human subunits.

Immunoprecipitation performed under native conditions (50 mM Hepes pH8, 90 mM KCl, 0.5% TX-100) with these subunit specific antibodies shows that CCT consists of a complex mixture of particles. Different antibodies immunoprecipitate different combinations of subunits (for instance, see FIG. 9). Examination of different immunoprecipitations allows the determination of the composition of CCT in any cell type. This information enables the intelligent selection of subunit combinations to be used in in vitro construction of CCT, for instance by means of recombinant expression of subunits and their assembly.

Antibody Characterisation

2D-PAGE Mouse testis CCT was purified by sucrose gradient fractionation followed by ATP-affinity column chromatography as previously described [14]. Isoelectric focusing (IEF) was carried out according to [45]; and was followed by SDS-PAGE on 8% gels and either silver staining or electrotransfer of proteins to nitro-cellulose, immunoblotting and detection by the ECL system (Amersham) as previously described [14].

Non-denaturing Isoelectric Focusing

Mouse testis CCT was partially purified by sucrose gradient fractionation according to [14]. The fraction corresponding to 20% sucrose was mixed with an equal volume of sample buffer (40% sucrose w/v, 2% Ampholytes [Resolyte 4–8, BDH]) and subjected to non-denaturing isoelectric focusing at 500V for 4 hours. The non-denaturing IEF was performed in the same way as denaturing IEF described by [45] with the substitution of 40% sucrose for 50% urea and the omission of 3-[(3-cholamidopropyl) dimethylammonio]-1-propanesulfonate (CHAPS) in the acrylamide gel mixture. Non-denaturing IEF was followed by SDS-PAGE on 8% gels and either silver staining or electrotransfer of proteins to nitro-cellulose, immunoblotting and detection by the ECL system (Amersham).

As shown in FIG. 10, mouse testis CCT contains nine subunit species (S1-S( ) by 2D-PAGE analysis (FIG. 10A and Table 3). Tcp-1 and seven Tcp-1 related genes encoding the α, β, γ, δ, ε, ζ, η and θ subunits of mouse CCT have been cloned [52]; the testis-expressed subunit, S6, and a co-purifying 63 kDa protein (arrowed in FIG. 10A) which may be a further subunit of mouse CCT remain to be cloned. We have obtained DNA sequences of S6 and S7 and have established that they are encoded by two closely related CCTζ genes. We expect that S6 and S7 cap substitute for each other in CCT and may confer some tissue specificity in function of CCT.

A previously characterised monoclonal antibody, 91a [41,52], was used to detect CCTα(FIG. 10D). Six antibodies recognising single subunit species, BC-1, GC-1, DC-1, EC-1, TC-1 and THC-2 were produced, which reacted specifically with the β, γ, δ, ε, η and θ subunits of CCT respectively (FIGS. 10B, 10B, 10C, 10E, 10F, 10H and 10I). In addition to CCTζ the antibody ZC-1 also reacted with the testis-expressed subunit S6 (FIG. 10G), which indicates that these two subunits S6 and S7, have related carboxy germinal sequences and this supports the DNA sequence data that *hey are encoded by closly related genes. A polyclonal rabbit antibody, UM-1, was made to an amino terminal consensus motif which is highly conserved between all chaperonin sequences and is proposed to be involved in ATP binding and hydrolysis (Table 3) [52,53]. UM-1 reacted with all nine subunits of mouse testis CCT including the testis-expressed subunit S6. CCTβ, CCTε, CCTγ, CCTζ and S6 were recognised strongly (FIG. 10J), which CCTα, CCTδ, CCTη and CCTθ were recognised weakly (not shown in FIG. 10J but seen on a longer exposure). In addition to the nine subunits described above UM-1 strongly reacted with the co-purifying 63 kDa protein, which suggests that this protein could be an additional subunit species of mouse testis CCT or alternatively a modified isoform of a previously identified CCT subunit.

Resolution of Native Populations of CCT

Figure 11A:
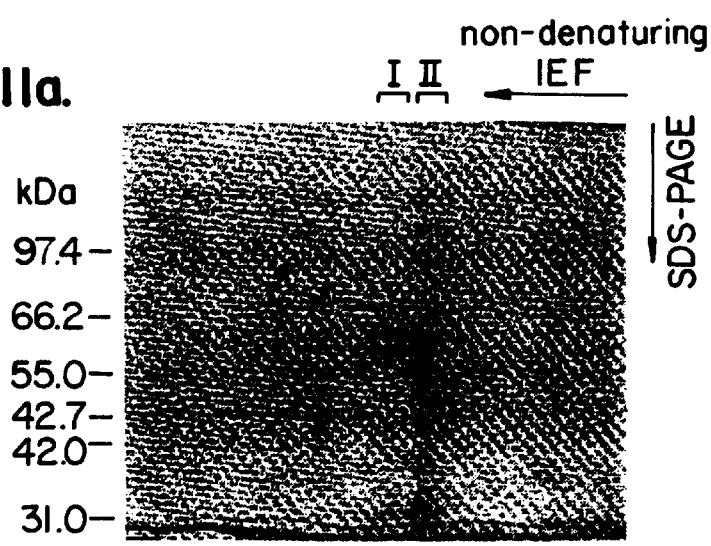
Figure 11B:
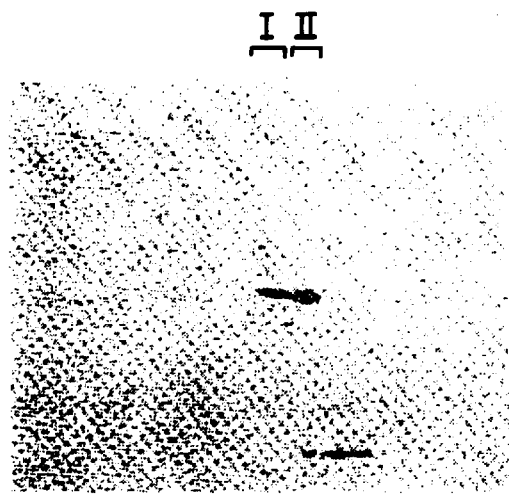
Figure 11C:
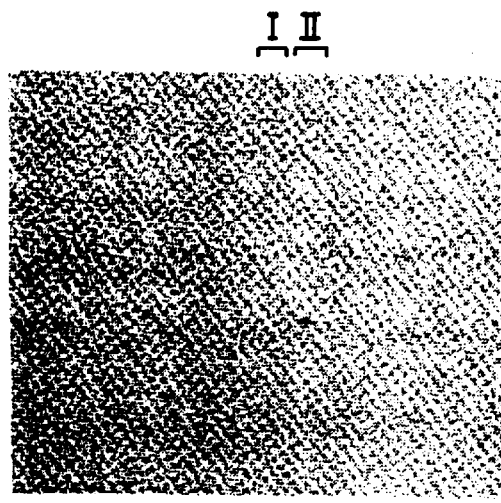

Partially purified CCT from mouse testis germ cells resolves into two distinct populations, I and II, when subjected to non-denaturing isoelectric focusing (FIG. 11). These populations were further analysed in a second dimension by SDS-PAGE and visualised by silver staining (FIG. 11A) or immunoblotting with specific antibodies (FIG. 11B and 11C). A striking difference between the two populations is that a large number of polypeptides, in addition to subunits of the CCT complex, are associated with II whilst I has only a few co-migrating species (FIG. 11A). It is likely that many of these associated polypeptides are substrates for folding by CCT and that II has a high affinity for binding polypeptide chain substrates and I has a low affinity. To date, only tubulin and actin have been established as substrates for folding by CCT in vivo [15,18,16] and both β-tubulin (FIG. 11C) and actin (data not shown) are found associated with II but not with I.

Arrowheads show hsp 70 proteins which resolve away from CCT (FIG. 11A), possibly due to the high pH conditions during sample loading. Small amounts of hsp 70 proteins co-immunoprecipitate with CCT under native conditions [14,52] suggesting that hsp 70 is found associated due to its interaction with polypeptide chains undergoing folding on CCT. Therefore, this technique is a stringent analysis of protein interactions and a reflection of the high affinity of CCT form II for substrates.

FIG. 11B shows CCT populations I and II immunoblotted with a polyclonal rabbit-antibody to CCTε, however both populations contain all nine subunits of mouse testis CCT as demonstrated by immunoblotting with the antibodies described above (data not shown). Since resolution of native IEF markers in this system demonstrates that separation is on the basis of charge and not size (data not shown), we propose that I and II represent two distinct conformations of hetero-oliogmeric CCT which are resolved under these conditions due to different complements of surface charges being exposed in each conformation.

During the biochemical extraction of CCT from mouse testis and from other sources, we often observe limited proteolysis of all the subunits in preparations of intact 900 kDa CCT complex. A 30 kDa fragment of CCTε (arrowed in FIG. 11B) is detected only in form II. This differential susceptibility to proteolysis indicates that the cleavage site is more accessible in II, which is supporting evidence that I and II adopt different conformations. The size of these proteolytic fragments are between 28 to 30 kDa suggesting that the protease sensitive sites reside in the putative apical polypeptide chain binding region of each CCT subunit [53].

Discussion of Antibodies

Antibodies specific for each subunit species will be useful in investigating the combination and arrangement of subunits in the CCT complex and the antibody, UM-1, which recognises all the subunits can be used as a general reagent to identify CCT from other eukaryotes. Characterisation of mouse testis CCT revealed that the testis-expressed subunit, S6 [52], is related to S7 and that a co-purifying 63 kDa protein may be a novel subunit of mouse testis CCT. The 63 kDa protein is probably encoded by a novel Tcp-1-related gene.

A problem with the biochemical analysis of large molecular weight complexes such as CCT is in resolving different states even when these states differ by the addition of accessory polypeptides, such as substrates or co-factors. Herein described a non-denaturing isoelectric focusing technique that facilitates the resolution of two forms of CCT. One form is bound to many other polypeptides and is susceptible to proteolysis whilst the other form is bound to only a few other polypeptides and is resistant to proteolysis.

These results suggest that CCT in the cell may adopt two distinct conformations with different affinity for polypeptide chain substrates. The conformation with high binding affinity for substrates may expose a domain which is susceptible to proteolysis in each CCT subunit, and this site may be located within the substrate binding domain since it is in a similar position to the substrate binding domain of GroEL [54,55]. In GroEL, dramatic structural changes have bees associated with ATP binding [5,56]. One interpretation of our data is that binding or hydrolysis of ATP acts as a switch between conformational forms of CCT that interact strongly or weakly with polypeptide chain substrates. The wide range of polypeptides found associated with CCT suggests that the physiological substrates for CCT may not be limited to actin and tubulin and implies that CCT has a general role in protein folding in the eukaryotic cytosol.

Production and Assembly of Polypeptide Components of a Folding Complex (1) In order to create a complex able to fold a polypeptide, messenger RNA dependent rabbit reticulocyte lysates are used. Synthetic, capped mRNAs encoding each of the CCT subunits to associate are independently synthesised in vitro by RNA transcription of each linearised Bluescript™ plasmid containing a full-length coding CCT sequence under the appropriate control sequences. (Sambrook et al, 1989, *Molecular Cloning: a Laboratory Manual,* CSH Press, New York) These RNAs are added to rabbit reticulocyte lysate containing $^{35}$S-methionine for synthesis of $^{35}$S-labelled CCT subunits, which facilitates detection on native electrophoretic gels or sucrose density gradients. The presence of particular subunits is confirmed also using subunit-specific antibodies, by immunoprecipitation.

Synthesis of subunits together leads to the assembly of a complex whose ability to bind to and/or fold a polypeptide can be tested.

Translating MRNA encoding a substrate polypeptide to be folded, such as actin or tubulin, with the subunits enables detection of complexes of labelled CCT and substrate. Labelled substrate facilitates this. Although rabbit reticulocyte extracts contain endogenous CCT, this does not cycle with the newly synthesised CCT subunits.

(2) The rabbit reticulocyte system of (1) is used to investigate different combinations of subunits to assess their ability to associate and form a complex able to bind and/or fold a polypeptide of Interest. For example, an assembled complex of translation products of mRNAs encoding eight subunits (S1, S2, S3, S4, S5, S6 or S7, S8 and S9) is precipitated using an antibody specific for any one of the subunits (FIGS. 13 and 14) and its binding to a substrate also translated in vitro, such as tubulin, is testable (16).

(3) Subunits are expressed in *E. coli* using appropriate vectors. The combination of subunits chosen for a particular purpose, ie folding of a particular polypeptide, is made in large quantities. The subunits associate to form heteromeric structures of expected sedimentation properties and molecular weight. Subunits may be expressed individually and then purified, with the assembly carried out in vitro by mixing CCT subunits in the appropriate combinations.

(4) For large scale production, subunits are expressed using Baculovirus. A nucleotide sequence encoding a subunit is inserted into a suitable expression vector and operably linked to control elements within that vector. The vector and wild-type viral genome are transfected into an insect host cell where the vector and viral genome are allowed to recombine to form a recombinant baculovirus expression vector. The baculovirus vector is packaged into infectious recombinant baculoviruses. Large quantities of subunits are produced which are able to associate to form complexes able to fold a polypeptide substrate.

(5) Folding of a polypeptide substrate, for instance tubulin, actin or luciferase, is Vested by a standard technique as described in Frydman et al (17). See also references (4), (15) and (16).

Assembly of Mouse CCT from 8 Recombinant cDNA Clones

The purpose of these experiments is to show that the 8 cDNA clones encoding the CCTα, β, γ, δ, ε, ζ, η and θ subunits are necessary and sufficient to produce recombinant CCT proteins capable of co-assembling into the heteromeric core-CCT complex which we expect from our biochemical and genetic analysis to be constructed from these 8 subunits. We have demonstrated this in the following way. Plasmids containing T3 or T7 promoters upstream of the CCT cDNA open reading frames were linearized with appropriate restriction endonucleases to produce templates for the synthesis of each CCT MRNA by T3 or T7 RNA polymerase. The plasmids which we use are CCTα/pT1611, CCTβ/pTβ2, CCTγ/pTγ7, CCTδ/pTδ2, CCTε/pTε5, CCTζ/pTζ12, CCTη/pTη29 and CCTθ/pTθ1.

When rabbit reticulocyte lysate was programmed singly with each CCT subunit encoding cDNA a 35S-labelled polypeptide of expected molecular weight was synthesized (FIG. 12).

To show assembly, the lysate was programmed with all eight subunit encoding plasmids together. After synthesis the reaction mix was applied to a 10–40% sucrose gradient in order to resolve the assembled CCT complexes from the free subunits as shown previously by us (Reference 14). Labelled CCT complex can be detected at 20% sucrose density (FIG. 13A) and all the subunits are immuno-precipitated using antibodies specific to single subunits (FIG. 13B). This demonstrates the principle of co-assembly from the 8 subunit genes. This process is repeatable using subunit proteins expressed in mammalian tissue culture cells, bacteria and yeasts.

Yeast Expression

The *Pischia pastoris* heterologous gene expression system has been used to express individual CCT subunits in yeast. Specifically we inserted the CCTε open reading frame into pHIL-D2. This construct was used to transform Pischia producing strains expressing CCTε under the control of the AOX1 promoter. These strains, such as WIL5, were shown to produce CCTε in response to induction by methanol, both using small scale cultures (to measure time course of induction) and subsequently by large-scale fermentation. In order to follow expression of mouse CCTε in *Pischia pastoris* in these experiments anti-CCTε antibodies disclosed herein were utilised. Without the antibodies the experiments would not have been possible. All procedures were according to the In Vitrogen manual and as described in Cregg, J. M. et al., 1993 Bio/Technology, Vol. 11, 905–910.

Expression in Human Cells

CCT subunits were expressed in human cells as free subunits and incorporated into endogenous CCT complex using standard eukaryotic expression vectors such as pcDNA1. Specically, the CCTα and CCTβ open reading frames were subcloned into pcDNA1 giving plasmids pEXα and pEXβ. These plasmids were transzected into human 293T cells and COT protein expression was measured by Western blotting and immunoprecipitation using antibodies disclosed herein. Substantial expression of CCTα and CCTβ was obtained.

Additional Discussion

The symmetry of each ring of the CCT double-torus particle is yet to be determined, although EM-negative stain analysis suggests that it is likely to comprise 8 or 9 subunits [14]. Although the stoichiometric composition of CCT with respect to individual polypeptide species has not yet been determined biochemically, we have confirmed that there are seven species of CCT subunits by 2D-NEPHGE analysis of antibody-affinity purified CCT purified from mouse F9 cells. We have been able to assign eight CCT subunit proteins to eight Cct genes including Tcp-1/Cctα. The analysis of CCT [14] and the actin chaperonin [15] by negative stain electron microscopy is consistent with the heteromeric nature of the CCT since the particles appear quasi-symmetrical with different sized/shaped subunits. Lewis et al. [14] previously showed that mouse testis CCT contained more subunits than human HEp2 cell CCT and Roobol and Carden [19] found differences between brain CCT and testis CCT derived from rats and guinea-pigs. These data are consistent with the idea that a particular CCT particle is composed of several kinds of subunits, although some subunits may be replaceable depending on tissue type.

The eight genes (the seven new ones plus the original TCP-1 (alpha)) described herein are sufficient to reconstitute CCT. Certain cell types such as mouse F9 and human HEp-2 contain abundant levels of 7 CCT subunits, with the S2 subunit, encoded by the CCTε gene, appearing to be absent, based on protein analysis but it may be rapidly turning over or post-translationally modified causing levels of S2 to be difficult to measure. The role of the mouse testis expressed subunit, S6, is unclear but it probably has an exchangeable function with S7, the product of the CCTzeta gene, given that antibodies raised against S7 react with S6 and that we have DNA clones for two closely related CCTζ genes. Northern blotting and protein analysis lead to the conclusion that S1, S2, S3, S4, S5, S7, S8 and S9 are ubiquitously expressed and therefore that they constitute the eight essential components of general CCT activity.

One can build/reconstruct CCT folding machines (complexes) using combinations of these seven components. Specialised proteins may need the presence of an additional, eg tissue specific, subunit or other cofactors to be correctly folded. However, these should be able to be incorporated into CCT machines in combination with the subunits provided herein.

Evolutionary Origin of CCT Subunit Genes

All organisms are classifiable into three primary kingdoms, eubacteria, archaebacteria and eukaryotes, based upon ribosomal RNA sequences [30]. Several proteins found in archaebaczeria and eukaryotic cytosol are similar to each other and those of mitochondria, chloroplasts and eubacteria are also similar to each other [31].

Our sequence analysis has shown that each CCT subunit is very similar to TF55 of an archaebacterium *Sulfolobus shibatae* (FIG. 4, Table 2) and only weakly related to GroEL and other chaperonin proteins which are thought to have evolved from a common eubacterial origin [10]. Another archaebacterium, *Pyrodictium occultum*, also has an ATPase complex whose tryptic peptides share 70% identity with TF55 [32]. These results suggest that all the CCT genes evolved from a common ancestor of eukaryotes and archaebacteria. Each eukaryotic Cct gene is as divergent from another Cct gene as it is from TF55 and this suggests that the eukaryotic genes diverged from one another very early in the eukaryotic lineage,. An evolutionary tree of CCT subunits and TF55 based on amino-acid substitutions supports these ideas (FIG. 7). If the amino-acid substitution rate of each CCT subunit is constant during evolution [33] and assuming that yeasts and animals diverged 1000–1200 million years ago, then we calculate 1800–2400 million years for the divergence times of CCT subunits.

However, the orthologues of each CCT member in animals, plants and yeasts are much more similar to one another and this suggests that each subunit has evolved an independent function a long time ago which has been maintained in most eukaryotes. Since CCT is composed of 7–9 subunit species and other chaperonins have only one or two subunit species, it seems likely that the CCT has evolved more complex functions in eukaryotic cytosol. The increased complexity of CCT may have facilitated the evolution of the highly organized eukaryotic cytosol by co-evolution between CCT and substrates.

Function of the CCT

CCT, TF55 and classical chaperonins (GroEL, Hsp60 and Rubisco binding protein) all have ATPase activity. It seems likely that the conservation of sequence in this family reflects the maintenance of ATPase activity rather than the ability to form-double torus structures which many unrelated proteins, such as glutamine synthetase [34] can adopt. In GroEL the conformation of the particle changes by rotation of the GroEL subunits relative to the perpendicular axis upon binding ATP [5]. EM analysis of the actin chaperonin in the presence and absence of ATP suggests that similar large conformational changes may occur [15]. There are three highly conserved motifs among the TCP-1, TF55 and GroEL family chaperonins (see FIG. 4 in [14]). Two motifs, (I/V)T(N/K)DG(A/V) (T/S) (SEQ ID NO:72) and GDGTT (S/T) (SEQ ID NO:73), are positioned at the $NH_2$ terminus and one, V(A/P)GGG (SEQ ID NO:74), towards the COOH terminus. These three motifs are also conserved in the other CCT subunits and interestingly the amino-acid sequences around GDGTT(S/T) (SEQ ID NO:73) (FIG. 5) have homologies to the phosphate binding domains for ATP hydrolysis shared by the cAMP-dependent kinase family proteins [25,26]. If these widely separated motifs are indeed involved in ATP binding and hydrolysis, then they may be responsible for the large conformational changes the chaperonins make upon ATP binding. This idea is supported by our knowledge of the structure of cAMP-dependent protein kinase-α[26], Hsp70 [35,36] and actin/myosin [37]; several domains required for ATPase activity are widely separated in the amino-acid chains of these proteins.

One possible reason for the multiplicity of CCT subunit species may be the contributions of each subunit to interaction with other co-factors involved in protein folding processes. We previously showed that CCT binds Hsp70 species [14]. In *E. coli*, DnaK (Hsp70family) and GroE (Hsp60 family) are thought to cooperate with DnaJ in the folding of newly synthesized proteins [38,39]. It is possible that a similar mechanism involving Hsp70, DnaJ homologues [40] and CCT occurs in eukaryotic cytosol. We found a weak homology between the COOH terminus of CCTδ and Hsp70 family proteins (not shown) and this may suggest a role for CCTδ in interactions between chaperones and co-factors.

It is known that some chaperonins (GroE, Hsp60) are not able to fold substrates which can be folded by CCT; mitochondrial Hsp60 does not fold or form a binary complex with denatured α-actin [15] and GroEL/ES does not fold luciferase although it can bind it [17]. This suggests that the substrate specificity of classical chaperonins and CCT differs and that CCT might have changed its spectrum of substrate building by evolving a far larger number of subunit species than the single subunit species chaperoning. Sternlicht et al. [18] reported that a 40 kDa newly synthesized protein co-purified with CCT in addition to actin and tubulin. This would seem to be a novel substrate of CCT. The general function of CCT, in addition to its folding of actin and tubulin, is illustrated by a genetic experiment in *S. cerevisiae*. Expression of human HTR3 cDNA which encodes a partial TCP-1 related polypeptide rescued a mutation in amino-acid transport [41]. The HTR3 polypeptide has 96% homology to mouse CCTζ, and is thus the human orthologue of CCTζ. This suggests that CCT might assist folding of a protein affecting amino-acid transport. CCT binds in vitro to chromaffin granule membranes coupled to an affinity matrix [42]. This suggests a role for CCT for the regulation of secretory vesicles and membrane trafficking events. A short peptide sequence of the TCP-1-related chaperonin of oats [42] which seems to have evolved the specialized function of folding phytochrome, is more related to CCTδ (Residue nos. 369–384 in FIG. 4) than the other CCT subunits. Specialized functions might have been derived from different primordial Cct genes in different ancestral organisms.

CCT is believed to act mainly as folding machinery or tubulin and actin by many investigators despite the tact that these proteins show no significant amino-acid sequence homology. Actin and tubulin are extremely abundant proteins in the cell, and thus they were probably the easiest proteins to be detected as substrates [18].

Table 4 summarises proteins known to be folded by CCT. Firefly luciferase has been reported to be folded by CCT in vitro (17, 61) and brain CCT was purified as a neurofilament fragment binding protein [19]. Lingappa et al. [62] reported that TCP-1 and/or a TCP-1-like chaperonin is involved in capsid assembly by hepatitis B virus in vitro. Thus, CCT may assist in the folding of not only actin and tubulin but also a more wider range of proteins in vivo.

Functional analysis of each subunit species will provide further information-of the role of CCT in vivo in general protein folding events in eukaryotic cells.

We have identified nine subunit species of CCT in mammalian testis and seven major species in mouse F9 cells and we cloned seven Tcp-1 related genes encoding CCT subunits found in common to testis and F9 cell CCT. Tcp-1/Cctα and these genes are so highly conserved from mammals to yeast they can be detected by cross-species Southern blotting analysis. The amino-acid sequences of the mouse and yeast orthologues of two CCT subunit species (CCTα and CCTβ) show 61% and 66% sequence identity, respectively. All CCT subunits contain a motif similar to an ATP binding domain of cAMP-dependent protein kinase and other kinases of this family, suggesting all CCT subunits have independent ATPase activities. The mouse CCT subunits show only 26–35% homology between one subunit protein species and another and phylogenetic analysis suggests that the divergence time of CCT subunit genes is approximately two times as long as the divergence time of animals and yeasts.

These observations suggest that each subunit has evolved a specific, independent function in addition to the common ATPase function a long time ago and that these functions are maintained in all eukaryotes. The expansion of the number of subunit species compared to other chaperonins may have allowed more complex functions required for folding and assembly of highly evolved eukaryotic proteins.

References

1. Ellis et al., Annu. Rev. Biociem. 7991, 60: 321–347.
2. Harti et al., Annu. Rev. Biophys. Biomol. Struct. 1992, 21: 293–322.
3. Horwich et al., Phil. Trans. R. Soc. Lond. 1993, 21: 293–322.
4. Langer et al., EMBO J. 1992, 11: 4757–4765.
5. Saibil et al., Curr. Biol. 1993, 3: 265–273.
6. Weissman et al., Cell 1994, 78: 693–702.
7. Georgopoulos et al., J. Mol. Biol. 1973, 76: 45– 60.
8. Horwich et al., Cell 1993, 74: 909–917.
9. Cheng et al., Nature 1989, 337: 620–625.
10. Gupta, Biochem. Internatl. 1990, 20: 833–841.
11. Trent et al., Nature 1991, 354: 490–493.
12. Hemmingsen, Nature 1992, 357: 650.
13. Ellis, Nature 1992, 358: 191–192.
14. Lewis et al., Nature 1992, 358: 249–252.
15. Gao et al., Cell 1992, 69: 1043–1050.
16. Yaffe et al., Nature 1992, 358: 245–248.
17. Frydman et al., EMBO J. 1992, 11: 4767–4778.
18. Sternlicht et al., Proc. Natl. Acad. Sci. USA 1993, 90: 9422–9426.
19. Roobol et al., J. Neurochem. 1993, 60: 2327–2330.
20. Willison et al., Cell 1989, 44: 727–738.
21. Willison et al., Cell 1989, 57: 621–632.
22. Waterston et al., Nature Genet. 1992, 1: 114–123.
23. Sokal et al., W H Freeman & Company 1963.
24. Agard, Science 1993, 260: 1903–1904.
25. Hanks et al., Science 1988, 241: 42–52.
26. Taylor et al., Ann. Rev. Cell Biol. 1992, 8: 429–462.
27. Ursic et al., Mol. Cell Biol. 1991, 11: 2629–2640.
28. Miklos et al., Proc. Natl. Acad. Sci. USA 1994, in press.
29. Mori et al., Gene 1992, 122: 381–382.
30. Woese et al., Proc. Natl. Acad. Sci. USA 1990, 87: 4576–4579.
31. Iwabe et al., Proc. Natl. Acad. Sci. USA 1989, 86: 9355–9359.
32. Phipps et al., Nature 1993, 361: 475–477.
33. Kubota et al., Gene 1991, 105: 269–273.
34. Almassy et al., Nature 1986, 323: 304–309.
35. Flaherty et al., Proc. Natl. Acad. Sci. USA 1991, 88: 5041–5045.
36. Bork et al., Proc. Natl. Acad. Sci. USA 1992,, 89: 7290–7294.
37. Rayment et al., Science 1993, 261: 58–65.
38. Langer et al., Nature 1.992, 356: 683–689.
39. Craig, Science 1993, 260: 1902–1903.
40. Silver et al., Cell 1993, 74: 5–6.
41. Segel et al., Proc. Natl. Acad. Sci. USA 1992, 89: 6060–6064.
42. Creutz et al., J. Biol. Chem. 1994 269 32035–32038.
43. O'Farrell, J. Biol. Chem. 1975, 250: 4007–4021.
44. O'Farrell et al., Cell 1977, 12: 1133–1142.
45. Corbett et al., Edited by Granam J M, Higgins J A, New Jersey: Humana Press 1992, 219–227.
46. Fernandez et al., Anal Biochem. 1992, 201: 255–264.
47. Nagata et al., Nucleic Acids Res. 1990, 19: 2441–2447.
48. Kirchhoff et al., Nucleic Acid Res. 1990, 18: 4247.
49. Khan et al., Nature Genet 1992, 2: 180–185.
50. Saitou et al., Mol. Biol. Evol. 1987, 4: 406–425.
51. Ursic et al., Gene 1988, 68: 267–274.
52. Kubota et al., Curr. Biol. 1994, 4: 89–99.
53. Kim et al., TIBS 1994, 19: 543–548.
54. Fenton et al., Nature 1994, 371: 614–619.
55. Braig et al., Nature 1994, 371: 578–586.
56. Chen et al., Nature 1994, 371: 261–264.
57. Melki et al., J. Cell Biol 1993, 128: 1301–1310.
58. Gao et al., Mol. Cell. Biol. 1993, 13: 2478–2485.
59. Rommelaere et al., PNAS USA 1993, 90: 11975–11979.
60. Gao et al., J. Cell. Biol. 1994, 125: 989–996.
61. Frydman et al., Nature. 1994, 370: 111–117.
62. Lingappa et al, J. Cell. Biol 1994, 125: 99–111.

TABLE 1

Characteristics of CCT subunits.

| Subunit species | Spot on 2D gels | Number of amino acids | Molecular weight |
|---|---|---|---|
| CCTα | S3 | 556 | 60513 |
| CCTβ | S4 | 536 | 57456 |
| CCTγ | S5 | 545 | 60636 |
| CCTδ | S9 | 539 | 58073 |
| CCTε | S2 | 541 | 59631 |
| CCTζ | S7 | 531 | 58011 |
| CCTη | S8 | 541 | 59658 |
| CCTθ | S1 | 548 | 59562 |

The spot numbers of CCT subunits on 2D gels (S1–S9) are described in FIG. 1. The correspondences of CCT is subunit α to spot S3 [14], ε to S2, ζ to S7 and θ to S1 (FIG. 10) were determined by Western blotting of 2D gels with antibodies which react specifically with each subunit. The other correspondences are derived from the peptide sequencing data described in FIG. 3 and the Western blotting data in FIG. 10. Numbers of amino acids and molecular weights of CCT subunits are calculated from the amino-acid sequences in FIG. 3 and FIG. 8.

TABLE 2

Homology among mouse CCT subunits and archaebacterial chaperone TF55.

| | CCTα | CCTβ | CCTγ | CCTδ | CCTε | CCTζ | CCTη | CCTθ | TF55 |
|---|---|---|---|---|---|---|---|---|---|
| CCTα | | 7 (24) | 3 (13) | 4 (12) | 3 (12) | 6 (24) | 5 (21) | 5 (19) | 4 (16) |
| CCTβ | 35.4 | | 4 (8) | 4 (10) | 5 (9) | 5 (14) | 4 (8) | 6 (8) | 6 (8) |
| CCTγ | 32.5 | 28.4 | | 5 (10) | 2 (2) | 5 (16) | 4 (8) | 5 (11) | 2 (2) |
| CCTδ | 32.1 | 28.2 | 33.1 | | 4 (9) | 5 (10) | 3 (4) | 5 (11) | 5 (10) |
| CCTε | 31.9 | 31.9 | 32.2 | 36.2 | | 5 (17) | 4 (6) | 4 (6) | 3 (6) |
| CCTζ | 27.1 | 25.0 | 29.2 | 28.5 | 31.0 | | 4 (8) | 3 (12) | 4 (13) |
| CCTη | 34.6 | 31.9 | 34.6 | 28.5 | 28.4 | 26.3 | | 4 (8) | 3 (6) |
| CCTθ | 27.5 | 25.4 | 27.4 | 27.8 | 29.1 | 22.5 | 24.0 | | 29.0 |
| TF55 | 38.7 | 32.0 | 34.1 | 37.1 | 38.0 | 35.1 | 34.9 | 5 (10) | |

Percentages of identical amino acids are shown below the diagonal and numbers of gaps/insertions are above the diagonal. Numbers in parentheses are total lengths of gaps/insertions given in amino acid numbers.

TABLE 3

Immunochemical analysis of CCT subunits

| Antibody used for detection | Sequence of peptide immunogen | Corresponding subunit of mouse CCT | Species recognised on 2D gel | SEQ ID NO: |
|---|---|---|---|---|
| ThC-2 | SGKKDWDDDQND | CCTθ | S1 | 6 |
| EC-1 | IDDIRKPGESEE | CCTε | S2 | 4 |
| 91a* | — | CCTα | S3 | |
| BC-1 | APRKRVPDHHPC | CCTβ | S4 | 1 |
| GC-1 | NRQTGAPDAGQE | CCTγ | S5' | 2 |
| ZC-1 | EIMRAGMSSLKG | CCTζ | S6,S7 | 7 |
| TC-1 | SAGRGRGQARFH | CCTη | S8 | 5 |
| DC-1 | SILKIDDWNTR | CCTδ | S9 3 | |
| UM-1 | QDDEVGDGTTSW | chaperonin consensus motif | S1,S2,S3,S4,S5, S6,S7,S8,S9,p63** | 68 |

91a* denotes a rat monoclonal antibody which recognises the C-terminus of CCTα [2].
p63** denotes a co-purifying 63kDa protein of pI 6.93.

TABLE 4

Proteins known to be folded or assembled by CCT and co-factors.

| Protein | Experiment | Reference |
|---|---|---|
| actin | in vitro, in vivo | 15,18 |
| actin-RVP | in vitro | 57 |
| tubulin | in vitro, in vivo | 16,17,18,57,58,59,60 |
| neurofilament (fragment) | in vitro | 19 |
| luciferase | in vitro | 17,61 |
| hepatitis B virus capsid | in vitro* | 62 |

*TCP-1 or TCP-1-like chaperonin recognized by anti-TCP-1 antibody.

What is claimed is:

1. A method of producing a polypeptide folding complex, the method comprising expression of subunits of the complex from encoding nucleic acid therefor and causing or allowing assembly of the subunits into the complex, the complex comprising all of the subunits (i) to (viii) as follows:
    (i) a subunit which comprises the amino acid sequence shown in SEQ ID NO:24;
    (ii) a subunit which comprises the amino acid sequence shown in SEQ ID NO:25;
    (iii) a subunit which comprises the amino acid sequence shown in SEQ ID NO:26;
    (iv) a subunit which comprises the amino acid sequence shown in SEQ ID NO:27;
    (v) a subunit which comprises the amino acid sequence shown in SEQ ID NO:28;
    (vi) a subunit which comprises the amino acid sequence shown in SEQ ID NO:29;
    (vii) a subunit which comprises the amino acid sequence shown in SEQ ID NO:30;
    (viii) a subunit which comprises the amino acid sequence shown in SEQ ID NO:31.

2. A method according to claim 1 wherein the complex comprises a subunit which comprises the amino acid sequence shown in SEQ ID NO:24.

3. A method according to claim 2 wherein the subunit which comprises the amino acid sequence shown in SEQ ID NO:24 is produced by expression from encoding nucleic acid comprising the nucleotide sequence shown in SEQ ID NO:54.

4. A method according to claim 1 wherein the complex comprises a subunit which comprises the amino acid sequence shown in SEQ ID NO:25.

5. A method according to claim 4 wherein the subunit which comprises the amino acid sequence shown in SEQ ID NO:25 is produced by expression from encoding nucleic acid comprising the nucleotide sequence shown in SEQ ID NO:55.

6. A method according to claim 1 wherein the complex comprises a subunit which comprises the amino acid sequence shown in SEQ ID NO:26.

7. A method according to claim 6 wherein the subunit which comprises the amino acid sequence shown in SEQ ID NO:26 is produced by expression from encoding nucleic acid comprising the nucleotide sequence shown in SEQ ID NO:56.

8. A method according to claim 1 wherein the complex comprises a subunit which comprises the amino acid sequence shown in SEQ ID NO:27.

9. A method according to claim 8 wherein the subunit which comprises the amino acid sequence shown in SEQ ID NO:27 is produced by expression from encoding nucleic acid comprising the nucleotide sequence shown in SEQ ID NO:57.

10. A method according to claim 1 wherein the complex comprises a subunit which comprises the amino acid sequence shown in SEQ ID NO:28.

11. A method according to claim 10 wherein the subunit which comprises the amino acid sequence shown in SEQ ID NO:28 is produced by expression from encoding nucleic acid comprising the nucleotide sequence shown in SEQ ID NO:58.

12. A method according to claim 1 wherein the complex comprises a subunit which comprises the amino acid sequence shown in SEQ ID NO:29.

13. A method according to claim 12 wherein the subunit which comprises the amino acid sequence shown in SEQ ID NO:29 is produced by expression from encoding nucleic acid comprising the nucleotide sequence shown in SEQ ID NO:59.

14. A method according to claim 1 wherein the complex comprises a subunit which comprises the amino acid sequence shown in SEQ ID NO:30.

15. A method according to claim 14 wherein the subunit which comprises the amino acid sequence shown in SEQ ID NO:30 is produced by expression from encoding nucleic acid comprising the nucleotide sequence shown in SEQ ID NO:60.

16. A method according to claim 1 wherein the complex comprises a subunit which comprises the amino acid sequence shown in SEQ ID NO:31.

17. A method according to claim 16 wherein the subunit which comprises the amino acid sequence shown in SEQ ID NO:31 is produced by expression from encoding nucleic acid comprising the nucleotide sequence shown in SEQ ID NO:61.

18. A method according to claim 1 wherein the complex comprises all of the subunits (i) to (viii) as follows:
(i) a subunit which comprises the amino acid sequence shown in SEQ ID NO:24;
(ii) a subunit which comprises the amino acid sequence shown in SEQ ID NO:25;
(iii) a subunit which comprises the amino acid sequence shown in SEQ ID NO:26;
(iv) a subunit which comprises the amino acid sequence shown in SEQ ID NO:27;
(v) a subunit which comprises the amino acid sequence shown in SEQ ID NO:28;
(vi) a subunit which comprises the amino acid sequence shown in SEQ ID NO:29;
(vii) a subunit which comprises the amino acid sequence shown in SEQ ID NO:30; and
(viii) a subunit which comprises the amino acid sequence shown in SEQ ID NO:31.

19. A method according to claim 1 wherein assembly of the subunits into the complex is by in vitro mixing following expression.

20. A method according to claim 18 wherein assembly of the subunits into the complex is by in vitro mixing following expression.

21. A method according to claim 1 wherein the subunits are expressed together.

22. A method according to claim 18 wherein the subunits are expressed together.

23. A recombinant polypeptide folding complex comprising all of the polypeptide subunits (i) to (viii) as follows, produced by expression from encoding nucleic acid:
(i) a subunit which comprises the amino acid sequence shown in SEQ ID NO:24;
(ii) a subunit which comprises the amino acid sequence shown in SEQ ID NO:25;
(iii) a subunit which comprises the amino acid sequence shown in SEQ ID NO:26;
(iv) a subunit which comprises the amino acid sequence shown in SEQ ID NO:27;
(v) a subunit which comprises the amino acid sequence shown in SEQ ID NO:28;
(vi) a subunit which comprises the amino acid sequence shown in SEQ ID NO:29;
(vii) a subunit which comprises the amino acid sequence shown in SEQ ID NO:30;
(viii) a subunit which comprises the amino acid sequence shown in SEQ ID NO:31.

24. A complex according to claim 23 wherein the complex comprises a subunit which comprises the amino acid sequence shown in SEQ ID NO:24.

25. A complex according to claim 24 wherein the subunit which comprises the amino acid sequence shown in SEQ ID NO:24 is produced by expression from encoding nucleic acid comprising the nucleotide sequence shown in SEQ ID NO:54.

26. A complex according to claim 23 wherein the complex comprises a subunit which comprises the amino acid sequence shown in SEQ ID NO:25.

27. A complex according to claim 24 wherein the subunit which comprises the amino acid sequence shown in SEQ ID NO:25 is produced by expression from encoding nucleic acid comprising the nucleotide sequence shown in SEQ ID NO:55.

28. A complex according to claim 23 wherein the complex comprises a subunit which comprises the amino acid sequence shown in SEQ ID NO:26.

29. A complex according to claim 28 wherein the subunit which comprises the amino acid sequence shown in SEQ ID NO:26 is produced by expression from encoding nucleic acid comprising the nucleotide sequence shown in SEQ ID NO:56.

30. A complex according to claim 23 wherein the complex comprises a subunit which comprises the amino acid sequence shown in SEQ ID NO:27.

31. A complex according to claim 30 wherein the subunit which comprises the amino acid sequence shown in SEQ ID NO:27 is produced by expression from encoding nucleic acid comprising the nucleotide sequence shown in SEQ ID NO:57.

32. A complex according to claim 23 wherein the complex comprises a subunit which comprises the amino acid sequence shown in SEQ ID NO:28.

33. A complex according to claim 32 wherein the subunit which comprises the amino acid sequence shown in SEQ ID NO:28 is produced by expression from encoding nucleic acid comprising the nucleotide sequence shown in SEQ ID NO:58.

34. A complex according to claim 23 wherein the complex comprises a subunit which comprises the amino acid sequence shown in SEQ ID NO:29.

35. A complex according to claim 34 wherein the subunit which comprises the amino acid sequence shown in SEQ ID NO:29 is produced by expression from encoding nucleic acid comprising the nucleotide sequence shown in SEQ ID NO:59.

36. A complex according to claim 23 wherein the complex comprises a subunit which comprises the amino acid sequence shown in SEQ ID NO:30.

37. A complex according to claim 36 wherein the subunit which comprises the amino acid sequence shown in SEQ ID NO:30 is produced by expression from encoding nucleic acid comprising the nucleotide sequence shown in SEQ ID NO:60.

38. A complex according to claim 23 wherein the complex comprises a subunit which comprises the amino acid sequence shown in SEQ ID NO:31.

39. A complex according to claim 38 wherein the subunit which comprises the amino acid sequence shown in SEQ ID NO:31 is produced by expression from encoding nucleic acid comprising the nucleotide sequence shown in SEQ ID NO:61.

40. A complex according to claim 23 wherein the complex comprises all of the subunits (i) to (viii) as follows:
(i) a subunit which comprises the amino acid sequence shown in SEQ ID NO:24;
(ii) a subunit which comprises the amino acid sequence shown in SEQ ID NO:25;
(iii) a subunit which comprises the amino acid sequence shown in SEQ ID NO:26;
(iv) a subunit which comprises the amino acid sequence shown in SEQ ID NO:27;
(v) a subunit which comprises the amino acid sequence shown in SEQ ID NO:28;
(vi) a subunit which comprises the amino acid sequence shown in SEQ ID NO:29;
(vii) a subunit which comprises the amino acid sequence shown in SEQ ID NO:30; and
(viii) a subunit which comprises the amino acid sequence shown in SEQ ID NO:31.

41. An isolated DNA comprising a nucleotide sequence encoding a subunit of a polypeptide folding complex, wherein the subunit is selected from the group consisting of:

SEQ ID NO:24, SEQ ID NO:25, SEQ ID NO:26, SEQ ID NO:27, SEQ ID NO:28, SEQ ID NO:29, SEQ ID NO:30, and SEQ ID NO:31.

42. The isolated DNA according to claim 41, wherein the nucleotide sequence encodes SEQ ID NO:24.

43. The isolated DNA according to claim 41, wherein the nucleotide sequence encodes SEQ ID NO:25.

44. The isolated DNA according to claim 41, wherein the nucleotide sequence encodes SEQ ID NO:26.

45. The isolated DNA according to claim 41, wherein the nucleotide sequence encodes SEQ ID NO:27.

46. The isolated DNA according to claim 41, wherein the nucleotide sequence encodes SEQ ID NO:28.

47. The isolated DNA according to claim 41, wherein the nucleotide sequence encodes SEQ ID NO:29.

48. The isolated DNA according to claim 41, wherein the nucleotide sequence encodes SEQ ID NO:30.

49. The isolated DNA according to claim 41, wherein the nucleotide sequence encodes SEQ ID NO:31.

50. The isolated DNA according to claim 41, wherein the nucleotide sequence is selected from the group consisting of SEQ ID NO:54, SEQ ID NO:55, SEQ ID NO:56, SEQ ID NO:57, SEQ ID NO:58, SEQ ID NO:59, SEQ ID NO:60, and SEQ ID NO:61.

\* \* \* \* \*

SEQUENCE LISTING (1) GENERAL INFORMATION:

(iii) NUMBER OF SEQUENCES: 74

(2) INFORMATION FOR SEQ ID NO:1:

(i) SEQUENCE CHARACTERISTICS:
       (A) LENGTH: 12 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:1:

Ala Pro Arg Lys Arg Val Pro Asp His His Pro Cys
1               5                   10

(2) INFORMATION FOR SEQ ID NO:2:

(i) SEQUENCE CHARACTERISTICS:
       (A) LENGTH: 12 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:2:

Asn Arg Gln Thr Gly Ala Pro Asp Ala Gly Gln Glu
1               5                   10

(2) INFORMATION FOR SEQ ID NO:3:

(i) SEQUENCE CHARACTERISTICS:
       (A) LENGTH: 12 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:3:

Ser Ile Leu Lys Ile Asp Asp Val Val Asn Thr Arg
1               5                   10

(2) INFORMATION FOR SEQ ID NO:4:

(i) SEQUENCE CHARACTERISTICS:
       (A) LENGTH: 12 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:4:

Ile Asp Asp Ile Arg Lys Pro Gly Glu Ser Glu Glu
1               5                   10

(2) INFORMATION FOR SEQ ID NO:5:

(i) SEQUENCE CHARACTERISTICS:
       (A) LENGTH: 12 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:5:

Ser Ala Gly Arg Gly Arg Gly Gln Ala Arg Phe His
1               5                   10

(2) INFORMATION FOR SEQ ID NO:6:

(i) SEQUENCE CHARACTERISTICS:
            (A) LENGTH: 12 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:6:

Ser Gly Lys Lys Asp Trp Asp Asp Asp Gln Asn Asp
1               5                   10

(2) INFORMATION FOR SEQ ID NO:7:

(i) SEQUENCE CHARACTERISTICS:
            (A) LENGTH: 12 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:7:

Glu Ile Met Arg Ala Gly Met Ser Ser Leu Lys Gly
1               5                   10

(2) INFORMATION FOR SEQ ID NO:8:

(i) SEQUENCE CHARACTERISTICS:
            (A) LENGTH: 44 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:8:

Lys Ser Arg Leu Met Gly Leu Glu Ala Leu Lys Ser His Ile Met Ala
1               5                   10                  15

Ala Lys Ala Val Ala Asn Thr Met Arg Thr Ser Leu Gly Pro Asn Gly
                20                  25                  30

Leu Asp Lys Met Met Val Asp Lys Asp Gly Asp Val
            35                  40

(2) INFORMATION FOR SEQ ID NO:9:

(i) SEQUENCE CHARACTERISTICS:
            (A) LENGTH: 44 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:9:

Lys Ser Arg Leu Met Gly Leu Glu Ala Leu Lys Ser His Ile Met Ala
1               5                   10                  15

Ala Lys Ala Val Ala Asn Thr Met Arg Thr Ser Leu Gly Pro Asn Gly

```
                    20                  25                  30

Leu Asp Lys Met Met Val Asp Lys Asp Gly Asp Val
            35                  40
```

(2) INFORMATION FOR SEQ ID NO:10:

(i) SEQUENCE CHARACTERISTICS:
        (A) LENGTH: 44 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:10:

```
Gln Lys Arg Ile Thr Gly Val Glu Ala Val Lys Ser His Ile Leu Ala
1               5                   10                  15

Ala Arg Ala Val Ala Asn Thr Leu Arg Thr Ser Leu Gly Pro Arg Gly
                20                  25                  30

Leu Asp Lys Met Leu Val Ser Pro Asp Gly Asp Val
            35                  40
```

(2) INFORMATION FOR SEQ ID NO:11:

(i) SEQUENCE CHARACTERISTICS:
        (A) LENGTH: 44 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:11:

```
Gln Asp Arg Asp Lys Pro Ala Gln Ile Arg Phe Ser Asn Ile Ser Ala
1               5                   10                  15

Ala Lys Ala Val Ala Asp Ala Ile Arg Thr Ser Leu Gly Pro Lys Gly
                20                  25                  30

Met Asp Lys Met Ile Gln Asp Gly Lys Gly Asp Val
            35                  40
```

(2) INFORMATION FOR SEQ ID NO:12:

(i) SEQUENCE CHARACTERISTICS:
        (A) LENGTH: 44 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:12:

```
Lys Asp Lys Asp Lys Pro Glu Ser Val Arg Asn Ser Asn Ile Val Ala
1               5                   10                  15

Ala Lys Ala Val Ala Asp Ala Val Arg Thr Ser Leu Gly Pro Arg Gly
                20                  25                  30

Met Asp Lys Met Ile Gln Ser Gly Asn Gly Asp Val
            35                  40
```

(2) INFORMATION FOR SEQ ID NO:13:

(i) SEQUENCE CHARACTERISTICS:
        (A) LENGTH: 44 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:13:

Gly Asp Arg Ser Thr Gly Glu Ala Val Arg Ser Gln Asn Val Met Ala
1               5                   10                  15

Ala Ala Ser Ile Ala Asn Ile Val Lys Ser Ser Phe Gly Pro Val Gly
            20                  25                  30

Leu Asp Lys Met Leu Val Asp Asp Ile Gly Asp Val
        35                  40

(2) INFORMATION FOR SEQ ID NO:14:

(i) SEQUENCE CHARACTERISTICS:
        (A) LENGTH: 44 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:14:

Gly Asp Arg Ser Thr Gly Glu Thr Ile Arg Ser Gln Asn Val Met Ala
1               5                   10                  15

Ala Ala Ser Ile Ala Asn Ile Val Lys Ser Ser Leu Gly Pro Val Gly
            20                  25                  30

Leu Asp Lys Met Leu Val Asp Asp Ile Gly Asp Val
        35                  40

(2) INFORMATION FOR SEQ ID NO:15:

(i) SEQUENCE CHARACTERISTICS:
        (A) LENGTH: 44 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:15:

Gly Lys Arg Thr Thr Gly Gln Gly Ile Arg Ser Gln Asn Val Thr Ala
1               5                   10                  15

Ala Val Ala Ile Ala Asn Ile Val Lys Ser Ser Leu Gly Pro Val Gly
            20                  25                  30

Leu Asp Lys Met Leu Val Asp Asp Val Gly Asp Val
        35                  40

(2) INFORMATION FOR SEQ ID NO:16:

(i) SEQUENCE CHARACTERISTICS:
        (A) LENGTH: 44 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:16:

Gly Asp Arg Gln Ser Gly Gln Asp Val Arg Thr Gln Asn Val Met Ala
1               5                   10                  15

Cys Gln Ala Val Ser Asn Ile Val Lys Thr Ser Leu Gly Pro Val Gly
            20                  25                  30

Leu Asp Lys Met Leu Val Asp Asp Ile Gly Asp Val
        35                  40

(2) INFORMATION FOR SEQ ID NO:17:

(i) SEQUENCE CHARACTERISTICS:
        (A) LENGTH: 44 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:17:

```
Thr Asp Ser Ser Gln Gly Ile Pro Gln Leu Val Ser Asn Ile Ser Ala
1               5                   10                  15

Cys Gln Val Ile Ala Glu Ala Val Arg Thr Thr Leu Gly Pro Arg Gly
            20                  25                  30

Met Asp Lys Leu Ile Val Asp Gly Arg Gly Lys Ala
        35                  40
```

(2) INFORMATION FOR SEQ ID NO:18:

(i) SEQUENCE CHARACTERISTICS:
        (A) LENGTH: 44 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:18:

```
Thr Lys Arg Glu Ser Gly Arg Lys Val Gln Ser Gly Asn Ile Asn Ala
1               5                   10                  15

Ala Lys Thr Ile Ala Asp Ile Ile Arg Thr Cys Leu Gly Pro Lys Ser
            20                  25                  30

Met Met Lys Met Leu Leu Asp Pro Met Gly Gly Ile
        35                  40
```

(2) INFORMATION FOR SEQ ID NO:19:

(i) SEQUENCE CHARACTERISTICS:
        (A) LENGTH: 44 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:19:

```
Ala Glu Val Ala Arg Val Gln Ala Ala Leu Ala Val Asn Ile Ser Ala
1               5                   10                  15

Ala Arg Gly Leu Gln Asp Val Leu Arg Thr Asn Leu Gly Pro Lys Gly
            20                  25                  30

Thr Met Lys Met Leu Val Ser Gly Ala Gly Asp Ile
        35                  40
```

(2) INFORMATION FOR SEQ ID NO:20:

(i) SEQUENCE CHARACTERISTICS:
        (A) LENGTH: 44 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:20:

```
Ala Glu Leu Ala Arg His Ala Ala Ala Leu Glu Leu Asn Ile Ser Gly
1               5                  10                  15

Ala Arg Gly Leu Gln Asp Val Met Arg Ser Asn Leu Gly Pro Lys Gly
                20                  25                  30

Thr Leu Lys Met Leu Val Ser Gly Ala Gly Asp Ile
            35                  40
```

(2) INFORMATION FOR SEQ ID NO:21:

(i) SEQUENCE CHARACTERISTICS:
        (A) LENGTH: 44 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:21:

```
Ala Asp Glu Glu Arg Ala Glu Ile Ala Arg Leu Ser Ser Phe Ile Gly
1               5                  10                  15

Ala Ile Ala Ile Gly Asp Leu Val Lys Ser Thr Leu Gly Pro Lys Ala
                20                  25                  30

Met Asp Lys Ile Leu Leu Ser Ser Gly Arg Asp Ala
            35                  40
```

(2) INFORMATION FOR SEQ ID NO:22:

(i) SEQUENCE CHARACTERISTICS:
        (A) LENGTH: 44 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:22:

```
Ala Asp Glu Glu Arg Ala Glu Thr Ala Arg Leu Thr Ser Phe Ile Gly
1               5                  10                  15

Ala Ile Ala Ile Gly Asp Leu Val Lys Ser Thr Leu Gly Pro Lys Gly
                20                  25                  30

Met Asp Lys Ile Leu Leu Ser Ser Gly Arg Asp Ala
            35                  40
```

(2) INFORMATION FOR SEQ ID NO:23:

(i) SEQUENCE CHARACTERISTICS:
        (A) LENGTH: 44 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:23:

```
Val Thr Glu Glu Arg Ala Glu Asn Ala Arg Leu Ser Ala Phe Val Gly
1               5                  10                  15

Ala Ile Ala Val Gly Asp Leu Val Lys Ser Thr Leu Gly Pro Lys Gly
                20                  25                  30

Met Asp Lys Leu Leu Gln Ser Ala Ser Ser Asn Thr
            35                  40
```

(2) INFORMATION FOR SEQ ID NO:24:

-continued (i) SEQUENCE CHARACTERISTICS:
    (A) LENGTH: 556 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:24:

```
Met Glu Gly Pro Leu Ser Val Phe Gly Asp Arg Ser Thr Gly Glu Ala
 1               5                  10                  15

Val Arg Ser Gln Asn Val Met Ala Ala Ser Ile Ala Asn Ile Val
             20                  25                  30

Lys Ser Ser Phe Gly Pro Val Gly Leu Asp Lys Met Leu Val Asp Asp
             35                  40                  45

Ile Gly Asp Val Thr Ile Thr Asn Asp Gly Ala Thr Ile Leu Lys Leu
50                  55                  60

Leu Glu Val Glu His Pro Ala Ala Lys Val Leu Cys Glu Leu Ala Asp
65                  70                  75                  80

Leu Gln Asp Lys Glu Val Gly Asp Gly Thr Thr Ser Val Val Ile Ile
                 85                  90                  95

Ala Ala Glu Leu Leu Lys Asn Ala Asp Glu Leu Val Lys Gln Lys Ile
                100                 105                 110

His Pro Thr Ser Val Ile Ser Gly Tyr Arg Leu Ala Cys Lys Glu Ala
                115                 120                 125

Val Arg Tyr Ile Asn Glu Asn Leu Ile Ile Asn Thr Asp Glu Leu Gly
            130                 135                 140

Arg Asp Cys Leu Ile Asn Thr Ala Lys Thr Ser Met Ser Ser Lys Ile
145                 150                 155                 160

Ile Gly Ile Asn Gly Asp Tyr Phe Ala Asn Met Val Val Asp Ala Val
                165                 170                 175

Leu Ala Val Lys Tyr Thr Asp Ala Arg Gly Gln Pro Arg Tyr Pro Val
            180                 185                 190

Asn Ser Val Asn Ile Leu Lys Ala His Gly Arg Ser Gln Ile Glu Ser
            195                 200                 205

Met Leu Ile Asn Gly Tyr Ala Leu Asn Cys Val Val Gly Ser Gln Gly
210                 215                 220

Met Pro Lys Arg Ile Val Asn Ala Lys Ile Ala Cys Leu Asp Phe Ser
225                 230                 235                 240

Leu Gln Lys Thr Lys Met Lys Leu Gly Val Gln Val Val Ile Thr Asp
                245                 250                 255

Pro Glu Lys Leu Asp Gln Ile Arg Gln Arg Glu Ser Asp Ile Thr Lys
                260                 265                 270

Glu Arg Ile Gln Lys Ile Leu Ala Thr Gly Ala Asn Val Ile Leu Thr
            275                 280                 285

Thr Gly Gly Ile Asp Asp Met Tyr Leu Lys Tyr Phe Val Glu Ala Gly
        290                 295                 300

Ala Met Ala Val Arg Arg Val Leu Lys Arg Asp Leu Lys His Val Ala
305                 310                 315                 320

Lys Ala Ser Gly Ala Ser Ile Leu Ser Thr Leu Ala Asn Leu Glu Gly
                325                 330                 335

Glu Glu Thr Phe Glu Val Thr Met Leu Gly Gln Ala Glu Glu Val Val
                340                 345                 350

Gln Glu Arg Ile Cys Asp Asp Glu Leu Ile Leu Ile Lys Asn Thr Lys
            355                 360                 365
```

```
Ala Arg Thr Ser Ala Ser Ile Ile Leu Arg Gly Ala Asn Asp Phe Met
    370             375                 380

Cys Asp Glu Met Glu Arg Ser Leu His Asp Ala Leu Cys Val Val Lys
385             390                 395                 400

Arg Val Leu Glu Leu Lys Ser Val Val Pro Gly Gly Ala Val Glu
                405                 410                 415

Ala Ala Leu Ser Ile Tyr Leu Glu Asn Tyr Ala Thr Asn Met Gly Ser
            420                 425                 430

Arg Glu Gln Leu Ala Ile Ala Glu Phe Ala Arg Ser Leu Leu Val Ile
            435                 440                 445

Pro Asn Thr Leu Ala Val Asn Ala Ala Gln Asp Ser Thr Asp Leu Val
            450                 455                 460

Ala Lys Leu Arg Ala Phe His Asn Glu Ala Gln Val Asn Pro Glu Arg
465             470                 475                 480

Lys Asn Leu Lys Trp Ile Gly Leu Asp Leu Val His Gly Lys Pro Arg
                485                 490                 495

Asp Asn Lys Gln Ala Gly Val Phe Glu Pro Thr Ile Val Lys Val Lys
                500                 505                 510

Ser Leu Lys Phe Ala Thr Glu Ala Ala Ile Thr Ile Leu Arg Ile Asp
            515                 520                 525

Asp Leu Ile Lys Leu His Pro Glu Ser Lys Asp Lys His Gly Ser
            530                 535                 540

Tyr Glu Asn Ala Val His Ser Gly Ala Leu Asp Asp
545                 550                 555

(2) INFORMATION FOR SEQ ID NO:25:

(i) SEQUENCE CHARACTERISTICS:
        (A) LENGTH: 535 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:25:

Met Ala Ser Leu Ser Leu Ala Pro Val Asn Ile Phe Lys Ala Gly Ala
1               5                   10                  15

Asp Glu Glu Arg Ala Glu Ile Ala Arg Leu Ser Ser Phe Ile Gly Ala
                20                  25                  30

Ile Ala Ile Gly Asp Leu Val Lys Ser Thr Leu Gly Pro Lys Gly Met
            35                  40                  45

Asp Lys Ile Leu Leu Ser Ser Gly Arg Asp Ala Ala Leu Met Val Thr
50                  55                  60

Asn Asp Gly Ala Thr Ile Leu Lys Asn Ile Gly Val Asp Asn Pro Ala
65                  70                  75                  80

Ala Lys Val Leu Val Asp Met Ser Arg Val Gln Asp Asp Glu Val Gly
                85                  90                  95

Asp Gly Thr Thr Ser Val Thr Val Leu Ala Ala Glu Leu Leu Arg Glu
                100                 105                 110

Ala Glu Ser Leu Ile Ala Lys Lys Ile His Pro Gln Thr Ile Ile Ser
            115                 120                 125

Gly Trp Arg Glu Ala Thr Lys Ala Ala Arg Glu Ala Leu Leu Ser Ser
            130                 135                 140

Ala Val Asp His Gly Ser Asp Glu Ala Arg Phe Trp Gln Asp Leu Met
145                 150                 155                 160
```

```
Asn Ile Ala Gly Thr Thr Leu Ser Ser Lys Leu Leu Thr His His Lys
            165                 170                 175

Asp His Phe Thr Lys Leu Ala Val Glu Ala Gly Leu Arg Leu Lys Gly
            180                 185                 190

Ser Gly Asn Leu Glu Ala Ile His Val Ile Lys Lys Leu Gly Gly Ser
            195                 200                 205

Leu Ala Asp Ser Tyr Leu Asp Glu Gly Phe Leu Leu Asp Lys Lys Ile
    210                 215                 220

Gly Val Asn Gln Pro Lys Arg Ile Glu Asn Ala Lys Ile Leu Ile Ala
225                 230                 235                 240

Asn Thr Gly Met Asp Thr Asp Lys Ile Lys Ile Phe Gly Ser Arg Val
            245                 250                 255

Arg Val Asp Ser Thr Ala Lys Val Ala Glu Ile Glu His Ala Glu Lys
            260                 265                 270

Glu Lys Met Lys Glu Lys Val Glu Arg Ile Leu Lys His Gly Ile Asn
            275                 280                 285

Cys Phe Ile Asn Arg Gln Leu Ile Tyr Asn Tyr Pro Glu Gln Leu Phe
    290                 295                 300

Gly Ala Ala Gly Val Met Ala Ile Glu His Ala Asp Phe Ala Gly Val
305                 310                 315                 320

Glu Arg Leu Ala Leu Val Thr Gly Gly Glu Ile Ala Ser Thr Phe Asp
            325                 330                 335

His Pro Glu Leu Val Lys Leu Gly Ser Cys Lys Leu Ile Glu Glu Val
            340                 345                 350

Met Ile Gly Glu Asp Lys Leu Ile His Phe Ser Gly Val Ala Leu Gly
            355                 360                 365

Glu Ala Cys Thr Ile Val Leu Arg Gly Ala Thr Gln Gln Ile Leu Asp
370                 375                 380

Glu Ala Glu Arg Ser Leu His Asp Ala Leu Cys Val Leu Ala Gln Thr
385                 390                 395                 400

Val Lys Asp Pro Arg Thr Val Tyr Gly Gly Gly Cys Ser Glu Met Leu
            405                 410                 415

Met Ala His Ala Val Thr Gln Leu Ala Asn Arg Thr Pro Gly Lys Glu
            420                 425                 430

Ala Val Ala Met Glu Ser Phe Ala Lys Ala Leu Arg Met Leu Pro Thr
            435                 440                 445

Ile Ile Ala Asp Asn Ala Gly Tyr Asp Ser Ala Asp Leu Val Ala Gln
    450                 455                 460

Leu Arg Ala Ala His Ser Glu Gly His Ile Thr Ala Gly Leu Asp Met
465                 470                 475                 480

Lys Glu Gly Thr Ile Gly Asp Met Ala Val Leu Gly Ile Thr Glu Ser
            485                 490                 495

Phe Gln Val Lys Arg Gln Val Leu Leu Ser Ala Glu Ala Ala Glu
            500                 505                 510

Val Ile Leu Arg Val Asp Asn Ile Ile Lys Ala Ala Pro Arg Lys Arg
            515                 520                 525

Val Pro Asp His His Pro Cys
530                 535

(2) INFORMATION FOR SEQ ID NO:26:

(i) SEQUENCE CHARACTERISTICS:
        (A) LENGTH: 545 amino acids
        (B) TYPE: amino acid
        (C) STRANDEDNESS: single
```

(D) TOPOLOGY: linear (ii) MOLECULE TYPE: peptide (xi) SEQUENCE DESCRIPTION: SEQ ID NO:26:

```
Met Met Gly His Arg Pro Val Leu Val Leu Ser Gln Asn Thr Lys Arg
1               5                   10                  15

Glu Ser Gly Arg Lys Val Gln Ser Gly Asn Ile Asn Ala Ala Lys Thr
            20                  25                  30

Ile Ala Asp Ile Ile Arg Thr Cys Leu Gly Pro Lys Ser Met Met Lys
            35                  40                  45

Met Leu Leu Asp Pro Met Gly Gly Ile Val Met Thr Asn Asp Gly Asn
        50                  55                  60

Ala Ile Leu Arg Glu Ile Gln Val Gln His Pro Ala Ala Lys Ser Met
65                  70                  75                  80

Ile Glu Ile Ser Arg Thr Gln Asp Glu Val Gly Asp Gly Thr Thr
                85                  90                  95

Ser Val Ile Ile Leu Ala Gly Glu Met Leu Ser Val Ala Glu His Phe
            100                 105                 110

Leu Glu Gln Gln Met His Pro Thr Val Val Ile Ser Ala Tyr Arg Met
        115                 120                 125

Ala Leu Asp Asp Met Ile Ser Thr Leu Lys Lys Ile Ser Thr Pro Val
        130                 135                 140

Asp Val Asn Asn Arg Glu Met Met Leu Ser Ile Ile Asn Ser Ser Ile
145                 150                 155                 160

Thr Thr Lys Val Ile Ser Arg Trp Ser Ser Leu Ala Cys Asn Ile Ala
                165                 170                 175

Leu Asp Ala Val Lys Thr Val Gln Phe Glu Glu Asn Gly Arg Lys Glu
            180                 185                 190

Ile Asp Ile Lys Lys Tyr Ala Arg Val Glu Lys Ile Pro Gly Gly Ile
            195                 200                 205

Ile Glu Asp Ser Cys Val Leu Arg Gly Val Met Ile Asn Lys Asp Val
        210                 215                 220

Thr His Pro Arg Met Arg Arg Tyr Ile Lys Asn Pro Arg Ile Val Leu
225                 230                 235                 240

Leu Asp Ser Ser Leu Glu Tyr Lys Lys Gly Glu Ser Gln Thr Asp Ile
                245                 250                 255

Glu Ile Thr Arg Glu Glu Asp Phe Thr Arg Ile Leu Gln Met Glu Glu
            260                 265                 270

Glu Tyr Ile His Gln Leu Cys Glu Asp Ile Ile Gln Leu Lys Pro Asp
            275                 280                 285

Val Val Ile Thr Glu Lys Gly Ile Ser Asp Leu Ala Gln His Tyr Leu
        290                 295                 300

Met Arg Ala Asn Val Thr Ala Ile Arg Arg Val Arg Lys Thr Asp Asn
305                 310                 315                 320

Asn Arg Ile Ala Arg Ala Cys Gly Ala Arg Ile Val Ser Arg Pro Glu
                325                 330                 335

Glu Leu Arg Glu Asp Asp Val Gly Thr Gly Ala Gly Leu Leu Glu Ile
            340                 345                 350

Lys Lys Ile Gly Asp Glu Tyr Phe Thr Phe Ile Thr Asp Cys Lys Asp
            355                 360                 365

Pro Lys Ala Cys Thr Ile Leu Leu Arg Gly Ala Ser Lys Glu Ile Leu
        370                 375                 380

Ser Glu Val Glu Arg Asn Leu Gln Asp Ala Met Gln Val Cys Arg Asn
```

```
                                    -continued
385                 390                 395                 400

Val Leu Leu Asp Pro Gln Leu Val Pro Gly Gly Ala Ser Glu Met
                405                 410                 415

Ala Val Ala His Ala Leu Thr Glu Lys Ser Lys Ala Met Thr Gly Val
                420                 425                 430

Glu Gln Trp Pro Tyr Arg Ala Val Ala Gln Ala Leu Glu Val Ile Pro
            435                 440                 445

Arg Thr Leu Ile Gln Asn Cys Gly Ala Ser Thr Ile Arg Leu Leu Thr
        450                 455                 460

Ser Leu Arg Ala Lys His Thr Gln Glu Ser Cys Glu Thr Trp Gly Val
465                 470                 475                 480

Asn Gly Glu Thr Gly Thr Leu Val Asp Met Lys Glu Leu Gly Ile Trp
                485                 490                 495

Glu Pro Leu Ala Val Lys Leu Gln Thr Tyr Lys Thr Ala Val Glu Thr
                500                 505                 510

Ala Val Leu Leu Leu Arg Ile Asp Asp Ile Val Ser Gly His Lys Lys
            515                 520                 525

Lys Gly Asp Asp Gln Asn Arg Gln Thr Gly Ala Pro Asp Ala Gly Gln
530                 535                 540

Glu
545

(2) INFORMATION FOR SEQ ID NO:27:

(i) SEQUENCE CHARACTERISTICS:
        (A) LENGTH: 539 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:27:

Met Pro Glu Asn Val Ala Ser Arg Ser Gly Ala Pro Thr Ala Gly Pro
1               5                   10                  15

Gly Ser Arg Gly Lys Ser Ala Tyr Gln Asp Arg Asp Lys Pro Ala Gln
            20                  25                  30

Ile Arg Phe Ser Asn Ile Ser Ala Ala Lys Ala Val Ala Asp Ala Ile
        35                  40                  45

Arg Thr Ser Leu Gly Pro Lys Gly Met Asp Lys Met Ile Gln Asp Gly
    50                  55                  60

Lys Gly Asp Val Thr Ile Thr Asn Asp Gly Ala Thr Ile Leu Lys Gln
65                  70                  75                  80

Met Gln Val Leu His Pro Ala Ala Arg Met Leu Val Glu Leu Ser Lys
                85                  90                  95

Ala Gln Asp Ile Glu Ala Gly Asp Gly Thr Thr Ser Val Val Ile Ile
            100                 105                 110

Ala Gly Ser Leu Leu Asp Ser Cys Thr Lys Leu Leu Gln Lys Gly Ile
        115                 120                 125

His Pro Thr Ile Ile Ser Glu Ser Phe Gln Lys Ala Leu Glu Lys Gly
    130                 135                 140

Leu Glu Ile Leu Thr Asp Met Ser Arg Pro Val Gln Leu Ser Asp Arg
145                 150                 155                 160

Glu Thr Leu Leu Asn Ser Ala Thr Thr Ser Leu Asn Ser Lys Val Val
                165                 170                 175

Ser Gln Tyr Ser Ser Leu Leu Ser Pro Met Ser Val Asn Ala Val Met
```

-continued

```
                180             185             190
Lys Val Ile Asp Pro Ala Thr Ala Thr Ser Val Asp Leu Arg Asp Ile
            195             200             205
Lys Ile Val Lys Lys Leu Gly Gly Thr Ile Asp Asp Cys Glu Leu Val
210             215             220
Glu Gly Leu Val Leu Thr Gln Lys Val Ala Asn Ser Gly Ile Thr Arg
225             230             235             240
Val Glu Lys Ala Lys Ile Gly Leu Ile Gln Phe Cys Leu Ser Ala Pro
            245             250             255
Lys Thr Asp Met Asp Asn Gln Ile Val Val Ser Asp Tyr Ala Gln Met
            260             265             270
Asp Arg Val Leu Arg Glu Glu Arg Ala Tyr Ile Leu Asn Leu Val Lys
            275             280             285
Gln Ile Lys Lys Thr Gly Cys Asn Val Leu Leu Ile Gln Lys Ser Ile
            290             295             300
Leu Arg Asp Ala Leu Ser Asp Leu Ala Leu His Phe Leu Asn Lys Met
305             310             315             320
Lys Ile Met Val Val Lys Asp Val Glu Arg Glu Asp Ile Glu Phe Ile
            325             330             335
Cys Lys Thr Ile Gly Thr Lys Pro Val Ala His Ile Asp Gln Phe Thr
            340             345             350
Ala Asp Met Leu Gly Ser Ala Glu Leu Ala Glu Glu Val Ser Leu Asn
            355             360             365
Gly Ser Gly Lys Leu Phe Lys Ile Thr Gly Cys Thr Ser Pro Gly Lys
            370             375             380
Thr Val Thr Ile Val Val Arg Gly Ser Asn Lys Leu Val Ile Glu Glu
385             390             395             400
Ala Glu Arg Ser Ile His Asp Ala Leu Cys Val Ile Arg Cys Leu Val
            405             410             415
Lys Lys Arg Ala Leu Ile Ala Gly Gly Gly Ala Pro Glu Ile Glu Leu
            420             425             430
Ala Leu Arg Leu Thr Glu Tyr Ser Arg Thr Leu Ser Gly Met Glu Ser
            435             440             445
Tyr Cys Val Arg Ala Phe Ala Asp Ala Met Glu Val Ile Pro Ser Thr
            450             455             460
Leu Ala Glu Asn Ala Gly Leu Asn Pro Ile Ser Thr Val Thr Glu Leu
465             470             475             480
Arg Asn Arg His Ala Gln Gly Glu Lys Thr Thr Gly Ile Asn Val Arg
            485             490             495
Lys Gly Gly Ile Ser Asn Ile Leu Glu Glu Met Val Val Gln Pro Leu
            500             505             510
Leu Val Ser Val Ser Ala Leu Thr Leu Ala Thr Glu Thr Val Arg Ser
            515             520             525
Ile Leu Lys Ile Asp Asp Val Val Asn Thr Arg
530             535
```

(2) INFORMATION FOR SEQ ID NO:28:

(i) SEQUENCE CHARACTERISTICS:
        (A) LENGTH: 541 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:28:

```
Met Ala Ser Val Gly Thr Leu Ala Phe Asp Glu Tyr Gly Arg Pro Phe
 1               5                  10                  15

Leu Ile Ile Lys Asp Gln Asp Arg Lys Ser Arg Leu Met Gly Leu Glu
            20                  25                  30

Ala Leu Lys Ser His Ile Met Ala Ala Lys Ala Val Ala Asn Thr Met
        35                  40                  45

Arg Thr Ser Leu Gly Pro Asn Gly Leu Asp Lys Met Met Val Asp Lys
    50                  55                  60

Asp Gly Asp Val Thr Ile Thr Asn Asp Gly Ala Thr Ile Leu Ser Met
65                  70                  75                  80

Met Asp Val Asp His Gln Ile Ala Lys Leu Met Val Glu Leu Ser Lys
                85                  90                  95

Ser Gln Asp Asp Glu Ile Gly Asp Gly Thr Thr Gly Val Val Val Leu
            100                 105                 110

Ala Gly Ala Leu Leu Glu Glu Ala Glu Gln Leu Leu Asp Arg Gly Ile
        115                 120                 125

His Pro Ile Arg Ile Ala Asp Gly Tyr Glu Gln Ala Ala Arg Ile Ala
    130                 135                 140

Ile Gln His Leu Asp Lys Ile Ser Asp Lys Val Leu Val Asp Ile Asn
145                 150                 155                 160

Asn Pro Glu Pro Leu Ile Gln Thr Ala Lys Thr Thr Leu Gly Ser Lys
                165                 170                 175

Val Ile Asn Ser Cys His Arg Gln Met Ala Glu Ile Ala Val Asn Ala
            180                 185                 190

Val Leu Thr Val Ala Asp Met Glu Arg Arg Asp Val Asp Phe Glu Leu
        195                 200                 205

Ile Lys Val Glu Gly Lys Val Gly Gly Arg Leu Glu Asp Thr Lys Leu
    210                 215                 220

Ile Lys Gly Val Ile Val Asp Lys Asp Phe Ser His Pro Gln Met Pro
225                 230                 235                 240

Lys Lys Val Val Asp Ala Lys Ile Ala Ile Leu Thr Cys Pro Phe Glu
                245                 250                 255

Pro Pro Lys Pro Lys Thr Lys His Lys Leu Asp Val Met Ser Val Glu
            260                 265                 270

Asp Tyr Lys Ala Leu Gln Lys Tyr Glu Lys Glu Lys Phe Glu Glu Met
        275                 280                 285

Ile Lys Gln Ile Lys Glu Thr Gly Ala Asn Leu Ala Ile Cys Gln Trp
    290                 295                 300

Gly Phe Asp Asp Glu Ala Asn His Leu Leu Leu Gln Asn Gly Leu Pro
305                 310                 315                 320

Ala Val Arg Trp Val Gly Gly Pro Glu Ile Glu Leu Ile Ala Ile Ala
                325                 330                 335

Thr Gly Gly Arg Ile Val Pro Arg Phe Ser Glu Leu Thr Ser Glu Lys
            340                 345                 350

Leu Gly Phe Ala Gly Val Val Gln Glu Ile Ser Phe Gly Thr Thr Lys
        355                 360                 365

Asp Lys Met Leu Val Ile Glu Lys Cys Lys Asn Ser Arg Ala Val Thr
    370                 375                 380

Ile Phe Ile Arg Gly Gly Asn Lys Met Ile Glu Glu Ala Lys Arg
385                 390                 395                 400

Ser Leu His Asp Ala Leu Cys Val Ile Arg Asn Leu Ile Arg Asp Asn
                405                 410                 415
```

```
Arg Val Val Tyr Gly Gly Ala Ala Glu Ile Ser Cys Ala Leu Ala
            420             425             430

Val Ser Gln Glu Ala Asp Lys Cys Pro Thr Leu Glu Gln Tyr Ala Met
            435             440             445

Arg Ala Phe Ala Asp Ala Leu Glu Val Ile Pro Met Ala Leu Ser Glu
            450             455             460

Asn Ser Gly Met Asn Pro Ile Gln Thr Met Thr Glu Val Arg Ala Arg
465             470             475             480

Gln Val Lys Glu Ser Asn Pro Ala Leu Gly Ile Asp Cys Leu His Lys
            485             490             495

Gly Ser Asn Asp Met Gln Tyr Gln His Val Ile Glu Thr Leu Ile Gly
            500             505             510

Lys Lys Gln Gln Ile Ser Leu Ala Thr Gln Met Val Arg Met Ile Leu
            515             520             525

Lys Ile Asp Asp Ile Arg Lys Pro Gly Glu Ser Glu Glu
            530             535             540
```

(2) INFORMATION FOR SEQ ID NO:29:

(i) SEQUENCE CHARACTERISTICS:
        (A) LENGTH: 531 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:29:

```
Met Ala Ala Val Lys Thr Leu Asn Pro Lys Ala Glu Val Ala Arg Ala
1               5                   10                  15

Gln Ala Ala Leu Ala Val Asn Ile Ser Ala Ala Arg Gly Leu Gln Asp
            20                  25                  30

Val Leu Arg Thr Asn Leu Gly Pro Lys Gly Thr Met Lys Met Leu Val
            35                  40                  45

Ser Gly Ala Gly Asp Ile Lys Leu Thr Lys Asp Gly Asn Val Leu Leu
            50                  55                  60

His Glu Met Gln Ile Gln His Pro Thr Ala Ser Leu Ile Ala Lys Val
65                  70                  75                  80

Ala Thr Ala Gln Asp Asp Ile Thr Gly Asp Gly Thr Thr Ser Asn Val
            85                  90                  95

Leu Ile Ile Gly Glu Leu Leu Lys Gln Ala Asp Leu Tyr Ile Ser Glu
            100                 105                 110

Gly Leu His Pro Arg Ile Ile Thr Glu Gly Phe Glu Ala Ala Lys Glu
            115                 120                 125

Lys Ala Leu Gln Phe Leu Glu Gln Val Lys Val Ser Lys Glu Met Asp
            130                 135                 140

Arg Glu Thr Leu Ile Asp Val Ala Arg Thr Ser Leu Arg Thr Lys Val
145                 150                 155                 160

His Ala Glu Leu Ala Asp Val Leu Thr Glu Ala Val Val Asp Ser Ile
            165                 170                 175

Leu Ala Ile Arg Lys Lys Asp Glu Pro Ile Asp Leu Phe Met Val Glu
            180                 185                 190

Ile Met Glu Met Lys His Lys Ser Glu Thr Asp Thr Ser Leu Ile Arg
            195                 200                 205

Gly Leu Val Leu Asp His Gly Ala Arg His Pro Asp Met Lys Lys Arg
            210                 215                 220
```

-continued

```
Val Glu Asn Ala Tyr Ile Leu Thr Cys Asn Val Ser Leu Glu Tyr Glu
225                 230                 235                 240

Lys Thr Glu Val Asn Ser Gly Phe Phe Tyr Lys Ser Ala Glu Glu Arg
            245                 250                 255

Glu Lys Leu Val Lys Ala Glu Arg Lys Phe Ile Glu Asp Arg Val Lys
        260                 265                 270

Lys Ile Ile Glu Leu Lys Lys Val Cys Gly Asp Ser Asp Lys Gly
    275                 280                 285

Phe Val Val Ile Asn Gln Lys Gly Ile Asp Pro Phe Ser Leu Asp Ala
290                 295                 300

Leu Ala Lys Glu Gly Ile Val Ala Leu Arg Arg Ala Lys Arg Arg Asn
305                 310                 315                 320

Met Glu Arg Leu Thr Leu Ala Cys Gly Gly Ile Ala Leu Asn Ser Phe
                325                 330                 335

Asp Asp Leu Asn Pro Asp Cys Leu Gly His Ala Gly Leu Val Tyr Glu
                340                 345                 350

Tyr Thr Leu Gly Glu Glu Lys Phe Thr Phe Ile Glu Lys Cys Asn Asn
            355                 360                 365

Pro Arg Ser Val Thr Leu Leu Val Lys Gly Pro Asn Lys His Thr Leu
        370                 375                 380

Thr Gln Ile Lys Asp Ala Ile Arg Asp Gly Leu Arg Ala Val Lys Asn
385                 390                 395                 400

Ala Ile Asp Asp Gly Cys Val Val Pro Gly Ala Gly Ala Val Glu Val
                405                 410                 415

Ala Leu Ala Glu Ala Leu Ile Lys Tyr Lys Pro Ser Val Lys Gly Arg
            420                 425                 430

Ala Gln Leu Gly Val Gln Ala Phe Ala Asp Ala Leu Leu Ile Ile Pro
        435                 440                 445

Lys Val Leu Ala Gln Asn Ser Gly Phe Asp Leu Gln Glu Thr Leu Val
    450                 455                 460

Lys Val Gln Ala Glu His Ser Glu Ser Gly Gln Leu Val Gly Val Asp
465                 470                 475                 480

Leu Ser Thr Gly Glu Pro Met Val Ala Ala Glu Met Gly Val Trp Asp
                485                 490                 495

Asn Tyr Cys Val Lys Lys Gln Leu Leu His Ser Cys Thr Val Ile Ala
            500                 505                 510

Thr Asn Ile Leu Leu Val Asp Glu Ile Met Arg Ala Gly Met Ser Ser
        515                 520                 525

Leu Lys Gly
    530
```

(2) INFORMATION FOR SEQ ID NO:30:

(i) SEQUENCE CHARACTERISTICS:
        (A) LENGTH: 544 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:30:

```
Met Met Pro Thr Pro Val Ile Leu Leu Lys Glu Gly Thr Asp Ser Ser
1               5                   10                  15

Gln Gly Ile Pro Gln Leu Val Ser Asn Ile Ser Ala Cys Gln Val Ile
            20                  25                  30
```

-continued

```
Ala Glu Ala Val Arg Thr Thr Leu Gly Pro Arg Gly Met Asp Lys Leu
         35                  40                  45

Ile Val Asp Gly Arg Gly Lys Ala Thr Ile Ser Asn Asp Gly Ala Thr
 50                  55                  60

Ile Leu Lys Leu Leu Asp Val His Pro Ala Ala Lys Thr Leu Val
65                  70                  75                  80

Asp Ile Ala Lys Ser Gln Asp Ala Glu Val Gly Asp Gly Thr Thr Ser
                 85                  90                  95

Val Thr Leu Leu Ala Ala Glu Phe Leu Lys Gln Val Lys Pro Tyr Val
                100                 105                 110

Glu Glu Gly Leu His Pro Gln Ile Ile Ile Arg Ala Phe Arg Thr Ala
            115                 120                 125

Thr Gln Leu Ala Val Asn Lys Ile Lys Glu Ile Ala Val Thr Val Lys
    130                 135                 140

Lys Gln Asp Lys Val Glu Gln Arg Lys Met Leu Glu Lys Cys Ala Met
145                 150                 155                 160

Thr Ala Leu Ser Ser Lys Leu Ile Ser Gln Gln Lys Val Phe Phe Ala
                165                 170                 175

Lys Met Val Val Asp Ala Val Met Met Leu Asp Glu Leu Leu Gln Leu
                180                 185                 190

Lys Met Ile Gly Ile Lys Lys Val Gln Gly Gly Ala Leu Glu Glu Ser
            195                 200                 205

Gln Leu Val Ala Gly Val Ala Phe Lys Lys Thr Phe Ser Tyr Ala Gly
    210                 215                 220

Phe Glu Met Gln Pro Lys Lys Tyr Lys Asn Pro Lys Ile Ala Leu Leu
225                 230                 235                 240

Asn Val Glu Leu Glu Leu Lys Ala Glu Lys Asp Asn Ala Glu Ile Arg
                245                 250                 255

Val His Thr Val Glu Asp Tyr Gln Ala Ile Val Asp Ala Glu Trp Asn
                260                 265                 270

Ile Leu Tyr Asp Lys Leu Glu Lys Ile His Gln Ser Gly Ala Lys Val
            275                 280                 285

Ile Leu Ser Lys Leu Pro Ile Gly Asp Val Ala Thr Gln Tyr Phe Ala
    290                 295                 300

Asp Arg Asp Met Phe Cys Ala Gly Arg Val Pro Glu Glu Asp Leu Lys
305                 310                 315                 320

Arg Thr Met Met Ala Cys Gly Gly Ser Ile Gln Thr Ser Val Asn Ala
                325                 330                 335

Leu Val Pro Asp Val Leu Gly His Cys Gln Val Phe Glu Glu Thr Gln
                340                 345                 350

Ile Gly Gly Glu Arg Tyr Asn Phe Phe Thr Gly Cys Pro Lys Ala Lys
            355                 360                 365

Thr Cys Thr Ile Ile Leu Arg Gly Gly Ala Glu Gln Phe Met Glu Glu
    370                 375                 380

Thr Glu Arg Ser Leu His Asp Ala Ile Met Ile Val Arg Arg Ala Ile
385                 390                 395                 400

Lys Asn Asp Ser Val Val Ala Gly Gly Ala Ile Glu Met Glu Leu
                405                 410                 415

Ser Lys Tyr Leu Arg Asp Tyr Ser Arg Thr Ile Pro Gly Lys Gln Gln
            420                 425                 430

Leu Leu Ile Gly Ala Tyr Ala Lys Ala Leu Glu Ile Ile Pro Arg Gln
    435                 440                 445
```

```
Leu Cys Asp Asn Ala Gly Phe Asp Ala Thr Asn Ile Leu Asn Lys Leu
    450                 455                 460

Arg Ala Arg His Ala Gln Gly Gly Met Trp Tyr Gly Val Asp Ile Asn
465                 470                 475                 480

Asn Glu Asn Ile Ala Asp Asn Phe Gln Ala Phe Val Trp Glu Pro Ala
                485                 490                 495

Met Val Arg Ile Asn Ala Leu Thr Ala Ala Ser Glu Ala Ala Cys Leu
                500                 505                 510

Ile Val Ser Val Asp Glu Thr Ile Lys Asn Pro Arg Ser Thr Val Asp
            515                 520                 525

Pro Pro Ala Pro Ser Ala Gly Arg Gly Arg Gly Gln Ala Arg Phe His
530                 535                 540

(2) INFORMATION FOR SEQ ID NO:31:

(i) SEQUENCE CHARACTERISTICS:
        (A) LENGTH: 548 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:31:

Met Ala Leu His Val Pro Lys Ala Pro Gly Phe Ala Gln Met Leu Lys
1               5                   10                  15

Asp Gly Ala Lys His Phe Ser Gly Leu Glu Glu Ala Val Tyr Arg Asn
                20                  25                  30

Ile Gln Ala Cys Lys Glu Leu Ala Gln Thr Thr Arg Thr Ala Tyr Gly
            35                  40                  45

Pro Asn Gly Met Asn Lys Met Val Ile Asn Arg Leu Glu Lys Leu Phe
50                  55                  60

Val Thr Asn Asp Ala Ala Thr Ile Leu Arg Glu Leu Glu Val Gln His
65                  70                  75                  80

Pro Ala Ala Lys Met Ile Val Met Ala Ser His Met Gln Glu Gln Glu
                85                  90                  95

Val Gly Asp Gly Thr Asn Phe Val Leu Val Phe Ala Gly Ala Leu Leu
                100                 105                 110

Glu Leu Ala Glu Glu Leu Leu Arg Ile Gly Leu Ser Val Ser Glu Val
        115                 120                 125

Ile Ser Gly Tyr Glu Ile Ala Cys Lys Lys Ala His Glu Ile Leu Pro
130                 135                 140

Glu Leu Val Cys Cys Ser Ala Lys Asn Leu Arg Asp Val Asp Glu Val
145                 150                 155                 160

Ser Ser Leu Leu Arg Thr Ser Ile Met Ser Lys Gln Tyr Gly Ser Glu
                165                 170                 175

Thr Phe Leu Ala Lys Leu Ile Ala Gln Ala Cys Val Ser Ile Phe Pro
            180                 185                 190

Asp Ser Gly Asn Phe Asn Val Asp Asn Ile Arg Val Cys Lys Ile Leu
            195                 200                 205

Gly Ser Gly Ile Tyr Ser Ser Val Leu His Gly Met Val Phe Lys
            210                 215                 220

Lys Glu Thr Glu Gly Asp Val Thr Ser Val Lys Asp Ala Lys Ile Ala
225                 230                 235                 240

Val Tyr Ser Cys Pro Phe Asp Gly Met Ile Thr Glu Thr Lys Gly Thr
                245                 250                 255
```

```
Val Leu Ile Lys Thr Ala Glu Glu Leu Met Asn Phe Ser Lys Gly Glu
            260                 265                 270

Glu Asn Leu Met Asp Ala Gln Val Lys Ala Ile Ala Gly Thr Gly Ala
            275                 280                 285

Asn Val Ile Val Thr Gly Gly Lys Val Ala Asp Ile Ala Leu His Tyr
            290                 295                 300

Ala Asn Lys Tyr Asn Ile Met Leu Val Arg Leu Asn Ser Lys Trp Asp
305                 310                 315                 320

Leu Arg Arg Leu Cys Lys Thr Val Gly Ala Thr Ala Leu Pro Lys Leu
                325                 330                 335

Thr Pro Pro Val Gln Glu Met Gly His Cys Asp Ser Val Tyr Leu
            340                 345                 350

Ser Glu Val Gly Asp Thr Gln Val Val Phe Lys His Glu Lys Glu
            355                 360                 365

Asp Gly Ala Ile Ser Thr Ile Val Leu Arg Gly Ser Thr Asp Asn Leu
            370                 375                 380

Met Asp Asp Ile Glu Arg Ala Val Asp Asp Gly Val Asn Thr Phe Lys
385                 390                 395                 400

Val Leu Thr Arg Asp Lys Arg Leu Val Pro Gly Gly Ala Thr Glu
                405                 410                 415

Ile Glu Leu Ala Lys Gln Ile Thr Ser Tyr Gly Glu Thr Cys Pro Gly
            420                 425                 430

Leu Glu Gln Tyr Ala Ile Lys Lys Phe Ala Glu Ala Phe Glu Ala Ile
                435                 440                 445

Pro Arg Ala Leu Ala Glu Asn Ser Gly Val Lys Ala Asn Glu Val Ile
    450                 455                 460

Ser Lys Leu Tyr Ser Val His Gln Glu Gly Asn Lys Asn Val Gly Leu
465                 470                 475                 480

Asp Ile Glu Ala Glu Val Pro Ala Val Lys Asp Met Leu Glu Ala Ser
                485                 490                 495

Ile Leu Asp Thr Tyr Leu Gly Lys Tyr Trp Ala Ile Lys Leu Ala Thr
                500                 505                 510

Asn Ala Ala Val Thr Val Leu Arg Val Asp Gln Ile Ile Met Ala Lys
    515                 520                 525

Pro Ala Gly Gly Pro Lys Pro Pro Ser Gly Lys Lys Asp Trp Asp Asp
    530                 535                 540

Asp Gln Asn Asp
545

(2) INFORMATION FOR SEQ ID NO:32:

(i) SEQUENCE CHARACTERISTICS:
        (A) LENGTH: 552 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:32:

Met Ala Thr Ala Thr Val Ala Thr Thr Pro Glu Gly Ile Pro Val Ile
1               5                   10                  15

Ile Leu Lys Glu Gly Ser Ser Arg Thr Tyr Gly Lys Glu Ala Leu Arg
                20                  25                  30

Ala Asn Ile Ala Ala Val Lys Ala Ile Glu Glu Ala Leu Lys Ser Thr
                35                  40                  45
```

-continued

Tyr Gly Pro Arg Gly Met Asp Lys Met Phe Val Asp Ser Leu Gly Asp
    50                  55                  60

Ile Thr Ile Thr Asn Asp Gly Ala Thr Ile Leu Asp Lys Met Asp Leu
65                  70                  75                  80

Gln His Pro Thr Gly Lys Leu Leu Val Gln Ile Ala Lys Gly Gln Asp
                85                  90                  95

Glu Glu Thr Ala Asp Gly Thr Lys Thr Ala Val Ile Leu Ala Gly Glu
            100                 105                 110

Leu Ala Lys Lys Ala Glu Asp Leu Leu Tyr Lys Glu Ile His Pro Thr
            115                 120                 125

Ile Ile Val Ser Gly Tyr Lys Lys Ala Glu Glu Ile Ala Leu Lys Thr
        130                 135                 140

Ile Gln Asp Ile Ala Gln Pro Val Ser Ile Asn Asp Thr Asp Val Leu
145                 150                 155                 160

Arg Lys Val Ala Leu Thr Ser Leu Gly Ser Lys Ala Val Ala Gly Ala
                165                 170                 175

Arg Glu Tyr Leu Ala Asp Leu Val Val Lys Ala Val Ala Gln Val Ala
            180                 185                 190

Glu Leu Arg Gly Asp Lys Trp Tyr Val Asp Leu Asp Asn Val Gln Ile
        195                 200                 205

Val Lys Lys His Gly Gly Ser Ile Asn Asp Thr Gln Leu Val Tyr Gly
    210                 215                 220

Ile Val Val Asp Lys Glu Val Val His Pro Gly Met Pro Lys Arg Ile
225                 230                 235                 240

Glu Asn Ala Lys Ile Ala Leu Leu Asp Ala Ser Leu Glu Val Glu Lys
                245                 250                 255

Pro Glu Leu Asp Ala Glu Ile Arg Ile Asn Asp Pro Thr Gln Met His
            260                 265                 270

Lys Phe Leu Glu Glu Glu Glu Asn Ile Leu Lys Glu Lys Val Asp Lys
        275                 280                 285

Ile Ala Ala Thr Gly Ala Asn Val Val Ile Cys Gln Lys Gly Ile Asp
    290                 295                 300

Glu Val Ala Gln His Tyr Leu Ala Lys Lys Gly Ile Leu Ala Val Arg
305                 310                 315                 320

Arg Ala Lys Lys Ser Asp Leu Glu Lys Leu Ala Arg Ala Thr Gly Gly
                325                 330                 335

Arg Val Ile Ser Asn Ile Asp Glu Leu Thr Ser Gln Asp Leu Gly Tyr
            340                 345                 350

Ala Ala Leu Val Glu Glu Arg Lys Val Gly Glu Asp Lys Met Val Phe
        355                 360                 365

Val Glu Gly Ala Lys Asn Pro Lys Ser Val Ser Ile Leu Ile Arg Gly
    370                 375                 380

Gly Leu Glu Arg Val Val Asp Glu Thr Glu Arg Ala Leu Arg Asp Ala
385                 390                 395                 400

Leu Gly Thr Val Ala Asp Val Ile Arg Asp Gly Arg Ala Val Ala Gly
                405                 410                 415

Gly Gly Ala Val Glu Ile Glu Ile Ala Lys Arg Leu Arg Lys Tyr Ala
            420                 425                 430

Pro Gln Val Gly Gly Lys Glu Gln Leu Ala Ile Glu Ala Tyr Ala Asn
        435                 440                 445

Ala Ile Glu Gly Leu Ile Met Ile Leu Ala Glu Asn Ala Gly Leu Asp
    450                 455                 460

Pro Ile Asp Lys Leu Met Gln Leu Arg Ser Leu His Glu Asn Glu Thr

```
              465                 470                 475                 480
Asn Lys Trp Tyr Gly Leu Asn Leu Phe Thr Gly Asn Pro Glu Asp Met
                    485                 490                 495
Trp Lys Leu Gly Val Ile Glu Pro Ala Leu Val Lys Met Asn Ala Ile
            500                 505                 510
Lys Ala Ala Thr Glu Ala Val Thr Leu Val Leu Arg Ile Asp Asp Ile
        515                 520                 525
Val Ala Ala Gly Lys Lys Gly Gly Ser Glu Pro Gly Gly Lys Lys Glu
    530                 535                 540
Lys Glu Glu Lys Ser Ser Glu Asp
545                 550
```

(2) INFORMATION FOR SEQ ID NO:33:

(i) SEQUENCE CHARACTERISTICS:
      (A) LENGTH: 590 amino acids
      (B) TYPE: amino acid
      (C) STRANDEDNESS: single
      (D) TOPOLOGY: linear (ii) MOLECULE TYPE: peptide (ix) FEATURE:
      (B) LOCATION: 1..590
      (D) OTHER INFORMATION: /label= consensus
          /note= "All locations where there is no
          consensus are designated Xaa"

(ix) FEATURE:
      (B) LOCATION: 22
      (D) OTHER INFORMATION: /note= "Ser may be Lys"

(ix) FEATURE:
      (B) LOCATION: 34
      (D) OTHER INFORMATION: /note= "Leu may be Arg"

(ix) FEATURE:
      (B) LOCATION: 49
      (D) OTHER INFORMATION: /note= "Arg may be Lys"

(ix) FEATURE:
      (B) LOCATION: 50
      (D) OTHER INFORMATION: /note= "Thr may be Ser"

(ix) FEATURE:
      (B) LOCATION: 51
      (D) OTHER INFORMATION: /note= "Ser may be Thr"

(ix) FEATURE:
      (B) LOCATION: 70
      (D) OTHER INFORMATION: /note= "Val may be Ile"

(ix) FEATURE:
      (B) LOCATION: 83
      (D) OTHER INFORMATION: /note= "Leu may be Met"

(ix) FEATURE:
      (B) LOCATION: 84
      (D) OTHER INFORMATION: /note= "Gln may be Asp"

(ix) FEATURE:
      (B) LOCATION: 96
      (D) OTHER INFORMATION: /note= "Leu may be Ile"

(ix) FEATURE:
      (B) LOCATION: 97
      (D) OTHER INFORMATION: /note= "Ala may be Ser"

(ix) FEATURE:
      (B) LOCATION: 113
      (D) OTHER INFORMATION: /note= "Ile may be Val"

(ix) FEATURE:

```
        (B) LOCATION: 116
        (D) OTHER INFORMATION: /note= "Gly may be Ala"

(ix) FEATURE:
        (B) LOCATION: 135
        (D) OTHER INFORMATION: /note= "Ile may be Val"

(ix) FEATURE:
        (B) LOCATION: 139
        (D) OTHER INFORMATION: /note= "Tyr may be Phe"

(ix) FEATURE:
        (B) LOCATION: 140
        (D) OTHER INFORMATION: /note= "Arg may be Glu"

(ix) FEATURE:
        (B) LOCATION: 144
        (D) OTHER INFORMATION: /note= "Glu may be Lys"

(ix) FEATURE:
        (B) LOCATION: 150
        (D) OTHER INFORMATION: /note= "Leu may be Ile"

(ix) FEATURE:
        (B) LOCATION: 154
        (D) OTHER INFORMATION: /note= "Ala may be Ser"

(ix) FEATURE:
        (B) LOCATION: 160
        (D) OTHER INFORMATION: /note= "Asp may be Asn"

(ix) FEATURE:
        (B) LOCATION: 189
        (D) OTHER INFORMATION: /note= "Leu may be Phe"

(ix) FEATURE:
        (B) LOCATION: 192
        (D) OTHER INFORMATION: /note= "Met may be Ile"

(ix) FEATURE:
        (B) LOCATION: 193
        (D) OTHER INFORMATION: /note= "Val may be Ala"

(ix) FEATURE:
        (B) LOCATION: 218
        (D) OTHER INFORMATION: /note= "Ile may be Val"

(ix) FEATURE:
        (B) LOCATION: 232
        (D) OTHER INFORMATION: /note= "Val may be Ile"

(ix) FEATURE:
        (B) LOCATION: 253
        (D) OTHER INFORMATION: /note= "Ile may be Val"

(ix) FEATURE:
        (B) LOCATION: 271
        (D) OTHER INFORMATION: /note= "Glu may be Lys"

(ix) FEATURE:
        (B) LOCATION: 277
        (D) OTHER INFORMATION: /note= "Ile may be Val"

(ix) FEATURE:
        (B) LOCATION: 279
        (D) OTHER INFORMATION: /note= "Val may be Ile"

(ix) FEATURE:
        (B) LOCATION: 297
        (D) OTHER INFORMATION: /note= "Glu may be Lys"

(ix) FEATURE:
        (B) LOCATION: 353
        (D) OTHER INFORMATION: /note= "Ile may be Leu"

(ix) FEATURE:
        (B) LOCATION: 359
        (D) OTHER INFORMATION: /note= "Gly may be Ala"
```

```
(ix) FEATURE:
    (B) LOCATION: 371
    (D) OTHER INFORMATION: /note= "Asp may be Glu"

(ix) FEATURE:
    (B) LOCATION: 379
    (D) OTHER INFORMATION: /note= "Ala may be Cys"

(ix) FEATURE:
    (B) LOCATION: 389
    (D) OTHER INFORMATION: /note= "Glu may be Gly"

(ix) FEATURE:
    (B) LOCATION: 404
    (D) OTHER INFORMATION: /note= "Pro may be Gly"

(ix) FEATURE:
    (B) LOCATION: 406
    (D) OTHER INFORMATION: /note= "Ala may be Ser"

(ix) FEATURE:
    (B) LOCATION: 407
    (D) OTHER INFORMATION: /note= "Val may be Cys"

(ix) FEATURE:
    (B) LOCATION: 414
    (D) OTHER INFORMATION: /note= "Ala may be Gly"

(ix) FEATURE:
    (B) LOCATION: 420
    (D) OTHER INFORMATION: /note= "Asp may be Glu"

(ix) FEATURE:
    (B) LOCATION: 434
    (D) OTHER INFORMATION: /note= "Arg may be Lys"

(ix) FEATURE:
    (B) LOCATION: 437
    (D) OTHER INFORMATION: /note= "Ile may be Leu"

(ix) FEATURE:
    (B) LOCATION: 444
    (D) OTHER INFORMATION: /note= "Ala may be Pro"

(ix) FEATURE:
    (B) LOCATION: 451
    (D) OTHER INFORMATION: /note= "Ile may be Met"

(ix) FEATURE:
    (B) LOCATION: 470
    (D) OTHER INFORMATION: /note= "Leu may be Tyr"

(ix) FEATURE:
    (B) LOCATION: 490
    (D) OTHER INFORMATION: /note= "Ala may be Ser"

(ix) FEATURE:
    (B) LOCATION: 497
    (D) OTHER INFORMATION: /note= "Thr may be Leu"

(ix) FEATURE:
    (B) LOCATION: 498
    (D) OTHER INFORMATION: /note= "Val may be Leu"

(ix) FEATURE:
    (B) LOCATION: 519
    (D) OTHER INFORMATION: /note= "Thr may be Trp"

(ix) FEATURE:
    (B) LOCATION: 522
    (D) OTHER INFORMATION: /note= "Val may be Leu or Ile"

(ix) FEATURE:
    (B) LOCATION: 523
    (D) OTHER INFORMATION: /note= "Asp may be Asn"

(ix) FEATURE:
    (B) LOCATION: 535
    (D) OTHER INFORMATION: /note= "Leu may be Ala"
```

```
    (ix) FEATURE:
         (B) LOCATION: 537
         (D) OTHER INFORMATION: /note= "Val may be Ile"

(ix) FEATURE:
         (B) LOCATION: 548
         (D) OTHER INFORMATION: /note= "Leu may be Ile"

(ix) FEATURE:
         (B) LOCATION: 561
         (D) OTHER INFORMATION: /note= "Ile may be Val"

(ix) FEATURE:
         (B) LOCATION: 565
         (D) OTHER INFORMATION: /note= "Val may be Ile"

(xi) SEQUENCE DESCRIPTION: SEQ ID NO:33:
```

Xaa Xaa Xaa Xaa Xaa Xaa Xaa Xaa Xaa Xaa Xaa Xaa Xaa Xaa Xaa
 1               5                   10                  15

Pro Val Ile Ile Leu Ser Xaa Gly Xaa Asp Arg Ser Xaa Gly Glu Glu
                20                  25                  30

Ala Leu Xaa Ser Asn Ile Ser Ala Ala Lys Ala Ile Ala Asp Ala Val
            35                  40                  45

Arg Thr Ser Leu Gly Pro Lys Gly Met Asp Lys Met Leu Val Asp Gly
        50                  55                  60

Xaa Gly Asp Xaa Xaa Val Thr Ile Thr Asn Asp Gly Ala Thr Ile Leu
65                  70                  75                  80

Lys Glu Leu Gln Val Gln His Pro Ala Ala Lys Leu Leu Val Glu Leu
                85                  90                  95

Ala Lys Xaa Gln Asp Asp Glu Val Gly Asp Gly Thr Thr Ser Val Val
            100                 105                 110

Ile Leu Ala Gly Glu Leu Leu Lys Xaa Ala Glu Xaa Leu Leu Xaa Lys
        115                 120                 125

Gly Ile His Pro Thr Ile Ile Ile Ser Gly Tyr Arg Xaa Ala Xaa Glu
        130                 135                 140

Lys Ala Leu Xaa Thr Leu Xaa Glu Ile Ala Xaa Pro Val Xaa Xaa Asp
145                 150                 155                 160

Asp Arg Xaa Xaa Xaa Xaa Xaa Met Leu Ile Asn Xaa Ala Xaa Thr Ser
                165                 170                 175

Leu Ser Ser Lys Val Ile Ser Xaa Xaa Xaa Asp Leu Leu Ala Xaa Met
            180                 185                 190

Val Val Asp Ala Val Leu Xaa Val Xaa Xaa Xaa Xaa Xaa Xaa Xaa Lys
        195                 200                 205

Glu Xaa Val Asp Leu Xaa Xaa Ile Xaa Ile Xaa Lys Lys Leu Gly Gly
        210                 215                 220

Ser Ile Xaa Asp Ser Xaa Leu Val Xaa Gly Val Val Leu Asp Lys Xaa
225                 230                 235                 240

Val Xaa His Pro Gly Xaa Xaa Xaa Met Pro Lys Arg Ile Glu Asn Ala
                245                 250                 255

Lys Ile Ala Leu Leu Asn Xaa Ser Leu Glu Xaa Lys Xaa Glu Leu
            260                 265                 270

Xaa Lys Xaa Xaa Ile Arg Val Xaa Asp Xaa Glu Xaa Xaa Xaa Xaa Ile
        275                 280                 285

Xaa Lys Ala Glu Xaa Xaa Ile Met Glu Glu Lys Val Lys Lys Ile Leu
        290                 295                 300

Xaa Thr Gly Ala Asn Val Ile Leu Xaa Gln Xaa Xaa Xaa Xaa Xaa Xaa
305                 310                 315                 320

-continued

```
Ile Xaa Xaa Lys Gly Ile Asp Asp Xaa Ala Leu His Tyr Leu Ala Lys
            325                 330                 335

Ala Gly Ile Met Ala Val Arg Arg Val Xaa Lys Xaa Asp Leu Glu Arg
            340                 345                 350

Ile Ala Lys Ala Cys Gly Gly Arg Ile Val Ser Xaa Phe Asp Glu Leu
            355                 360                 365

Thr Xaa Asp Xaa Xaa Xaa Leu Gly His Ala Gly Leu Val Glu Glu
        370                 375                 380

Val Xaa Xaa Gly Glu Asp Lys Xaa Xaa Xaa Phe Xaa Phe Ile Glu Gly
385                 390                 395                 400

Cys Lys Asn Pro Lys Ala Val Thr Ile Leu Leu Arg Gly Ala Asn Lys
                405                 410                 415

Xaa Ile Leu Asp Glu Ala Glu Arg Ser Leu His Asp Ala Leu Cys Val
            420                 425                 430

Val Arg Asn Val Ile Lys Asp Xaa Arg Val Val Ala Gly Gly Gly Ala
            435                 440                 445

Val Glu Ile Glu Leu Ala Lys Ala Leu Thr Xaa Tyr Ala Xaa Thr Xaa
            450                 455                 460

Pro Gly Lys Glu Gln Leu Ala Ile Arg Ala Phe Ala Asp Ala Leu Glu
465                 470                 475                 480

Val Ile Pro Arg Thr Leu Ala Glu Asn Ala Gly Xaa Asp Pro Ile Asp
                485                 490                 495

Thr Val Thr Lys Leu Arg Ala Xaa His Xaa Glu Xaa Xaa Xaa Xaa Xaa
                500                 505                 510

Xaa Xaa Glu Gly Asn Lys Thr Xaa Gly Val Asp Leu Xaa Thr Gly Xaa
            515                 520                 525

Pro Xaa Asp Met Xaa Glu Leu Gly Val Trp Glu Pro Leu Leu Val Lys
530                 535                 540

Xaa Gln Ala Leu Lys Leu Ala Thr Glu Ala Ala Xaa Leu Ile Leu Arg
545                 550                 555                 560

Ile Asp Asp Ile Val Lys Ala Gly Pro Ser Xaa Gly Asp Xaa Xaa Xaa
                565                 570                 575

Xaa Xaa Xaa Xaa Xaa Xaa Xaa Xaa Xaa Xaa Xaa Xaa Xaa
            580                 585                 590
```

(2) INFORMATION FOR SEQ ID NO:34:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:34:

```
Lys Glu Val Gly Asp Gly Thr Thr Ser Val Val Ile Ile Ala
1               5                   10
```

(2) INFORMATION FOR SEQ ID NO:35:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:35:

Asp Glu Val Gly Asp Gly Thr Thr Ser Val Thr Val Leu Ala
1               5                   10

(2) INFORMATION FOR SEQ ID NO:36:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:36:

Glu Glu Val Gly Asp Gly Thr Thr Ser Val Ile Ile Leu Ala
1               5                   10

(2) INFORMATION FOR SEQ ID NO:37:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:37:

Ile Glu Ala Gly Asp Gly Thr Thr Ser Val Val Ile Ile Ala
1               5                   10

(2) INFORMATION FOR SEQ ID NO:38:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:38:

Asp Glu Ile Gly Asp Gly Thr Thr Gly Val Val Val Leu Ala
1               5                   10

(2) INFORMATION FOR SEQ ID NO:39:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:39:

Asp Ile Thr Gly Asp Gly Thr Thr Ser Asn Val Leu Ile Ile
1               5                   10

(2) INFORMATION FOR SEQ ID NO:40:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:40:

Ala Glu Val Gly Asp Gly Thr Thr Ser Val Thr Leu Leu Ala
1               5                  10

(2) INFORMATION FOR SEQ ID NO:41:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:41:

Gln Glu Val Gly Asp Gly Thr Asn Phe Val Leu Val Phe Ala
1               5                  10

(2) INFORMATION FOR SEQ ID NO:42:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:42:

Lys Thr Leu Gly Thr Gly Ser Phe Gly Arg Val Met Leu Val
1               5                  10

(2) INFORMATION FOR SEQ ID NO:43:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:43:

Met Val Leu Gly Lys Gly Ser Phe Gly Lys Val Met Leu Ala
1               5                  10

(2) INFORMATION FOR SEQ ID NO:44:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:44:

Glu Glu Leu Gly Lys Gly Ala Phe Ser Val Val Arg Arg Cys
1               5                  10

(2) INFORMATION FOR SEQ ID NO:45:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:45:

Lys Thr Leu Gly Glu Gly Ser Phe Gly Lys Val Lys Leu Ala
1               5                   10

(2) INFORMATION FOR SEQ ID NO:46:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:46:

Glu Lys Ile Gly Glu Gly Thr Tyr Gly Val Val Tyr Lys Ala
1               5                   10

(2) INFORMATION FOR SEQ ID NO:47:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:47:

Asp Lys Ile Gly Glu Gly Thr Phe Ser Ser Val Tyr Lys Ala
1               5                   10

(2) INFORMATION FOR SEQ ID NO:48:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:48:

Thr Arg Ile Gly Ser Gly Ser Phe Gly Thr Val Tyr Lys Gly
1               5                   10

(2) INFORMATION FOR SEQ ID NO:49:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:49:

Val Lys Leu Gly Gln Gly Cys Phe Gly Glu Val Trp Met Gly
1               5                   10

(2) INFORMATION FOR SEQ ID NO:50:

(i) SEQUENCE CHARACTERISTICS:
        (A) LENGTH: 14 amino acids
        (B) TYPE: amino acid
        (C) STRANDEDNESS: single
        (D) TOPOLOGY: linear -continued (ii) MOLECULE TYPE: peptide (xi) SEQUENCE DESCRIPTION: SEQ ID NO:50:

His Lys Leu Gly Gly Gly Gln Tyr Gly Glu Val Tyr Glu Gly
1               5                   10

(2) INFORMATION FOR SEQ ID NO:51:

(i) SEQUENCE CHARACTERISTICS:
            (A) LENGTH: 14 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:51:

Lys Val Leu Gly Ser Gly Ala Phe Gly Thr Val Tyr Lys Gly
1               5                   10

(2) INFORMATION FOR SEQ ID NO:52:

(i) SEQUENCE CHARACTERISTICS:
            (A) LENGTH: 14 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:52:

Arg Glu Leu Gly Gln Gly Ser Phe Gly Met Val Tyr Glu Gly
1               5                   10

(2) INFORMATION FOR SEQ ID NO:53:

(i) SEQUENCE CHARACTERISTICS:
            (A) LENGTH: 14 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:53:

Arg Thr Leu Gly Ser Gly Ala Phe Gly Gln Val Val Glu Ala
1               5                   10

(2) INFORMATION FOR SEQ ID NO:54:

(i) SEQUENCE CHARACTERISTICS:
            (A) LENGTH: 1812 base pairs
            (B) TYPE: nucleic acid
            (C) STRANDEDNESS: single
            (D) TOPOLOGY: linear (ii) MOLECULE TYPE: cDNA (ix) FEATURE:
            (A) NAME/KEY: CDS
            (B) LOCATION: 61..1731

(xi) SEQUENCE DESCRIPTION: SEQ ID NO:54:

TCTCAGAGCG GAGCTATCGG TTGTCTGCGG CCGTAGTGAG CTTTGCTTCG TTTCCTGAAG       60

ATG GAG GGT CCT TTG TCC GTG TTC GGG GAC CGC AGC ACT GGG GAG GCG       108
Met Glu Gly Pro Leu Ser Val Phe Gly Asp Arg Ser Thr Gly Glu Ala
  1               5                  10                  15

GTC CGC TCC CAG AAT GTT ATG GCT GCA GCT TCT ATT GCC AAC ATT GTT       156

-continued

```
Val Arg Ser Gln Asn Val Met Ala Ala Ser Ile Ala Asn Ile Val
         20                  25                  30

AAA AGT TCT TTT GGG CCA GTT GGC TTG GAT AAA ATG TTG GTG GAT GAT      204
Lys Ser Ser Phe Gly Pro Val Gly Leu Asp Lys Met Leu Val Asp Asp
         35                  40                  45

ATT GGT GAT GTA ACC ATT ACT AAC GAT GGT GCC ACC ATC CTG AAG TTA      252
Ile Gly Asp Val Thr Ile Thr Asn Asp Gly Ala Thr Ile Leu Lys Leu
 50                  55                  60

CTG GAG GTA GAA CAT CCC GCA GCC AAA GTT CTG TGT GAG CTG GCT GAC      300
Leu Glu Val Glu His Pro Ala Ala Lys Val Leu Cys Glu Leu Ala Asp
 65                  70                  75                  80

CTG CAA GAC AAA GAA GTT GGA GAT GGA ACT ACC TCA GTG GTA ATC ATT      348
Leu Gln Asp Lys Glu Val Gly Asp Gly Thr Thr Ser Val Val Ile Ile
             85                  90                  95

GCA GCG GAG CTT CTG AAA AAT GCA GAT GAG CTA GTC AAA CAG AAA ATT      396
Ala Ala Glu Leu Leu Lys Asn Ala Asp Glu Leu Val Lys Gln Lys Ile
            100                 105                 110

CAT CCA ACA TCA GTT ATT AGT GGC TAT CGT CTT GCC TGC AAG GAA GCG      444
His Pro Thr Ser Val Ile Ser Gly Tyr Arg Leu Ala Cys Lys Glu Ala
            115                 120                 125

GTG CGT TAT ATC AAT GAG AAC CTG ATT ATT AAC ACA GAC GAA CTT GGA      492
Val Arg Tyr Ile Asn Glu Asn Leu Ile Ile Asn Thr Asp Glu Leu Gly
        130                 135                 140

AGA GAC TGT CTG ATC AAT ACT GCT AAG ACA TCC ATG TCT TCC AAA ATT      540
Arg Asp Cys Leu Ile Asn Thr Ala Lys Thr Ser Met Ser Ser Lys Ile
145                 150                 155                 160

ATT GGA ATA AAT GGT GAT TAC TTT GCT AAT ATG GTA GTA GAT GCT GTG      588
Ile Gly Ile Asn Gly Asp Tyr Phe Ala Asn Met Val Val Asp Ala Val
                165                 170                 175

CTT GCT GTT AAA TAC ACA GAT GCC AGA GGC CAG CCT CGC TAT CCA GTC      636
Leu Ala Val Lys Tyr Thr Asp Ala Arg Gly Gln Pro Arg Tyr Pro Val
            180                 185                 190

AAT TCT GTT AAT ATT CTG AAA GCC CAT GGG AGA AGT CAG ATA GAA AGC      684
Asn Ser Val Asn Ile Leu Lys Ala His Gly Arg Ser Gln Ile Glu Ser
            195                 200                 205

ATG CTG ATC AAT GGC TAT GCG CTC AAT TGT GTG GTT GGA TCT CAG GGC      732
Met Leu Ile Asn Gly Tyr Ala Leu Asn Cys Val Val Gly Ser Gln Gly
        210                 215                 220

ATG CCC AAG AGA ATA GTT AAT GCA AAA ATT GCT TGT CTT GAC TTC AGC      780
Met Pro Lys Arg Ile Val Asn Ala Lys Ile Ala Cys Leu Asp Phe Ser
225                 230                 235                 240

CTG CAG AAA ACA AAA ATG AAG CTT GGT GTA CAG GTG GTT ATT ACA GAC      828
Leu Gln Lys Thr Lys Met Lys Leu Gly Val Gln Val Val Ile Thr Asp
                245                 250                 255

CCT GAG AAA TTG GAC CAA ATT AGA CAG AGA GAA TCG GAT ATC ACC AAG      876
Pro Glu Lys Leu Asp Gln Ile Arg Gln Arg Glu Ser Asp Ile Thr Lys
            260                 265                 270

GAG AGA ATT CAG AAG ATC CTG GCA ACT GGT GCC AAT GTT ATT CTA ACC      924
Glu Arg Ile Gln Lys Ile Leu Ala Thr Gly Ala Asn Val Ile Leu Thr
        275                 280                 285

ACT GGT GGC ATT GAT GAT ATG TAT CTC AAG TAT TTT GTG GAA GCT GGT      972
Thr Gly Gly Ile Asp Asp Met Tyr Leu Lys Tyr Phe Val Glu Ala Gly
        290                 295                 300

GCC ATG GCT GTT AGG AGA GTT TTA AAA CGA GAC CTG AAG CAT GTT GCA     1020
Ala Met Ala Val Arg Arg Val Leu Lys Arg Asp Leu Lys His Val Ala
305                 310                 315                 320

AAA GCT TCT GGA GCA AGT ATC CTG TCT ACG CTG GCC AAT TTG GAA GGC     1068
Lys Ala Ser Gly Ala Ser Ile Leu Ser Thr Leu Ala Asn Leu Glu Gly
                325                 330                 335
```

```
GAA GAA ACT TTT GAA GTG ACG ATG TTG GGA CAA GCG GAA GAG GTC GTA     1116
Glu Glu Thr Phe Glu Val Thr Met Leu Gly Gln Ala Glu Glu Val Val
        340                 345                 350

CAG GAG AGA ATT TGT GAT GAT GAG CTG ATC TTA ATC AAA AAT ACT AAG     1164
Gln Glu Arg Ile Cys Asp Asp Glu Leu Ile Leu Ile Lys Asn Thr Lys
            355                 360                 365

GCT CGT ACA TCT GCT TCA ATC ATC TTA CGA GGA GCA AAT GAT TTC ATG     1212
Ala Arg Thr Ser Ala Ser Ile Ile Leu Arg Gly Ala Asn Asp Phe Met
370                 375                 380

TGT GAT GAA ATG GAG CGC TCT TTA CAT GAT GCT CTT TGT GTG GTG AAG     1260
Cys Asp Glu Met Glu Arg Ser Leu His Asp Ala Leu Cys Val Val Lys
385                 390                 395                 400

AGA GTT TTG GAG TTG AAA TCT GTG GTC CCA GGT GGA GGT GCT GTA GAA     1308
Arg Val Leu Glu Leu Lys Ser Val Val Pro Gly Gly Gly Ala Val Glu
                405                 410                 415

GCT GCC CTG TCC ATA TAC CTG GAA AAC TAT GCA ACA AAC ATG GGA TCT     1356
Ala Ala Leu Ser Ile Tyr Leu Glu Asn Tyr Ala Thr Asn Met Gly Ser
                420                 425                 430

CGG GAA CAG CTT GCT ATT GCA GAG TTT GCA AGA TCT CTG CTT GTG ATT     1404
Arg Glu Gln Leu Ala Ile Ala Glu Phe Ala Arg Ser Leu Leu Val Ile
            435                 440                 445

CCT AAT ACA CTG GCA GTG AAT GCT GCC CAG GAC TCC ACC GAC CTG GTT     1452
Pro Asn Thr Leu Ala Val Asn Ala Ala Gln Asp Ser Thr Asp Leu Val
450                 455                 460

GCC AAG TTA AGA GCT TTT CAC AAT GAG GCT CAA GTG AAC CCG GAA CGT     1500
Ala Lys Leu Arg Ala Phe His Asn Glu Ala Gln Val Asn Pro Glu Arg
465                 470                 475                 480

AAA AAT CTA AAG TGG ATT GGT CTT GAT TTG GTC CAT GGG AAA CCA CGA     1548
Lys Asn Leu Lys Trp Ile Gly Leu Asp Leu Val His Gly Lys Pro Arg
                485                 490                 495

GAC AAC AAG CAA GCA GGG GTG TTT GAA CCA ACC ATA GTT AAA GTG AAG     1596
Asp Asn Lys Gln Ala Gly Val Phe Glu Pro Thr Ile Val Lys Val Lys
                500                 505                 510

AGC CTG AAG TTC GCA ACA GAG GCT GCA ATC ACC ATC CTT CGG ATT GAC     1644
Ser Leu Lys Phe Ala Thr Glu Ala Ala Ile Thr Ile Leu Arg Ile Asp
            515                 520                 525

GAT CTG ATA AAA TTA CAC CCA GAA AGC AAA GAC GAT AAA CAC GGA AGT     1692
Asp Leu Ile Lys Leu His Pro Glu Ser Lys Asp Asp Lys His Gly Ser
530                 535                 540

TAT GAA AAT GCT GTT CAC TCT GGA GCC CTT GAT GAC TGATTGGATT          1738
Tyr Glu Asn Ala Val His Ser Gly Ala Leu Asp Asp
545                 550                 555

TCCCTCTTAT TTATAACAGT GTCAGGTGCA ATGCCGTAGC CTTGGGTGTC TCACATTAAA   1798

GTACAGCAAG CTGT                                                    1812

(2) INFORMATION FOR SEQ ID NO:55:

(i) SEQUENCE CHARACTERISTICS:
        (A) LENGTH: 1924 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 58..1665

(xi) SEQUENCE DESCRIPTION: SEQ ID NO:55:

GGCTTCCCGG CGCGGATTGT GAGGGGTTCT CTCCTCTACG CGGAATCCGT CGGAACC      57
```

```
ATG GCT TCC CTT TCC CTC GCA CCT GTT AAT ATC TTC AAG GCT GGA GCT         105
Met Ala Ser Leu Ser Leu Ala Pro Val Asn Ile Phe Lys Ala Gly Ala
  1               5                  10                  15

GAT GAA GAG AGG GCC GAG ATA GCT CGC CTG TCG TCG TTT ATC GGT GCC         153
Asp Glu Glu Arg Ala Glu Ile Ala Arg Leu Ser Ser Phe Ile Gly Ala
                 20                  25                  30

ATC GCC ATT GGA GAC TTG GTG AAG AGC ACT TTG GGA CCG AAG GGC ATG         201
Ile Ala Ile Gly Asp Leu Val Lys Ser Thr Leu Gly Pro Lys Gly Met
             35                  40                  45

GAC AAA ATT CTC CTA AGC AGT GGA CGA GAC GCC GCT CTG ATG GTG ACC         249
Asp Lys Ile Leu Leu Ser Ser Gly Arg Asp Ala Ala Leu Met Val Thr
 50                  55                  60

AAC GAC GGT GCT ACC ATT CTC AAG AAC ATT GGT GTG GAC AAC CCC GCA         297
Asn Asp Gly Ala Thr Ile Leu Lys Asn Ile Gly Val Asp Asn Pro Ala
 65                  70                  75                  80

GCA AAG GTT CTA GTT GAT ATG TCA AGG GTT CAA GAT GAT GAA GTT GGT         345
Ala Lys Val Leu Val Asp Met Ser Arg Val Gln Asp Asp Glu Val Gly
                 85                  90                  95

GAT GGC ACT ACC TCT GTT ACT GTC TTA GCC GCA GAG CTG CTC CGG GAA         393
Asp Gly Thr Thr Ser Val Thr Val Leu Ala Ala Glu Leu Leu Arg Glu
            100                 105                 110

GCA GAA TCT TTA ATT GCA AAA AAG ATA CAT CCA CAG ACC ATC ATC TCA         441
Ala Glu Ser Leu Ile Ala Lys Lys Ile His Pro Gln Thr Ile Ile Ser
            115                 120                 125

GGT TGG AGA GAA GCC ACA AAG GCA GCA AGA GAG GCC CTG CTG AGC TCC         489
Gly Trp Arg Glu Ala Thr Lys Ala Ala Arg Glu Ala Leu Leu Ser Ser
130                 135                 140

GCT GTG GAT CAT GGT TCT GAT GAA GCC AGA TTC TGG CAG GAC TTA ATG         537
Ala Val Asp His Gly Ser Asp Glu Ala Arg Phe Trp Gln Asp Leu Met
145                 150                 155                 160

AAC ATT GCA GGA ACG ACA TTG TCC TCA AAG CTC CTT ACT CAC CAC AAG         585
Asn Ile Ala Gly Thr Thr Leu Ser Ser Lys Leu Leu Thr His His Lys
                165                 170                 175

GAC CAC TTT ACT AAA CTG GCC GTG GAA GCG GGT CTC AGA CTG AAA GGC         633
Asp His Phe Thr Lys Leu Ala Val Glu Ala Gly Leu Arg Leu Lys Gly
            180                 185                 190

TCT GGC AAC CTG GAG GCG ATT CAT GTC ATC AAG AAA CTA GGT GGG AGT         681
Ser Gly Asn Leu Glu Ala Ile His Val Ile Lys Lys Leu Gly Gly Ser
            195                 200                 205

CTG GCA GAC TCC TAT CTA GAT GAA GGT TTT CTT TTG GAT AAA AAA ATT         729
Leu Ala Asp Ser Tyr Leu Asp Glu Gly Phe Leu Leu Asp Lys Lys Ile
210                 215                 220

GGA GTA AAT CAA CCA AAG AGA ATT GAA AAT GCT AAA ATT CTT ATT GCA         777
Gly Val Asn Gln Pro Lys Arg Ile Glu Asn Ala Lys Ile Leu Ile Ala
225                 230                 235                 240

AAT ACT GGG ATG GAT ACA GAC AAA ATA AAG ATA TTT GGC TCT CGG GTA         825
Asn Thr Gly Met Asp Thr Asp Lys Ile Lys Ile Phe Gly Ser Arg Val
                245                 250                 255

AGA GTT GAT TCC ACA GCA AAG GTT GCA GAG ATA GAA CAT GCA GAA AAG         873
Arg Val Asp Ser Thr Ala Lys Val Ala Glu Ile Glu His Ala Glu Lys
            260                 265                 270

GAG AAG ATG AAG GAG AAA GTT GAA CGT ATT CTT AAG CAT GGA ATA AAT         921
Glu Lys Met Lys Glu Lys Val Glu Arg Ile Leu Lys His Gly Ile Asn
            275                 280                 285

TGC TTT ATT AAC AGA CAG TTA ATT TAT AAT TAC CCT GAA CAA CTC TTC         969
Cys Phe Ile Asn Arg Gln Leu Ile Tyr Asn Tyr Pro Glu Gln Leu Phe
            290                 295                 300

GGC GCT GCT GGC GTC ATG GCT ATT GAG CAT GCG GAT TTC GCA GGT GTG        1017
Gly Ala Ala Gly Val Met Ala Ile Glu His Ala Asp Phe Ala Gly Val
305                 310                 315                 320
```

```
GAG CGC CTC GCT CTT GTC ACA GGT GGT GAG ATT GCC TCT ACC TTT GAT     1065
Glu Arg Leu Ala Leu Val Thr Gly Gly Glu Ile Ala Ser Thr Phe Asp
            325                 330                 335

CAC CCA GAA CTT GTG AAG CTT GGA AGT TGC AAA CTT ATT GAA GAA GTT     1113
His Pro Glu Leu Val Lys Leu Gly Ser Cys Lys Leu Ile Glu Glu Val
            340                 345                 350

ATG ATC GGG GAA GAT AAA CTC ATT CAC TTT TCT GGG GTT GCC CTT GGT     1161
Met Ile Gly Glu Asp Lys Leu Ile His Phe Ser Gly Val Ala Leu Gly
            355                 360                 365

GAG GCA TGC ACC ATT GTG CTT CGT GGT GCC ACT CAG CAA ATT CTG GAT     1209
Glu Ala Cys Thr Ile Val Leu Arg Gly Ala Thr Gln Gln Ile Leu Asp
        370                 375                 380

GAA GCT GAA CGA TCT CTG CAT GAT GCT CTT TGT GTT CTT GCT CAG ACT     1257
Glu Ala Glu Arg Ser Leu His Asp Ala Leu Cys Val Leu Ala Gln Thr
385                 390                 395                 400

GTA AAA GAT CCT AGA ACA GTT TAC GGG GGA GGC TGC TCT GAG ATG CTG     1305
Val Lys Asp Pro Arg Thr Val Tyr Gly Gly Gly Cys Ser Glu Met Leu
                405                 410                 415

ATG GCC CAT GCT GTG ACA CAG CTT GCC AAC AGA ACC CCA GGA AAA GAA     1353
Met Ala His Ala Val Thr Gln Leu Ala Asn Arg Thr Pro Gly Lys Glu
            420                 425                 430

GCT GTA GCA ATG GAG TCG TTT GCA AAA GCC CTG AGA ATG TTG CCG ACC     1401
Ala Val Ala Met Glu Ser Phe Ala Lys Ala Leu Arg Met Leu Pro Thr
            435                 440                 445

ATC ATA GCC GAC AAT GCG GGC TAT GAC AGT GCA GAT CTG GTG GCA CAG     1449
Ile Ile Ala Asp Asn Ala Gly Tyr Asp Ser Ala Asp Leu Val Ala Gln
        450                 455                 460

CTC CGA GCT GCT CAC AGT GAA GGC CAT ATA ACT GCT GGA CTG GAT ATG     1497
Leu Arg Ala Ala His Ser Glu Gly His Ile Thr Ala Gly Leu Asp Met
465                 470                 475                 480

AAG GAA GGT ACC ATC GGC GAT ATG GCA GTA CTG GGT ATA ACA GAG AGT     1545
Lys Glu Gly Thr Ile Gly Asp Met Ala Val Leu Gly Ile Thr Glu Ser
                485                 490                 495

TTT CAA GTG AAG CGA CAG GTT CTT CTG AGT GCG GCT GAA GCA GCA GAG     1593
Phe Gln Val Lys Arg Gln Val Leu Leu Ser Ala Ala Glu Ala Ala Glu
            500                 505                 510

GTG ATC CTG CGA GTG GAC AAC ATT ATC AAA GCA GCA CCA AGG AAA CGT     1641
Val Ile Leu Arg Val Asp Asn Ile Ile Lys Ala Ala Pro Arg Lys Arg
            515                 520                 525

GTC CCC GAT CAC CAC CCC TGT TAAGCATTCC CATTTGCTGA TGAACTCTGG        1692
Val Pro Asp His His Pro Cys
            530             535

GCCAGTTCAT AGCAAAGTTG TACTTGGAAG ACTTCAACCT TTAAAGAAGA CTGGTGGAAT   1752

TGACCTGTCC ATGATAGCCT TAAGTTTGAA CATTAGCTGA CCTTCTGTGT TAAACATGGG   1812

TCTAATTTAT TTACTGTTTC ATTTTCCATA CAATTCAGTT GATTTACAAG TTCATTTCTC   1872

ATACTGTGTA TTAAAATAAA AATCCAGTTA CTTAGCCCTT AAAAAAAAAA AA           1924

(2) INFORMATION FOR SEQ ID NO:56:

(i) SEQUENCE CHARACTERISTICS:
        (A) LENGTH: 1970 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 102..1739
```

(xi) SEQUENCE DESCRIPTION: SEQ ID NO:56:

```
TGTCATTCCT GAGGAGGCAG CGTTTTCTTC GCTGCTCTTC TCTCCAGAAG GTTCTGCCGA         60

TTCCCCCCAG CTCTGGAGAG TCGGCTCTGC GTCGTGCCGC C ATG ATG GGC CAC            113
                                             Met Met Gly His
                                              1

CGT CCA GTG CTC GTG CTC AGT CAG AAC ACA AAG CGT GAA TCT GGA AGA          161
Arg Pro Val Leu Val Leu Ser Gln Asn Thr Lys Arg Glu Ser Gly Arg
 5               10                  15                  20

AAA GTT CAG TCT GGA AAT ATC AAT GCT GCA AAG ACA ATT GCA GAC ATC          209
Lys Val Gln Ser Gly Asn Ile Asn Ala Ala Lys Thr Ile Ala Asp Ile
             25                  30                  35

ATC CGG ACC TGC TTG GGA CCT AAA TCT ATG ATG AAG ATG CTT TTG GAC          257
Ile Arg Thr Cys Leu Gly Pro Lys Ser Met Met Lys Met Leu Leu Asp
         40                  45                  50

CCA ATG GGA GGC ATC GTG ATG ACC AAT GAT GGC AAT GCC ATT CTT CGA          305
Pro Met Gly Gly Ile Val Met Thr Asn Asp Gly Asn Ala Ile Leu Arg
     55                  60                  65

GAG ATT CAA GTC CAG CAT CCC GCA GCA AAG TCC ATG ATT GAA ATT AGC          353
Glu Ile Gln Val Gln His Pro Ala Ala Lys Ser Met Ile Glu Ile Ser
 70                  75                  80

AGG ACC CAG GAT GAA GAG GTT GGA GAT GGG ACC ACA TCA GTA ATT ATT          401
Arg Thr Gln Asp Glu Glu Val Gly Asp Gly Thr Thr Ser Val Ile Ile
 85                  90                  95                 100

CTT GCG GGA GAA ATG CTC TCT GTG GCT GAA CAC TTC CTA GAG CAG CAG          449
Leu Ala Gly Glu Met Leu Ser Val Ala Glu His Phe Leu Glu Gln Gln
                105                 110                 115

ATG CAC CCA ACA GTG GTG ATC AGT GCT TAC CGC ATG GCA CTG GAT GAT          497
Met His Pro Thr Val Val Ile Ser Ala Tyr Arg Met Ala Leu Asp Asp
            120                 125                 130

ATG ATC AGC ACT CTG AAG AAA ATC AGT ACT CCT GTT GAT GTC AAT AAC          545
Met Ile Ser Thr Leu Lys Lys Ile Ser Thr Pro Val Asp Val Asn Asn
        135                 140                 145

CGT GAG ATG ATG TTG AGC ATC ATC AAT AGC TCT ATT ACT ACA AAA GTC          593
Arg Glu Met Met Leu Ser Ile Ile Asn Ser Ser Ile Thr Thr Lys Val
    150                 155                 160

ATC AGT CGG TGG TCC TCC TTG GCA TGC AAC ATT GCA CTG GAT GCT GTT          641
Ile Ser Arg Trp Ser Ser Leu Ala Cys Asn Ile Ala Leu Asp Ala Val
165                 170                 175                 180

AAG ACT GTG CAG TTT GAA GAG AAT GGC AGA AAG GAA ATT GAC ATC AAA          689
Lys Thr Val Gln Phe Glu Glu Asn Gly Arg Lys Glu Ile Asp Ile Lys
                185                 190                 195

AAA TAT GCA AGG GTA GAA AAG ATA CCC GGG GGC ATC ATT GAA GAC TCA          737
Lys Tyr Ala Arg Val Glu Lys Ile Pro Gly Gly Ile Ile Glu Asp Ser
            200                 205                 210

TGT GTC TTA CGT GGA GTT ATG ATT AAC AAG GAT GTG ACC CAT CCA AGG          785
Cys Val Leu Arg Gly Val Met Ile Asn Lys Asp Val Thr His Pro Arg
        215                 220                 225

ATG CGC CGC TAT ATT AAG AAT CCT CGA ATT GTG CTA TTG GAT TCT TCT          833
Met Arg Arg Tyr Ile Lys Asn Pro Arg Ile Val Leu Leu Asp Ser Ser
    230                 235                 240

TTG GAG TAC AAG AAA GGA GAA AGC CAG ACC GAC ATC GAG ATT ACC CGG          881
Leu Glu Tyr Lys Lys Gly Glu Ser Gln Thr Asp Ile Glu Ile Thr Arg
245                 250                 255                 260

GAG GAG GAC TTC ACG CGG ATC CTG CAG ATG GAG GAG GAG TAC ATC CAT          929
Glu Glu Asp Phe Thr Arg Ile Leu Gln Met Glu Glu Glu Tyr Ile His
                265                 270                 275

CAG CTG TGT GAG GAC ATC ATC CAG CTG AAG CCT GAC GTG GTC ATC ACA          977
Gln Leu Cys Glu Asp Ile Ile Gln Leu Lys Pro Asp Val Val Ile Thr
```

```
                       280                 285                 290
GAG AAG GGC ATC TCA GAT TTA GCT CAG CAC TAC CTC ATG CGG GCC AAT          1025
Glu Lys Gly Ile Ser Asp Leu Ala Gln His Tyr Leu Met Arg Ala Asn
            295                 300                 305

GTC ACA GCC ATT CGT AGA GTC CGG AAA ACA GAC AAT AAT CGC ATT GCT          1073
Val Thr Ala Ile Arg Arg Val Arg Lys Thr Asp Asn Asn Arg Ile Ala
    310                 315                 320

AGA GCC TGT GGG GCA CGG ATA GTC AGC CGA CCT GAG GAA CTG AGA GAA          1121
Arg Ala Cys Gly Ala Arg Ile Val Ser Arg Pro Glu Glu Leu Arg Glu
325                 330                 335                 340

GAT GAT GTT GGT ACA GGG GCA GGC TTA TTG GAA ATC AAG AAG ATT GGA          1169
Asp Asp Val Gly Thr Gly Ala Gly Leu Leu Glu Ile Lys Lys Ile Gly
                345                 350                 355

GAT GAG TAC TTT ACA TTC ATC ACT GAC TGC AAA GAC CCA AAG GCC TGC          1217
Asp Glu Tyr Phe Thr Phe Ile Thr Asp Cys Lys Asp Pro Lys Ala Cys
            360                 365                 370

ACC ATT CTT CTT AGA GGA GCC AGC AAA GAG ATA CTC TCG GAA GTA GAA          1265
Thr Ile Leu Leu Arg Gly Ala Ser Lys Glu Ile Leu Ser Glu Val Glu
        375                 380                 385

CGC AAC CTC CAG GAT GCC ATG CAA GTG TGC CGC AAT GTT CTA CTG GAC          1313
Arg Asn Leu Gln Asp Ala Met Gln Val Cys Arg Asn Val Leu Leu Asp
    390                 395                 400

CCT CAG CTG GTG CCT GGT GGT GGA GCC TCT GAG ATG GCT GTG GCT CAT          1361
Pro Gln Leu Val Pro Gly Gly Gly Ala Ser Glu Met Ala Val Ala His
405                 410                 415                 420

GCC TTG ACA GAA AAA TCT AAG GCC ATG ACT GGT GTG GAA CAA TGG CCA          1409
Ala Leu Thr Glu Lys Ser Lys Ala Met Thr Gly Val Glu Gln Trp Pro
                425                 430                 435

TAT AGA GCT GTG GCC CAG GCG TTA GAG GTC ATC CCT CGG ACC TTG ATC          1457
Tyr Arg Ala Val Ala Gln Ala Leu Glu Val Ile Pro Arg Thr Leu Ile
            440                 445                 450

CAG AAT TGT GGG GCC AGT ACC ATT CGT CTG CTT ACC TCC CTT CGG GCC          1505
Gln Asn Cys Gly Ala Ser Thr Ile Arg Leu Leu Thr Ser Leu Arg Ala
        455                 460                 465

AAG CAC ACA CAG GAG AGT TGT GAG ACC TGG GGT GTG AAT GGT GAG ACT          1553
Lys His Thr Gln Glu Ser Cys Glu Thr Trp Gly Val Asn Gly Glu Thr
    470                 475                 480

GGT ACC TTG GTG GAC ATG AAA GAG CTG GGT ATT TGG GAG CCA TTG GCT          1601
Gly Thr Leu Val Asp Met Lys Glu Leu Gly Ile Trp Glu Pro Leu Ala
485                 490                 495                 500

GTG AAG CTA CAA ACG TAC AAA ACA GCA GTA GAG ACT GCA GTT CTG CTT          1649
Val Lys Leu Gln Thr Tyr Lys Thr Ala Val Glu Thr Ala Val Leu Leu
                505                 510                 515

CTG CGG ATT GAT GAC ATT GTC TCT GGC CAC AAG AAG AAG GGT GAT GAC          1697
Leu Arg Ile Asp Asp Ile Val Ser Gly His Lys Lys Lys Gly Asp Asp
            520                 525                 530

CAG AAC CGG CAA ACT GGT GCT CCA GAT GCT GGC CAG GAG TGAGTGCTGA           1746
Gln Asn Arg Gln Thr Gly Ala Pro Asp Ala Gly Gln Glu
        535                 540                 545

GCACGGTGAC TTCCATGCAC AGAACCAGCA GTCTCCCCTT TCCTGAGCCA GAGTTCCAGG        1806

AACACTGTGG ACATCTTTGT TGCGAAGGA TCAGGTTGAG GGGCAGCCCC CAGTCTGTCC         1866

CATCTCAGTT TGCAAAAAGC ACTGACACGT ATCTCTTCTA TTGTAAGCTT TCCATTTAGT        1926

TTGCTTCCAA TGATTAAATC TAAGTCATTT GAAAAAAAAA AAAA                        1970

(2) INFORMATION FOR SEQ ID NO:57:

(i) SEQUENCE CHARACTERISTICS:
        (A) LENGTH: 1986 base pairs
```

```
            (B) TYPE: nucleic acid
            (C) STRANDEDNESS: single
            (D) TOPOLOGY: linear (ii) MOLECULE TYPE: cDNA (ix) FEATURE:
            (A) NAME/KEY: CDS
            (B) LOCATION: 162..1781

(xi) SEQUENCE DESCRIPTION: SEQ ID NO:57:

GGCTCTCCAG CAGGCCCCTT GCTCGGCTTC CGCCTTCTCT CCCGGCGTCG CTTTCTGGAA         60

GGTTCGTGGA GGAGGCGGTC AGGGAGACCG TTACTCCACA GCAAGCCGGA ATCCGTGTCC        120

ATCCGTCCTC CTGAACCCGC GCAGACGCCA CCAAGGTCGC C ATG CCG GAG AAC           173
                                             Met Pro Glu Asn
                                               1

GTA GCT TCC CGA AGC GGG GCG CCC ACC GCC GGG CCC GGC AGC CGC GGG         221
Val Ala Ser Arg Ser Gly Ala Pro Thr Ala Gly Pro Gly Ser Arg Gly
  5              10                  15                  20

AAA AGC GCC TAC CAG GAC CGC GAC AAG CCA GCC CAG ATC CGC TTC AGC         269
Lys Ser Ala Tyr Gln Asp Arg Asp Lys Pro Ala Gln Ile Arg Phe Ser
                 25                  30                  35

AAT ATT TCC GCG GCC AAA GCG GTT GCT GAT GCT ATT AGA ACA AGC CTT         317
Asn Ile Ser Ala Ala Lys Ala Val Ala Asp Ala Ile Arg Thr Ser Leu
             40                  45                  50

GGA CCT AAA GGA ATG GAC AAA ATG ATT CAA GAT GGA AAA GGC GAT GTG         365
Gly Pro Lys Gly Met Asp Lys Met Ile Gln Asp Gly Lys Gly Asp Val
         55                  60                  65

ACC ATT ACA AAT GAT GGT GCC ACC ATT CTG AAA CAA ATG CAG GTA TTG         413
Thr Ile Thr Asn Asp Gly Ala Thr Ile Leu Lys Gln Met Gln Val Leu
     70                  75                  80

CAT CCA GCA GCC AGA ATG CTG GTG GAA TTG TCT AAA GCT CAA GAC ATA         461
His Pro Ala Ala Arg Met Leu Val Glu Leu Ser Lys Ala Gln Asp Ile
 85                  90                  95                 100

GAA GCA GGA GAT GGC ACC ACG TCG GTT GTC ATC ATT GCT GGC TCT CTT         509
Glu Ala Gly Asp Gly Thr Thr Ser Val Val Ile Ile Ala Gly Ser Leu
                105                 110                 115

TTA GAC TCC TGT ACC AAA CTT CTG CAG AAA GGT ATA CAT CCA ACC ATC         557
Leu Asp Ser Cys Thr Lys Leu Leu Gln Lys Gly Ile His Pro Thr Ile
            120                 125                 130

ATT TCC GAG TCA TTC CAG AAA GCT TTG GAA AAG GGT CTT GAA ATC CTT         605
Ile Ser Glu Ser Phe Gln Lys Ala Leu Glu Lys Gly Leu Glu Ile Leu
        135                 140                 145

ACT GAC ATG TCT CGA CCT GTG CAA CTG AGC GAC AGA GAA ACT TTG TTA         653
Thr Asp Met Ser Arg Pro Val Gln Leu Ser Asp Arg Glu Thr Leu Leu
    150                 155                 160

AAT AGC GCA ACT ACT TCA TTG AAT TCA AAG GTT GTC TCT CAG TAT TCA         701
Asn Ser Ala Thr Thr Ser Leu Asn Ser Lys Val Val Ser Gln Tyr Ser
165                 170                 175                 180

AGT CTA CTC TCT CCA ATG AGT GTC AAT GCG GTG ATG AAA GTG ATT GAC         749
Ser Leu Leu Ser Pro Met Ser Val Asn Ala Val Met Lys Val Ile Asp
                185                 190                 195

CCA GCC ACA GCT ACC AGT GTA GAT CTT CGA GAT ATT AAA ATA GTT AAG         797
Pro Ala Thr Ala Thr Ser Val Asp Leu Arg Asp Ile Lys Ile Val Lys
            200                 205                 210

AAG CTT GGT GGG ACA ATA GAT GAC TGT GAG CTG GTG GAA GGC CTC GTT         845
Lys Leu Gly Gly Thr Ile Asp Asp Cys Glu Leu Val Glu Gly Leu Val
        215                 220                 225

CTC ACA CAG AAA GTA GCA AAT TCT GGC ATA ACA AGA GTT GAA AAG GCT         893
Leu Thr Gln Lys Val Ala Asn Ser Gly Ile Thr Arg Val Glu Lys Ala
    230                 235                 240
```

```
AAG ATT GGG CTT ATT CAG TTT TGC TTA TCT GCT CCT AAA ACA GAT ATG        941
Lys Ile Gly Leu Ile Gln Phe Cys Leu Ser Ala Pro Lys Thr Asp Met
245                 250                 255                 260

GAT AAT CAA ATA GTA GTA TCT GAC TAT GCC CAG ATG GAT CGA GTG CTT        989
Asp Asn Gln Ile Val Val Ser Asp Tyr Ala Gln Met Asp Arg Val Leu
                265                 270                 275

CGA GAG GAG AGA GCC TAT ATT TTA AAT TTG GTG AAG CAA ATT AAG AAA       1037
Arg Glu Glu Arg Ala Tyr Ile Leu Asn Leu Val Lys Gln Ile Lys Lys
            280                 285                 290

ACA GGA TGT AAT GTC CTT CTC ATA CAG AAG TCT ATC CTG AGA GAT GCC       1085
Thr Gly Cys Asn Val Leu Leu Ile Gln Lys Ser Ile Leu Arg Asp Ala
        295                 300                 305

CTT AGT GAT CTT GCA TTA CAT TTT CTG AAT AAG ATG AAG ATT ATG GTG       1133
Leu Ser Asp Leu Ala Leu His Phe Leu Asn Lys Met Lys Ile Met Val
    310                 315                 320

GTT AAG GAC GTT GAA AGA GAA GAC ATT GAA TTC ATC TGT AAG ACA ATT       1181
Val Lys Asp Val Glu Arg Glu Asp Ile Glu Phe Ile Cys Lys Thr Ile
325                 330                 335                 340

GGA ACC AAA CCA GTT GCT CAC ATT GAC CAG TTC ACT GCT GAC ATG CTG       1229
Gly Thr Lys Pro Val Ala His Ile Asp Gln Phe Thr Ala Asp Met Leu
                345                 350                 355

GGT TCT GCT GAG TTA GCA GAG GAA GTC AGT TTA AAT GGT TCT GGA AAA       1277
Gly Ser Ala Glu Leu Ala Glu Glu Val Ser Leu Asn Gly Ser Gly Lys
            360                 365                 370

CTA TTC AAG ATT ACA GGT TGT ACA AGC CCA GGG AAA ACA GTT ACA ATT       1325
Leu Phe Lys Ile Thr Gly Cys Thr Ser Pro Gly Lys Thr Val Thr Ile
        375                 380                 385

GTC GTA CGT GGT TCT AAC AAA CTG GTG ATT GAA GAA GCT GAG CGC TCC       1373
Val Val Arg Gly Ser Asn Lys Leu Val Ile Glu Glu Ala Glu Arg Ser
    390                 395                 400

ATT CAT GAT GCT CTC TGT GTC ATC CGA TGC TTA GTA AAG AAA AGA GCT       1421
Ile His Asp Ala Leu Cys Val Ile Arg Cys Leu Val Lys Lys Arg Ala
405                 410                 415                 420

CTT ATT GCA GGA GGT GGT GCT CCA GAA ATA GAG CTG GCC CTC AGA CTG       1469
Leu Ile Ala Gly Gly Gly Ala Pro Glu Ile Glu Leu Ala Leu Arg Leu
                425                 430                 435

ACA GAG TAC TCC CGA ACA CTG AGT GGT ATG GAG TCC TAC TGT GTT CGT       1517
Thr Glu Tyr Ser Arg Thr Leu Ser Gly Met Glu Ser Tyr Cys Val Arg
            440                 445                 450

GCT TTC GCG GAT GCT ATG GAA GTC ATT CCA TCT ACA CTA GCT GAA AAT       1565
Ala Phe Ala Asp Ala Met Glu Val Ile Pro Ser Thr Leu Ala Glu Asn
        455                 460                 465

GCT GGC CTG AAT CCC ATT TCT ACA GTA ACA GAG CTA AGA AAC CGC CAT       1613
Ala Gly Leu Asn Pro Ile Ser Thr Val Thr Glu Leu Arg Asn Arg His
    470                 475                 480

GCC CAA GGA GAA AAA ACT ACA GGC ATT AAT GTC CGA AAG GGT GGG ATC       1661
Ala Gln Gly Glu Lys Thr Thr Gly Ile Asn Val Arg Lys Gly Gly Ile
485                 490                 495                 500

TCC AAC ATT TTG GAG GAA ATG GTT GTT CAG CCT CTG TTG GTG TCA GTC       1709
Ser Asn Ile Leu Glu Glu Met Val Val Gln Pro Leu Leu Val Ser Val
                505                 510                 515

AGT GCT TTG ACC TTA GCA ACT GAA ACT GTG CGG AGC ATT CTG AAA ATC       1757
Ser Ala Leu Thr Leu Ala Thr Glu Thr Val Arg Ser Ile Leu Lys Ile
            520                 525                 530

GAT GAT GTG GTA AAT ACT CGA TAATCTGGAT AAAAGGATGG TTGACTGCAT          1808
Asp Asp Val Val Asn Thr Arg
        535                 540

CATTATGGAC AGAAGTACTG TGGCTGGAAT GAAGGACAAC CACCTTGTTC CTTGTCTGGA     1868
```

```
AGCTTCAGAG TTTTTGGACA TTGTCTTCCA GTTGGCATTT GTTTGAAATT GTATTGAAAC      1928

AATTTAATGA AAACATTAAA TACTTGGTTT TAAACTCCAA AAAAAAAAAA AAAAAAA         1986

(2) INFORMATION FOR SEQ ID NO:58:

(i) SEQUENCE CHARACTERISTICS:
        (A) LENGTH: 1799 base pairs
        (B) TYPE: nucleic acid
        (C) STRANDEDNESS: single
        (D) TOPOLOGY: linear (ii) MOLECULE TYPE: cDNA (ix) FEATURE:
         (A) NAME/KEY: CDS
         (B) LOCATION: 100..1725

(xi) SEQUENCE DESCRIPTION: SEQ ID NO:58:

GGATTCTGCG TCCTCTCGCG AGAGGGAGGT GCGGTGTGTC TCTCTTCCCG AGTGGTCCCC       60

GCTGGTTACT GGAGGAGCGC TCGTTCTAGT TCGTCCACC ATG GCG TCC GTG GGG        114
                                           Met Ala Ser Val Gly
                                             1               5

ACC CTC GCC TTC GAT GAG TAT GGG CGC CCC TTT CTC ATT ATC AAG GAC       162
Thr Leu Ala Phe Asp Glu Tyr Gly Arg Pro Phe Leu Ile Ile Lys Asp
            10                  15                  20

CAA GAT CGC AAG TCC CGT CTC ATG GGG CTT GAG GCC CTC AAG TCT CAC       210
Gln Asp Arg Lys Ser Arg Leu Met Gly Leu Glu Ala Leu Lys Ser His
        25                  30                  35

ATC ATG GCT GCC AAA GCT GTA GCA AAC ACA ATG CGG ACG TCA CTG GGA       258
Ile Met Ala Ala Lys Ala Val Ala Asn Thr Met Arg Thr Ser Leu Gly
    40                  45                  50

CCA AAC GGG CTG GAC AAG ATG ATG GTT GAT AAG GAT GGC GAT GTG ACT       306
Pro Asn Gly Leu Asp Lys Met Met Val Asp Lys Asp Gly Asp Val Thr
55                  60                  65

ATA ACA AAC GAT GGT GCC ACC ATT CTA AGC ATG ATG GAT GTT GAT CAT       354
Ile Thr Asn Asp Gly Ala Thr Ile Leu Ser Met Met Asp Val Asp His
    70                  75                  80                  85

CAG ATT GCC AAG CTG ATG GTT GAA CTG TCC AAA TCC CAG GAT GAT GAA       402
Gln Ile Ala Lys Leu Met Val Glu Leu Ser Lys Ser Gln Asp Asp Glu
        90                  95                 100

ATT GGA GAT GGG ACC ACA GGA GTG GTT GTC TTG GCT GGG GCC TTG TTG       450
Ile Gly Asp Gly Thr Thr Gly Val Val Val Leu Ala Gly Ala Leu Leu
            105                 110                 115

GAA GAA GCT GAA CAG CTG CTG GAC CGA GGC ATT CAC CCA ATC AGA ATT       498
Glu Glu Ala Glu Gln Leu Leu Asp Arg Gly Ile His Pro Ile Arg Ile
                120                 125                 130

GCT GAT GGC TAC GAG CAG GCT GCC CGA ATT GCA ATA CAA CAC CTG GAC       546
Ala Asp Gly Tyr Glu Gln Ala Ala Arg Ile Ala Ile Gln His Leu Asp
135                 140                 145

AAG ATC AGC GAT AAA GTG CTT GTC GAC ATA AAC AAC CCT GAA CCT CTG       594
Lys Ile Ser Asp Lys Val Leu Val Asp Ile Asn Asn Pro Glu Pro Leu
150                 155                 160                 165

ATT CAG ACT GCA AAA ACC ACG CTG GGC TCC AAA GTG ATT AAC AGC TGT       642
Ile Gln Thr Ala Lys Thr Thr Leu Gly Ser Lys Val Ile Asn Ser Cys
            170                 175                 180

CAC CGA CAG ATG GCT GAG ATC GCC GTG AAT GCC GTC CTC ACG GTG GCA       690
His Arg Gln Met Ala Glu Ile Ala Val Asn Ala Val Leu Thr Val Ala
                185                 190                 195

GAT ATG GAG CGG AGA GAT GTT GAC TTT GAG CTC ATT AAA GTG GAA GGC       738
Asp Met Glu Arg Arg Asp Val Asp Phe Glu Leu Ile Lys Val Glu Gly
            200                 205                 210
```

```
AAA GTA GGT GGG CGT CTG GAA GAC ACC AAG CTC ATA AAG GGT GTG ATC      786
Lys Val Gly Gly Arg Leu Glu Asp Thr Lys Leu Ile Lys Gly Val Ile
    215                 220                 225

GTC GAC AAG GAC TTC AGC CAC CCA CAG ATG CCG AAA AAA GTG GTA GAT      834
Val Asp Lys Asp Phe Ser His Pro Gln Met Pro Lys Lys Val Val Asp
230                 235                 240                 245

GCT AAG ATT GCG ATT CTC ACG TGT CCA TTT GAG CCA CCT AAA CCT AAG      882
Ala Lys Ile Ala Ile Leu Thr Cys Pro Phe Glu Pro Pro Lys Pro Lys
                250                 255                 260

ACA AAG CAC AAG CTG GAT GTC ATG TCT GTG GAG GAC TAC AAA GCC CTG      930
Thr Lys His Lys Leu Asp Val Met Ser Val Glu Asp Tyr Lys Ala Leu
            265                 270                 275

CAG AAG TAC GAA AAG GAG AAG TTT GAA GAG ATG ATT AAG CAG ATT AAA      978
Gln Lys Tyr Glu Lys Glu Lys Phe Glu Glu Met Ile Lys Gln Ile Lys
        280                 285                 290

GAA ACT GGT GCT AAC CTA GCT ATT TGC CAG TGG GGC TTT GAC GAT GAA     1026
Glu Thr Gly Ala Asn Leu Ala Ile Cys Gln Trp Gly Phe Asp Asp Glu
    295                 300                 305

GCC AAT CAC TTA CTT CTT CAG AAC GGC CTG CCT GCA GTC CGC TGG GTA     1074
Ala Asn His Leu Leu Leu Gln Asn Gly Leu Pro Ala Val Arg Trp Val
310                 315                 320                 325

GGG GGA CCT GAG ATT GAG CTG ATC GCC ATT GCA ACA GGA GGA CGG ATT     1122
Gly Gly Pro Glu Ile Glu Leu Ile Ala Ile Ala Thr Gly Gly Arg Ile
                330                 335                 340

GTC CCA CGG TTC TCA GAG CTC ACC TCT GAG AAG CTG GGC TTT GCT GGT     1170
Val Pro Arg Phe Ser Glu Leu Thr Ser Glu Lys Leu Gly Phe Ala Gly
            345                 350                 355

GTG GTG CAG GAG ATC TCC TTT GGC ACT ACA AAA GAC AAA ATG CTG GTT     1218
Val Val Gln Glu Ile Ser Phe Gly Thr Thr Lys Asp Lys Met Leu Val
        360                 365                 370

ATC GAG AAG TGT AAG AAC TCT AGA GCT GTG ACC ATT TTC ATC AGA GGA     1266
Ile Glu Lys Cys Lys Asn Ser Arg Ala Val Thr Ile Phe Ile Arg Gly
    375                 380                 385

GGA AAC AAG ATG ATC ATA GAA GAA GCA AAA CGA TCT CTC CAT GAT GCC     1314
Gly Asn Lys Met Ile Ile Glu Glu Ala Lys Arg Ser Leu His Asp Ala
390                 395                 400                 405

CTG TGT GTC ATC CGG AAC CTC ATC CGT GAC AAC CGT GTT GTG TAT GGA     1362
Leu Cys Val Ile Arg Asn Leu Ile Arg Asp Asn Arg Val Val Tyr Gly
                410                 415                 420

GGA GGG GCA GCC GAA ATA TCC TGC GCC CTG GCA GTC AGC CAA GAG GCA     1410
Gly Gly Ala Ala Glu Ile Ser Cys Ala Leu Ala Val Ser Gln Glu Ala
            425                 430                 435

GAC AAG TGC CCA ACT TTG GAA CAG TAT GCC ATG AGA GCT TTT GCA GAT     1458
Asp Lys Cys Pro Thr Leu Glu Gln Tyr Ala Met Arg Ala Phe Ala Asp
        440                 445                 450

GCC TTG GAG GTC ATC CCC ATG GCC CTT TCA GAA AAT AGT GGC ATG AAT     1506
Ala Leu Glu Val Ile Pro Met Ala Leu Ser Glu Asn Ser Gly Met Asn
    455                 460                 465

CCC ATT CAG ACC ATG ACT GAA GTT CGA GCC AGA CAG GTG AAG GAG TCT     1554
Pro Ile Gln Thr Met Thr Glu Val Arg Ala Arg Gln Val Lys Glu Ser
470                 475                 480                 485

AAC CCT GCC CTG GGG ATT GAC TGT TTG CAC AAG GGC AGT AAC GAT ATG     1602
Asn Pro Ala Leu Gly Ile Asp Cys Leu His Lys Gly Ser Asn Asp Met
                490                 495                 500

CAG TAT CAG CAT GTC ATA GAA ACC TTG ATT GGC AAA AAG CAG CAG ATC     1650
Gln Tyr Gln His Val Ile Glu Thr Leu Ile Gly Lys Lys Gln Gln Ile
            505                 510                 515

TCT CTT GCC ACC CAG ATG GTT AGG ATG ATT CTG AAG ATT GAT GAC ATC     1698
Ser Leu Ala Thr Gln Met Val Arg Met Ile Leu Lys Ile Asp Asp Ile
        520                 525                 530
```

```
CGT AAG CCT GGA GAA TCT GAA GAA TAAACTGTAC CATTTACCAC TGTGACTAAA      1752
Arg Lys Pro Gly Glu Ser Glu Glu
    535                 540

TAAAGGGTGT GTCTGTTAAA AAAAAAAAAA AAAAAAAAAA AAAAAAA                   1799

(2) INFORMATION FOR SEQ ID NO:59:

(i) SEQUENCE CHARACTERISTICS:
        (A) LENGTH: 2205 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 55..1650

(xi) SEQUENCE DESCRIPTION: SEQ ID NO:59:

GAAGACCCCG CAGAGAGCAC GTTGTTCTCG GCCTCTCCCG GAGCTAGGCC AGCC ATG        57
                                                            Met
                                                            1

GCG GCG GTA AAG ACC CTA AAT CCG AAG GCC GAG GTG GCC CGG GCC CAG       105
Ala Ala Val Lys Thr Leu Asn Pro Lys Ala Glu Val Ala Arg Ala Gln
        5                  10                  15

GCA GCG CTG GCG GTG AAC ATC AGC GCG GCT CGG GGC CTG CAG GAT GTT       153
Ala Ala Leu Ala Val Asn Ile Ser Ala Ala Arg Gly Leu Gln Asp Val
    20                  25                  30

CTG AGG ACC AAC TTG GGG CCT AAG GGC ACC ATG AAG ATG CTT GTA TCT       201
Leu Arg Thr Asn Leu Gly Pro Lys Gly Thr Met Lys Met Leu Val Ser
35                  40                  45

GGT GCT GGA GAC ATC AAA CTT ACT AAA GAT GGC AAT GTG CTG CTT CAT       249
Gly Ala Gly Asp Ile Lys Leu Thr Lys Asp Gly Asn Val Leu Leu His
50                  55                  60                  65

GAA ATG CAA ATT CAA CAC CCA ACA GCC TCT TTG ATA GCA AAA GTG GCT       297
Glu Met Gln Ile Gln His Pro Thr Ala Ser Leu Ile Ala Lys Val Ala
                70                  75                  80

ACA GCC CAG GAT GAC ATA ACT GGC GAT GGC ACT ACA TCC AAT GTC CTC       345
Thr Ala Gln Asp Asp Ile Thr Gly Asp Gly Thr Thr Ser Asn Val Leu
            85                  90                  95

ATC ATC GGG GAG CTG CTC AAA CAG GCG GAC CTG TAC ATT TCT GAA GGT       393
Ile Ile Gly Glu Leu Leu Lys Gln Ala Asp Leu Tyr Ile Ser Glu Gly
        100                 105                 110

CTT CAC CCA AGA ATA ATA ACT GAA GGT TTT GAA GCG GCA AAA GAA AAG       441
Leu His Pro Arg Ile Ile Thr Glu Gly Phe Glu Ala Ala Lys Glu Lys
    115                 120                 125

GCA CTC CAA TTT CTG GAA CAA GTC AAA GTA AGC AAA GAG ATG GAC AGA       489
Ala Leu Gln Phe Leu Glu Gln Val Lys Val Ser Lys Glu Met Asp Arg
130                 135                 140                 145

GAA ACA CTC ATC GAT GTG GCC AGG ACA TCT CTG CGG ACT AAA GTT CAT       537
Glu Thr Leu Ile Asp Val Ala Arg Thr Ser Leu Arg Thr Lys Val His
                150                 155                 160

GCT GAA CTT GCA GAT GTC TTG ACA GAG GCT GTA GTG GAC TCC ATC TTG       585
Ala Glu Leu Ala Asp Val Leu Thr Glu Ala Val Val Asp Ser Ile Leu
            165                 170                 175

GCC ATT AGG AAA AAG GAC GAG CCC ATT GAC CTC TTC ATG GTT GAG ATC       633
Ala Ile Arg Lys Lys Asp Glu Pro Ile Asp Leu Phe Met Val Glu Ile
        180                 185                 190

ATG GAG ATG AAG CAT AAA TCT GAG ACA GAT ACA AGC TTA ATC AGA GGG       681
Met Glu Met Lys His Lys Ser Glu Thr Asp Thr Ser Leu Ile Arg Gly
    195                 200                 205
```

```
CTT GTT TTG GAT CAT GGA GCT CGG CAT CCT GAT ATG AAG AAG AGA GTG    729
Leu Val Leu Asp His Gly Ala Arg His Pro Asp Met Lys Lys Arg Val
210             215                 220                 225

GAA AAT GCC TAC ATC CTC ACG TGC AAC GTG TCC TTA GAG TAT GAG AAA    777
Glu Asn Ala Tyr Ile Leu Thr Cys Asn Val Ser Leu Glu Tyr Glu Lys
                230                 235                 240

ACA GAA GTG AAT TCT GGG TTT TTT TAC AAG AGT GCA GAA GAG AGA GAA    825
Thr Glu Val Asn Ser Gly Phe Phe Tyr Lys Ser Ala Glu Glu Arg Glu
            245                 250                 255

AAA CTA GTA AAG GCT GAA AGA AAA TTC ATT GAA GAT AGA GTT AAA AAA    873
Lys Leu Val Lys Ala Glu Arg Lys Phe Ile Glu Asp Arg Val Lys Lys
        260                 265                 270

ATC ATA GAG CTG AAA AAG AAA GTC TGT GGT GAC TCA GAT AAA GGA TTT    921
Ile Ile Glu Leu Lys Lys Lys Val Cys Gly Asp Ser Asp Lys Gly Phe
275                 280                 285

GTC GTT ATT AAT CAA AAG GGG ATT GAC CCC TTT TCC TTA GAT GCC CTT    969
Val Val Ile Asn Gln Lys Gly Ile Asp Pro Phe Ser Leu Asp Ala Leu
290                 295                 300                 305

GCG AAA GAA GGG ATC GTA GCT CTG CGC AGA GCC AAG AGG AGA AAC ATG   1017
Ala Lys Glu Gly Ile Val Ala Leu Arg Arg Ala Lys Arg Arg Asn Met
                310                 315                 320

GAG AGG CTG ACA CTT GCT TGT GGT GGG ATA GCT CTG AAT TCC TTT GAT   1065
Glu Arg Leu Thr Leu Ala Cys Gly Gly Ile Ala Leu Asn Ser Phe Asp
            325                 330                 335

GAC CTG AAT CCT GAC TGT TTG GGA CAT GCA GGG CTT GTC TAT GAG TAT   1113
Asp Leu Asn Pro Asp Cys Leu Gly His Ala Gly Leu Val Tyr Glu Tyr
        340                 345                 350

ACA CTG GGT GAG GAG AAG TTC ACC TTT ATT GAG AAG TGT AAC AAT CCC   1161
Thr Leu Gly Glu Glu Lys Phe Thr Phe Ile Glu Lys Cys Asn Asn Pro
355                 360                 365

CGT TCT GTC ACT TTA CTG GTT AAA GGA CCA AAT AAG CAC ACA CTG ACT   1209
Arg Ser Val Thr Leu Leu Val Lys Gly Pro Asn Lys His Thr Leu Thr
370                 375                 380                 385

CAA ATC AAG GAT GCA ATA AGA GAT GGC TTG AGG GCT GTC AAA AAT GCT   1257
Gln Ile Lys Asp Ala Ile Arg Asp Gly Leu Arg Ala Val Lys Asn Ala
                390                 395                 400

ATT GAT GAT GGC TGT GTT GTC CCA GGT GCG GGT GCA GTA GAA GTG GCA   1305
Ile Asp Asp Gly Cys Val Val Pro Gly Ala Gly Ala Val Glu Val Ala
            405                 410                 415

CTG GCA GAA GCT CTG ATT AAA TAC AAG CCC AGT GTG AAG GGC AGG GCG   1353
Leu Ala Glu Ala Leu Ile Lys Tyr Lys Pro Ser Val Lys Gly Arg Ala
        420                 425                 430

CAG CTT GGA GTC CAG GCA TTT GCA GAT GCC TTG CTC ATC ATT CCC AAG   1401
Gln Leu Gly Val Gln Ala Phe Ala Asp Ala Leu Leu Ile Ile Pro Lys
435                 440                 445

GTT CTT GCG CAA AAC TCT GGT TTT GAC CTT CAG GAA ACA TTA GTT AAA   1449
Val Leu Ala Gln Asn Ser Gly Phe Asp Leu Gln Glu Thr Leu Val Lys
450                 455                 460                 465

GTT CAA GCT GAA CAT TCA GAA TCG GGC CAG CTC GTA GGT GTG GAT CTG   1497
Val Gln Ala Glu His Ser Glu Ser Gly Gln Leu Val Gly Val Asp Leu
                470                 475                 480

AGC ACA GGT GAG CCG ATG GTG GCC GCA GAG ATG GGT GTG TGG GAT AAC   1545
Ser Thr Gly Glu Pro Met Val Ala Ala Glu Met Gly Val Trp Asp Asn
            485                 490                 495

TAC TGT GTG AAG AAG CAG CTG CTA CAC TCC TGT ACT GTG ATC GCC ACC   1593
Tyr Cys Val Lys Lys Gln Leu Leu His Ser Cys Thr Val Ile Ala Thr
        500                 505                 510

AAC ATT CTC CTG GTC GAC GAG ATC ATG CGA GCT GGG ATG TCC TCT CTG   1641
Asn Ile Leu Leu Val Asp Glu Ile Met Arg Ala Gly Met Ser Ser Leu
```

```
                515                 520                 525
AAG GGT TGAGGCCTGC CTGTGATACT ACAGGATGTT GGGGGGAATG GTTATTTTTG              1697
Lys Gly
530

TCCAAGCTTC AAGTGATTTG GAAAAAAATT TTCTCTTCCT GATTGGAGAA AGAAACGGG            1757

ACATTTGACA CCTATTCAAA TTATACTGTA AAATTTTATT TTATTTTTGC CTTGAGTATC          1817

TGAAGACACT CAAAGCAGCT CTTTTTCAAC CCACTGAACA AGATGTTTTA GCTACACCGA          1877

TACAAAAATT ACATAATAAG ATAAGCATGT TGTCTACCCT TGTTCCATAA GTGTTCTTTG          1937

AAAGTTTGTA ATGGTTTTCT CCTAAATAAG GCATGGTGAC ACATGCCTGT AAGCCTAGCC          1997

CTTTGGAAAT AGTCCGGAAT TTCTATGCCA ACTCAGGCTA CAGGAGACCC CAGGTCGAAA          2057

GAATAATTTG TTGTGGATGT ATTTGAAATT ATCCAGCCAA CTCCCTGTTA AACATGTAAG          2117

ATCCTTGCCA GTGTAAAACA CATCTGGGTA ATTTATGGGT TGCATAATGT CTAATAAATA          2177

CTTAAAAGAG TGAAAAAAAA AAAAAAA                                              2205

(2) INFORMATION FOR SEQ ID NO:60:

(i) SEQUENCE CHARACTERISTICS:
        (A) LENGTH: 1734 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 3..1637

(xi) SEQUENCE DESCRIPTION: SEQ ID NO:60:

AG ATG ATG CCC ACA CCA GTT ATC CTG TTG AAA GAG GGT ACT GAT AGC              47
   Met Met Pro Thr Pro Val Ile Leu Leu Lys Glu Gly Thr Asp Ser
     1               5                  10                  15

TCC CAG GGC ATC CCT CAG CTC GTG AGT AAC ATC AGT GCC TGC CAA GTG             95
Ser Gln Gly Ile Pro Gln Leu Val Ser Asn Ile Ser Ala Cys Gln Val
                 20                  25                  30

ATT GCT GAG GCT GTA AGA ACC ACC CTG GGT CCC CGT GGC ATG GAC AAA            143
Ile Ala Glu Ala Val Arg Thr Thr Leu Gly Pro Arg Gly Met Asp Lys
             35                  40                  45

CTT ATT GTG GAT GGC CGA GGC AAA GCA ACA ATA TCT AAT GAT GGG GCC            191
Leu Ile Val Asp Gly Arg Gly Lys Ala Thr Ile Ser Asn Asp Gly Ala
         50                  55                  60

ACA ATT CTG AAA CTC CTC GAT GTT GTC CAT CCT GCA GCA AAG ACT TTA            239
Thr Ile Leu Lys Leu Leu Asp Val Val His Pro Ala Ala Lys Thr Leu
     65                  70                  75

GTG GAC ATA GCC AAG TCC CAG GAT GCT GAG GTT GGT GAT GGC ACC ACC            287
Val Asp Ile Ala Lys Ser Gln Asp Ala Glu Val Gly Asp Gly Thr Thr
 80                  85                  90                  95

TCA GTG ACC CTG CTG GCT GCG GAG TTT CTG AAG CAG GTG AAG CCC TAC            335
Ser Val Thr Leu Leu Ala Ala Glu Phe Leu Lys Gln Val Lys Pro Tyr
                100                 105                 110

GTG GAA GAA GGT TTA CAC CCT CAG ATC ATC ATC CGA GCT TTC CGC ACA            383
Val Glu Glu Gly Leu His Pro Gln Ile Ile Ile Arg Ala Phe Arg Thr
                115                 120                 125

GCC ACC CAA TTG GCT GTT AAC AAA ATC AAA GAG ATA GCT GTG ACT GTG            431
Ala Thr Gln Leu Ala Val Asn Lys Ile Lys Glu Ile Ala Val Thr Val
            130                 135                 140

AAG AAG CAA GAT AAA GTA GAG CAG AGG AAG ATG CTG GAG AAG TGT GCG            479
Lys Lys Gln Asp Lys Val Glu Gln Arg Lys Met Leu Glu Lys Cys Ala
```

```
              145                 150                 155
ATG ACA GCC CTG AGC TCC AAG CTG ATC TCC CAG CAG AAG GTC TTC TTC    527
Met Thr Ala Leu Ser Ser Lys Leu Ile Ser Gln Gln Lys Val Phe Phe
160                 165                 170                 175

GCC AAG ATG GTG GTT GAT GCC GTG ATG ATG CTT GAC GAG CTG CTG CAG    575
Ala Lys Met Val Val Asp Ala Val Met Met Leu Asp Glu Leu Leu Gln
                    180                 185                 190

CTT AAA ATG ATT GGC ATC AAG AAG GTG CAG GGG GGA GCC CTG GAG GAG    623
Leu Lys Met Ile Gly Ile Lys Lys Val Gln Gly Gly Ala Leu Glu Glu
                195                 200                 205

TCT CAG CTA GTT GCT GGT GTT GCG TTC AAG AAG ACT TTC TCT TAT GCT    671
Ser Gln Leu Val Ala Gly Val Ala Phe Lys Lys Thr Phe Ser Tyr Ala
            210                 215                 220

GGG TTT GAA ATG CAG CCC AAG AAG TAT AAG AAC CCC AAG ATT GCC CTC    719
Gly Phe Glu Met Gln Pro Lys Lys Tyr Lys Asn Pro Lys Ile Ala Leu
        225                 230                 235

TTA AAT GTT GAG CTT GAG CTG AAA GCA GAG AAA GAT AAT GCT GAA ATC    767
Leu Asn Val Glu Leu Glu Leu Lys Ala Glu Lys Asp Asn Ala Glu Ile
240                 245                 250                 255

AGA GTC CAC ACA GTG GAG GAT TAC CAG GCA ATT GTT GAT GCC GAG TGG    815
Arg Val His Thr Val Glu Asp Tyr Gln Ala Ile Val Asp Ala Glu Trp
                    260                 265                 270

AAT ATT CTC TAT GAC AAG TTA GAG AAG ATC CAT CAG TCT GGA GCC AAA    863
Asn Ile Leu Tyr Asp Lys Leu Glu Lys Ile His Gln Ser Gly Ala Lys
                275                 280                 285

GTC ATC TTG TCT AAA CTC CCT ATT GGG GAT GTG GCC ACC CAG TAC TTT    911
Val Ile Leu Ser Lys Leu Pro Ile Gly Asp Val Ala Thr Gln Tyr Phe
            290                 295                 300

GCT GAT AGG GAC ATG TTC TGT GCT GGC CGA GTG CCT GAG GAG GAT CTG    959
Ala Asp Arg Asp Met Phe Cys Ala Gly Arg Val Pro Glu Glu Asp Leu
        305                 310                 315

AAG AGG ACG ATG ATG GCT TGT GGA GGC TCA ATC CAG ACC AGT GTG AAT   1007
Lys Arg Thr Met Met Ala Cys Gly Gly Ser Ile Gln Thr Ser Val Asn
320                 325                 330                 335

GCT CTG GTT CCA GAT GTG CTG GGC CAC TGC CAA GTG TTT GAA GAG ACC   1055
Ala Leu Val Pro Asp Val Leu Gly His Cys Gln Val Phe Glu Glu Thr
                    340                 345                 350

CAA ATT GGA GGA GAG AGG TAC AAT TTC TTC ACT GGC TGC CCT AAG GCC   1103
Gln Ile Gly Gly Glu Arg Tyr Asn Phe Phe Thr Gly Cys Pro Lys Ala
                355                 360                 365

AAG ACA TGT ACC ATC ATC CTC CGT GGT GGC GCT GAG CAG TTT ATG GAA   1151
Lys Thr Cys Thr Ile Ile Leu Arg Gly Gly Ala Glu Gln Phe Met Glu
            370                 375                 380

GAG ACA GAG AGG TCC CTA CAT GAT GCC ATC ATG ATT GTG AGG AGG GCC   1199
Glu Thr Glu Arg Ser Leu His Asp Ala Ile Met Ile Val Arg Arg Ala
        385                 390                 395

ATC AAG AAT GAC TCT GTG GTG GCT GGT GGT GGA GCC ATC GAG ATG GAA   1247
Ile Lys Asn Asp Ser Val Val Ala Gly Gly Gly Ala Ile Glu Met Glu
400                 405                 410                 415

CTT TCC AAA TAC CTG CGG GAT TAC TCG AGG ACC ATT CCT GGG AAG CAG   1295
Leu Ser Lys Tyr Leu Arg Asp Tyr Ser Arg Thr Ile Pro Gly Lys Gln
                    420                 425                 430

CAG CTG TTG ATT GGG GCA TAT GCC AAG GCC CTG GAG ATT ATT CCA CGA   1343
Gln Leu Leu Ile Gly Ala Tyr Ala Lys Ala Leu Glu Ile Ile Pro Arg
                435                 440                 445

CAG CTA TGT GAC AAC GCT GGC TTT GAT GCC ACA AAC ATC CTC AAC AAG   1391
Gln Leu Cys Asp Asn Ala Gly Phe Asp Ala Thr Asn Ile Leu Asn Lys
            450                 455                 460

CTG CGG GCT CGA CAC GCA CAG GGA GGT ATG TGG TAT GGG GTG GAC ATC   1439
```

```
Leu Arg Ala Arg His Ala Gln Gly Gly Met Trp Tyr Gly Val Asp Ile
465                 470                 475

AAC AAT GAG AAC ATC GCC GAC AAC TTC CAG GCA TTT GTG TGG GAG CCA    1487
Asn Asn Glu Asn Ile Ala Asp Asn Phe Gln Ala Phe Val Trp Glu Pro
480                 485                 490                 495

GCC ATG GTG CGC ATC AAC GCT CTG ACA GCA GCT TCT GAG GCT GCA TGC    1535
Ala Met Val Arg Ile Asn Ala Leu Thr Ala Ala Ser Glu Ala Ala Cys
                500                 505                 510

CTT ATT GTG TCC GTG GAT GAG ACT ATC AAG AAC CCC CGC TCC ACT GTG    1583
Leu Ile Val Ser Val Asp Glu Thr Ile Lys Asn Pro Arg Ser Thr Val
                515                 520                 525

GAT CCT CCA GCT CCA TCA GCT GGC CGT GGC AGA GGC CAA GCC CGC TTC    1631
Asp Pro Pro Ala Pro Ser Ala Gly Arg Gly Arg Gly Gln Ala Arg Phe
            530                 535                 540

CAC TGAGAGGCGA GGCGGTCTGC ACCTCCTTGT GAGGTGAGGG GGTGGATGAG         1684
His

AAGATGGTTG CTGGTCTGCT GGGTTCTCAC TGAGGTTATT TAAATAAAGC             1734

(2) INFORMATION FOR SEQ ID NO:61:

(i) SEQUENCE CHARACTERISTICS:
        (A) LENGTH: 1853 base pairs
        (B) TYPE: nucleic acid
        (C) STRANDEDNESS: single
        (D) TOPOLOGY: linear (ii) MOLECULE TYPE: cDNA (ix) FEATURE:
         (A) NAME/KEY: CDS
         (B) LOCATION: 86..1732

(xi) SEQUENCE DESCRIPTION: SEQ ID NO:61:

CCCATTCCCA GCAGGCAGTG CGCGGCGCCC CTTGCTTCCT CGGCGTCTCG GAGCGAGCGC    60

GTGAGCGGTG GACTGCGGCC GAGCC ATG GCG CTT CAC GTC CCC AAG GCC CCG    112
                            Met Ala Leu His Val Pro Lys Ala Pro
                              1               5

GGC TTT GCC CAG ATG CTC AAG GAT GGA GCC AAA CAT TTC TCG GGA TTA    160
Gly Phe Ala Gln Met Leu Lys Asp Gly Ala Lys His Phe Ser Gly Leu
 10              15                  20                  25

GAA GAG GCT GTG TAT AGA AAT ATA CAG GCC TGC AAG GAG CTT GCT CAG    208
Glu Glu Ala Val Tyr Arg Asn Ile Gln Ala Cys Lys Glu Leu Ala Gln
                30                  35                  40

ACT ACT CGC ACA GCG TAC GGA CCA AAT GGA ATG AAT AAA ATG GTC ATC    256
Thr Thr Arg Thr Ala Tyr Gly Pro Asn Gly Met Asn Lys Met Val Ile
            45                  50                  55

AAT CGC CTG GAG AAG TTG TTT GTG ACA AAC GAT GCA GCG ACT ATT TTA    304
Asn Arg Leu Glu Lys Leu Phe Val Thr Asn Asp Ala Ala Thr Ile Leu
        60                  65                  70

AGA GAG CTA GAA GTG CAG CAT CCT GCT GCA AAG ATG ATA GTG ATG GCC    352
Arg Glu Leu Glu Val Gln His Pro Ala Ala Lys Met Ile Val Met Ala
    75                  80                  85

TCT CAT ATG CAA GAA CAA GAG GTT GGT GAT GGC ACA AAC TTC GTT CTG    400
Ser His Met Gln Glu Gln Glu Val Gly Asp Gly Thr Asn Phe Val Leu
90                  95                  100                 105

GTG TTC GCT GGG GCT CTT CTG GAA CTA GCT GAA GAA CTT CTG AGG ATT    448
Val Phe Ala Gly Ala Leu Leu Glu Leu Ala Glu Glu Leu Leu Arg Ile
                110                 115                 120

GGC CTG TCA GTA TCA GAG GTA ATA TCG GGG TAT GAA ATA GCT TGC AAA    496
Gly Leu Ser Val Ser Glu Val Ile Ser Gly Tyr Glu Ile Ala Cys Lys
                125                 130                 135
```

```
AAA GCT CAT GAG ATC CTT CCT GAG TTG GTA TGT TGT TCT GCC AAA AAC      544
Lys Ala His Glu Ile Leu Pro Glu Leu Val Cys Cys Ser Ala Lys Asn
        140                 145                 150

CTT CGA GAT GTT GAT GAA GTG TCC TCT CTG CTT CGA ACC TCC ATC ATG      592
Leu Arg Asp Val Asp Glu Val Ser Ser Leu Leu Arg Thr Ser Ile Met
155                 160                 165

AGT AAG CAG TAC GGC AGC GAG ACG TTT TTG GCC AAG CTT ATT GCT CAG      640
Ser Lys Gln Tyr Gly Ser Glu Thr Phe Leu Ala Lys Leu Ile Ala Gln
170                 175                 180                 185

GCT TGT GTT TCT ATC TTT CCT GAT TCT GGC AAT TTC AAT GTT GAT AAC      688
Ala Cys Val Ser Ile Phe Pro Asp Ser Gly Asn Phe Asn Val Asp Asn
                190                 195                 200

ATC AGA GTA TGT AAG ATT CTG GGC TCT GGT ATT TAT TCA TCC TCA GTA      736
Ile Arg Val Cys Lys Ile Leu Gly Ser Gly Ile Tyr Ser Ser Ser Val
        205                 210                 215

TTA CAT GGC ATG GTT TTT AAG AAG GAA ACT GAA GGT GAT GTG ACA TCT      784
Leu His Gly Met Val Phe Lys Lys Glu Thr Glu Gly Asp Val Thr Ser
        220                 225                 230

GTC AAA GAT GCA AAG ATA GCT GTG TAC TCT TGT CCG TTT GAT GGC ATG      832
Val Lys Asp Ala Lys Ile Ala Val Tyr Ser Cys Pro Phe Asp Gly Met
235                 240                 245

ATA ACA GAG ACA AAG GGG ACC GTG CTG ATT AAG ACT GCC GAG GAG CTA      880
Ile Thr Glu Thr Lys Gly Thr Val Leu Ile Lys Thr Ala Glu Glu Leu
250                 255                 260                 265

ATG AAC TTC AGT AAG GGA GAG GAG AAC CTC ATG GAT GCT CAG GTG AAG      928
Met Asn Phe Ser Lys Gly Glu Glu Asn Leu Met Asp Ala Gln Val Lys
                270                 275                 280

GCC ATT GCA GGC ACT GGT GCA AAT GTC ATA GTA ACA GGC GGA AAA GTG      976
Ala Ile Ala Gly Thr Gly Ala Asn Val Ile Val Thr Gly Gly Lys Val
        285                 290                 295

GCG GAC ATA GCT CTT CAT TAT GCT AAC AAG TAC AAT ATC ATG TTG GTG     1024
Ala Asp Ile Ala Leu His Tyr Ala Asn Lys Tyr Asn Ile Met Leu Val
        300                 305                 310

AGA CTG AAC TCA AAG TGG GAT CTC AGA CGA CTC TGT AAA ACA GTT GGT     1072
Arg Leu Asn Ser Lys Trp Asp Leu Arg Arg Leu Cys Lys Thr Val Gly
315                 320                 325

GCC ACA GCT CTT CCA AAA TTG ACT CCT CCC GTC CAA GAA GAA ATG GGA     1120
Ala Thr Ala Leu Pro Lys Leu Thr Pro Pro Val Gln Glu Glu Met Gly
330                 335                 340                 345

CAT TGT GAC AGT GTT TAC CTC TCA GAA GTT GGA GAT ACA CAA GTG GTT     1168
His Cys Asp Ser Val Tyr Leu Ser Glu Val Gly Asp Thr Gln Val Val
                350                 355                 360

GTT TTT AAG CAT GAA AAA GAA GAT GGT GCC ATT TCT ACT ATA GTT CTT     1216
Val Phe Lys His Glu Lys Glu Asp Gly Ala Ile Ser Thr Ile Val Leu
        365                 370                 375

CGA GGT TCT ACA GAC AAT CTG ATG GAT GAC ATA GAA AGG GCA GTA GAT     1264
Arg Gly Ser Thr Asp Asn Leu Met Asp Asp Ile Glu Arg Ala Val Asp
        380                 385                 390

GAT GGA GTT AAT ACT TTC AAA GTT CTC ACA AGG GAT AAG CGT CTT GTA     1312
Asp Gly Val Asn Thr Phe Lys Val Leu Thr Arg Asp Lys Arg Leu Val
395                 400                 405

CCT GGA GGT GGA GCT ACC GAA ATT GAA TTG GCT AAA CAA ATC ACA TCA     1360
Pro Gly Gly Gly Ala Thr Glu Ile Glu Leu Ala Lys Gln Ile Thr Ser
410                 415                 420                 425

TAT GGA GAG ACG TGT CCT GGG CTT GAA CAG TAT GCT ATT AAG AAG TTT     1408
Tyr Gly Glu Thr Cys Pro Gly Leu Glu Gln Tyr Ala Ile Lys Lys Phe
                430                 435                 440

GCT GAA GCG TTT GAA GCG ATT CCA CGG GCA CTG GCA GAA AAT TCT GGC     1456
Ala Glu Ala Phe Glu Ala Ile Pro Arg Ala Leu Ala Glu Asn Ser Gly
        445                 450                 455
```

```
GTG AAG GCC AAT GAA GTT ATC TCT AAA CTT TAT TCC GTA CAC CAA GAA      1504
Val Lys Ala Asn Glu Val Ile Ser Lys Leu Tyr Ser Val His Gln Glu
            460                 465                 470

GGA AAC AAA AAT GTG GGG TTG GAT ATC GAG GCT GAA GTC CCT GCT GTA      1552
Gly Asn Lys Asn Val Gly Leu Asp Ile Glu Ala Glu Val Pro Ala Val
        475                 480                 485

AAG GAT ATG TTA GAA GCC AGT ATT TTA GAT ACT TAC TTG GGA AAA TAC      1600
Lys Asp Met Leu Glu Ala Ser Ile Leu Asp Thr Tyr Leu Gly Lys Tyr
490                 495                 500                 505

TGG GCT ATT AAA CTG GCC ACT AAT GCT GCA GTC ACT GTA CTA AGA GTG      1648
Trp Ala Ile Lys Leu Ala Thr Asn Ala Ala Val Thr Val Leu Arg Val
                510                 515                 520

GAT CAG ATC ATC ATG GCA AAA CCA GCT GGT GGG CCC AAA CCT CCA AGT      1696
Asp Gln Ile Ile Met Ala Lys Pro Ala Gly Gly Pro Lys Pro Pro Ser
            525                 530                 535

GGG AAG AAG GAC TGG GAT GAC GAC CAG AAT GAC TGAGGAACTT GTCATAGGTT    1749
Gly Lys Lys Asp Trp Asp Asp Asp Gln Asn Asp
            540                 545

AAGAGTTGTG TTTGTAGAGT AGAACTTGCC CAGTGTTTTA TTTTTCTTAT TTGTGTTTGT    1809

ACTCTGCTGG GTGGTACAAT AAATGTGTTA CTGTTAAAAA AAAA                     1853

(2) INFORMATION FOR SEQ ID NO:62:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:62:

ATRGTDGCHC CATCRTTDGT                                                  20

(2) INFORMATION FOR SEQ ID NO:63:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:63:

Thr Asn Asp Gly Ala Thr Ile
1               5

(2) INFORMATION FOR SEQ ID NO:64:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:64:

ACATCCAGCA GCTCTGTGAG                                                  20

(2) INFORMATION FOR SEQ ID NO:65:

(i) SEQUENCE CHARACTERISTICS:
```

```
            (A) LENGTH: 20 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:65:

CCTTGCCTAG CACTCACTCC                                          20

(2) INFORMATION FOR SEQ ID NO:66:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:66:

Leu Gly Pro Lys Gly Met Asp Lys Met
1               5

(2) INFORMATION FOR SEQ ID NO:67:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:67:

Thr Ile Thr Asn Asp Gly Ala Thr Ile Leu
1               5                   10

(2) INFORMATION FOR SEQ ID NO:68:

(i) SEQUENCE CHARACTERISTICS:
            (A) LENGTH: 13 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:68:

Gln Asp Asp Glu Val Gly Asp Gly Thr Thr Ser Val Val
1               5                   10

(2) INFORMATION FOR SEQ ID NO:69:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:69:

Glu Arg Ser Leu His Asp Ala Leu
1               5

(2) INFORMATION FOR SEQ ID NO:70:

(i) SEQUENCE CHARACTERISTICS:
```

(A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
        (B) LOCATION: 3
        (D) OTHER INFORMATION: /note= "Ala may be Pro"

(xi) SEQUENCE DESCRIPTION: SEQ ID NO:70:

Val Val Ala Gly Gly Gly Ala
1               5

(2) INFORMATION FOR SEQ ID NO:71:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:71:

Gly Asp Gly Thr Thr
1               5

(2) INFORMATION FOR SEQ ID NO:72:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
        (B) LOCATION: 1
        (D) OTHER INFORMATION: /note= "Ile may be Val"

(ix) FEATURE:
        (B) LOCATION: 3
        (D) OTHER INFORMATION: /note= "Asn may be Lys"

(ix) FEATURE:
        (B) LOCATION: 6
        (D) OTHER INFORMATION: /note= "Ala may be Val"

(ix) FEATURE:
        (B) LOCATION: 7
        (D) OTHER INFORMATION: /note= "Thr may be Ser"

(xi) SEQUENCE DESCRIPTION: SEQ ID NO:72:

Ile Thr Asn Asp Gly Ala Thr
1               5

(2) INFORMATION FOR SEQ ID NO:73:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
        (B) LOCATION: 6
        (D) OTHER INFORMATION: /note= "Ser may be Thr"

-continued (xi) SEQUENCE DESCRIPTION: SEQ ID NO:73:

Gly Asp Gly Thr Thr Ser
1               5

(2) INFORMATION FOR SEQ ID NO:74:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (ix) FEATURE:
        (B) LOCATION: 2
        (D) OTHER INFORMATION: /note= "Ala may be Pro"

(xi) SEQUENCE DESCRIPTION: SEQ ID NO:74:

Val Ala Gly Gly Gly
1               5